US008710203B2

(12) United States Patent
Varnum et al.

(10) Patent No.: US 8,710,203 B2
(45) Date of Patent: Apr. 29, 2014

(54) THERAPEUTIC HUMAN ANTI-IL-1R1 MONOCLONAL ANTIBODY

(71) Applicants: Amgen Inc., Thousand Oaks, CA (US); Medarex, Inc., Princeton, NJ (US)

(72) Inventors: Brian Varnum, Santa Monica, CA (US); Chris Vezina, Newbury Park, CA (US); Alison Witte, Scotts Valley, CA (US); Xueming Qian, Oak Park, CA (US); Francis Hall Martin, Newbury Park, CA (US); Haichun Huang, Fremont, CA (US); Gary Elliot, Thousand Oaks, CA (US)

(73) Assignees: Amgen Inc., Thousand Oaks, CA (US); Medarex, L.L.C., Princeton, NJ (US)

( * ) Notice: Subject to any disclaimer, the term of this patent is extended or adjusted under 35 U.S.C. 154(b) by 0 days.

(21) Appl. No.: 13/961,537

(22) Filed: Aug. 7, 2013

(65) Prior Publication Data

US 2014/0039164 A1 Feb. 6, 2014

Related U.S. Application Data

(63) Continuation of application No. 13/450,126, filed on Apr. 18, 2012, now Pat. No. 8,518,407, which is a continuation of application No. 12/210,313, filed on Sep. 15, 2008, now Pat. No. 8,236,559, which is a continuation of application No. 10/656,769, filed on Sep. 5, 2003, now Pat. No. 7,438,910.

(60) Provisional application No. 60/408,719, filed on Sep. 6, 2002.

(51) Int. Cl.
*C07H 21/04* (2006.01)
(52) U.S. Cl.
USPC ...................................... 536/23.53
(58) Field of Classification Search
None
See application file for complete search history.

(56) References Cited

U.S. PATENT DOCUMENTS

| 4,968,607 | A | 11/1990 | Dower et al. |
| 5,081,228 | A | 1/1992 | Dower et al. |
| 5,180,812 | A | 1/1993 | Dower et al. |
| 5,296,592 | A | 3/1994 | Dower et al. |
| 5,319,071 | A | 6/1994 | Dower et al. |
| 5,488,032 | A | 1/1996 | Dower et al. |
| 5,492,888 | A | 2/1996 | Dower et al. |
| 5,545,806 | A | 8/1996 | Lonberg et al. |
| 5,859,205 | A | 1/1999 | Adair et al. |
| 6,248,516 | B1 | 6/2001 | Winter et al. |
| 6,511,665 | B1 | 1/2003 | Urdal et al. |
| 6,682,736 | B1 | 1/2004 | Hanson et al. |
| 7,115,717 | B2 | 10/2006 | Mori et al. |
| 7,132,281 | B2 | 11/2006 | Hanson et al. |
| 7,202,343 | B2 | 4/2007 | Gudas et al. |
| 7,217,796 | B2 | 5/2007 | Wang et al. |
| 7,438,910 | B2 | 10/2008 | Varnum et al. |
| 2003/0086930 | A1 | 5/2003 | Mueller et al. |
| 2004/0063913 | A1 | 4/2004 | Gram et al. |
| 2005/0084449 | A1 | 4/2005 | Landes et al. |
| 2006/0275211 | A1 | 12/2006 | Jakobovits et al. |
| 2007/0116708 | A1 | 5/2007 | Gudas et al. |
| 2007/0292411 | A1 | 12/2007 | Salcedo et al. |
| 2010/0021466 | A1 | 1/2010 | Granger et al. |

FOREIGN PATENT DOCUMENTS

| EP | 0623674 A1 | 11/1994 |
| JP | 2002512776 A | 5/2002 |
| JP | 2005536534 A | 12/2005 |
| WO | WO-89/04838 A1 | 6/1989 |
| WO | WO-97/07671 A1 | 3/1997 |
| WO | WO-01/09187 A2 | 2/2001 |
| WO | WO-02/16436 A2 | 2/2002 |

OTHER PUBLICATIONS

"Purified Rat Anti-Mouse CD12la (IL Receptor, Type 1, p80) Monoclonal Antibody (No Azide/Low Endotoxin)," Technical Data Sheet, BD Pharmingen, Jun. 2003, p. 1.
Abbas and Lichtman, Cellular and Molecular Immunology, 5th Ed., Saunders Publishing: Philadelphia, p. 144 (2003).
Airenne, K.J., et al., "Recombinant Avidin and Avidin-Fusion Proteins," Biomolecular Engineering, 16:87-92 (1999).
Barbas, S., et al., "Human Autoantibody Recognition of DNA", PNAS, 92:2529-2533 (1995).
Beiboer, S., et al., "Guided Selection of a Pan Carcinoma Specific Antibody Reveals Similar Binding Characteristics yet Structural Divergence Between the Original Murine Antibody and its Human Equivalent," J. Mol. Biol., 296:833-849 (2000).
Chien, N., et al., "Significant Structural and Functional Change of an Antigen-Binding Site by a Distant Amino Acid Substitution: Proposal of a Structural Mechanisam," PNAS, 86:5532-5536 (1989).
Chizzonite, Richard, et al., "Two High-Affinity Interleukin 1 Receptors Represent Separate Gene Products," PNAS, 86:8029-8033 (1989).
Choe, J.Y., et al., "Interleukin 1 Receptor Dependence of Serum Transferred Arthritis Can be Circumvented by Toll-Like Receptor 4 Signaling," The Journal of Experimental Medicine, 197(4):537-542 (2003).
Colman, P.M., "Effects of Amino Acid Sequence Changes on Antibody-Antigen Interactions," Research in Immunology, 145:33-36 (1994).

(Continued)

*Primary Examiner* — Zachary Skelding
(74) *Attorney, Agent, or Firm* — Ropes & Gray LLP

(57) ABSTRACT

Antibodies that interact with interleukin-1 receptor type 1 (IL-1R1) are described. Methods of treating IL-1 mediated diseases by administering a pharmaceutically effective amount of antibodies to IL-1R1 are described. Methods of detecting the amount of IL-1R1 in a sample using antibodies to IL-1R1 are described.

24 Claims, 27 Drawing Sheets

(56) References Cited

OTHER PUBLICATIONS

Cullinan, E., "IL-1 Receptor Accessory Protein is an Essential Component of the IL-1 Receptor," Journal of Immunology, 161:5614-5620 (1998).

D'Ettorre, C., et al., "Functional Epitope Mapping of Human Interleukin-1β by Surface Plasmon Resonance," Eur. Cytokine Netw., 8(2):161-171 (1997).

Dekker, S.K., et al., "Characterization of Interleukin-1α-induced Melanoma Cell Motility: Inhibition by Type I and Type II Receptor-Blocking Monoclonal Antibodies," Melanoma Research, 7:223-230 (1997).

Desiderio, A., et al., "A Semi-Synthetic Repertoire of Intrinsically Stable Antibody Fragments Derived from a Single-Framework Scaffold," J. Mol. Biol., 310:603-615 (2001).

Desmyter, A., et al., "Antigen Specificity and High Affinity Binding Provided by One Single Loop of a Camel Single-Domain Antibody," The Journal of Biogiical Chemistry, 276(28):26285-26290 (2001).

Ditzel, H., "Determinants of Polyreactivity in a Large Panel of Recombinant Human Antibodies from HIV-1 Infection," J. Immunol., 157(2):739-749 (1996).

Dripps, D., et al., "Interleukin-1 (IL-1) Receptor Antagonist Binds to the 80-kDa IL-1 Receptor but Does Not Initiate IL-1 Signal Transduction," The Journal of Biological Chemistry, 266(16):10331-10336 (1991).

Dripps, D., et al., "Interleukin-1 (IL-1) Receptor Antagonist Binds to the Type II Interleukin-1 Receptor on B Cells and Neutrophils," 266(30):20311-20315 (1991).

Edinger, A.L., et al., "Characterization and Epitope Mapping of Neutralizing Monoclonal Antibodies Produced by Immunization with Oligomeric Simian Immunodefiency Virus Envelope Protein," Journal of Virology, 74(17):7922-7935 (2000).

Fredericks, Z., et al., "Identification of Potent Human Anit-IL-IR, Antagonist Antibodies," Protein Engineering, Design and Selection, 17(1):95-106 (2004).

GenBank Accession No. AAM46660.1 (Aug. 20, 2002).

GenBank Accession No. CAD35492.1 (Jun. 18, 2002).

Goldsby, R., et al., Immunology, 5th Edition, W. H. Freeman and Co., New York, p. 83, 2002.

Greenfeder, S., et al., "Molecular Cloning and Characterization of a Second Subunit of the Interleukin 1 Receptor Complex," The Journal of Biological Chemistry, 270(23):13767-13765 (1995).

Harlow and Lane, Antibodies—A Laboratory Manual, Cold Spring Harbor Press, New York, p. 76 (1988).

International Search Report from related International Patent Application No. PCT/US03/27978, mailed Oct. 14, 2005.

Janeway, C., et al., Immunology, 3rd Edition, Garland Publishing, New York, pp. 31-35 (1997).

Janeway, C., et al., Immunobiology, 5th Edition, Garland Publishing, New York, pp. 94-105 (2001).

Kay, B., et al., "An MI3 Phage Library Displaying Random 38-Amino-Acid Peptides as a Source of Novel Sequences with Affinity to Selected Targets," Gene, 128(1):59-65 (1993).

Klasing, K.C., et al., "Soluble Type-I Interleukin-1 Receptor Blocks Chicken IL-1 Activity," Developmental & Comparative Immunology, 25:345-352 (2001).

Klimka, A., et al., "Human Anti-CD30 Recombinant Antibodies by Guided Phage Antibody Selection Using Cell Panning," British Journal of Cancer, 83(2):252-260 (2000).

McIntyre, K., et al., "Inhibition of Interleukin 1 (IL-1) Binding and Bioactivity In Vitro and Modulation of Acute Inflammation in Vivo by Il-1 Receptor Antagonist and Anti-IL-1 Receptor Monoclonal Antibody," J. Exp. Med, 173:931-939 (1991).

McMahan, C., et al., "A Novel IL-1 Receptor, Cloned from B Cells by Mammalian Expression, is Expressed in Many Cell Types," The EMBO Journal, 10(10):2821-2832 (1991).

Neta, R., "In Vivo Modulation with Anti-Interleukin-1 (1L-1) Receptor (p80) Antobody 35F5 of the Response to IL-1. The Relationship of Radioprotection, Colony-Stimultaing Factor, and IL-6," Blood, 76(1):57-62 (1990).

Oldenburg, H., et al., "Interleukin 1 Binding to its Type I, but not Type II Receptor, Modulates the In Vivo Acute Phase Response," Cytokine, 7(6):510-516 (1995).

Padlan, EA., "Anatomy of the antibody molecule," Mol Immunol., 31(3):169-217 (1994).

Portolano, S., et. al., "Lack of promiscuity in autoantigen-specific H and L chain combinations as revealed by human H and L chain "roulette"," J Immunol., 150(3):880-887 (1993).

Probert, L., et al., "The Type 1 Interleukin-1 Receptor Acts in Series with Tumor Necrosis Factor (TNF) to Induce Arthritis in TNF-Transgenic Mice," Eur. J. Immunol., 25:1794-1797 (1995).

Rader, C., et al., "A Phage Display Approach for Rapid Antibody Humanization: Designed Combinatorial V Gene Libraries," PNAS, 95(15):8910-8915 (1998).

Rogers, H., et al., "Interleukin 1 Participates in the Development of Anti-Listeria Response in Normal and SCID mice," PNAS, 89:1011-1015 (1992).

Rudikoff, S., et al., "Single Amino Acid Substitution Altering Antigen-Binding Specificity," PNAS, 79:1979-1983 (1982).

Schier, R., et al., "Isolation of Picomolar Affinity Anti-c-erbB-2 Single-Chain Fv by Molecular Evolution of the Complementarity Determining Regions in the Center of the Antibody Binding Site," J. Mol. Biol., 263:551-567 (1996).

Schreuder, H., et al., "A New Cytokine-Receptor Binding Mode Revealed by the Crystal Structure of the IL-1 Receptor with an Antagonist," Nature, 386:194-200 (1997).

Schäfers, M., et al., "Combined Epineurial Therapy with Neutralizing Antibodies to Tumor Necrosis Factor-Alpha and Interleukin-1 Receptor has an Additive Effect in Reducing Neuropathic Pain in Mice," Neuroscience Letters 310:113-116 (2001).

Search Report from related Japanese Patent Application No. 2004-534705.

Search Report from related Taiwanese Patent Application No. 095140332, dated Jun. 25, 2007.

Sims, J., et al., "Interleukin 1 Signaling Occurs Exclusively Via the Type I Receptor," PNAS, 90:6155-6159 (1993).

Sommer, C., et al., "Neutralizing Antibodies to Interleukin I-Receptor Reduce Pain Associated Behavior in Mice wih Experimental Neuropathy," Neuroscience Letters 270:25-28 (1999).

Supplementary Partial European Search Report, from related European Patent Application No. EP03752058 dated Jan. 26, 2007.

Vajdos, FF., et. al., "Comprehensive functional maps of the antigen-binding site of an anti-ErbB2 antibody obtained with shotgun scanning mutagenesis," J Mol Biol., 320(2):415-428 (2002).

Vigers, G., et al., "Crystal Structure of the Type I Interleukin-1 Receptor Complexed with Interleukin-1β," Nature, 386:190-194 (1997).

Vigers, G., et al., "X-ray Crystal Structure of a Small Antagonist Peptide Bound to Interleukin-1 Receptor Type 1", J. Biol. Chem., 275(47):36927-36933 (2000).

Walsh, B.J and Howden, M.E.H., A Method for the Detection of IgE Binding Sequences of Allergens Based on Modification of Epitope Mapping, Journal of Immunological Methods, 121:275-280 (1989).

Wesche, H., et al., "Effects of IL-1 Receptor Accessory Protein on IL-1 Binding," FEBS Letters, 429:303-306 (1998).

Williams, R., et al., "Evaluation of TNF-αand IL-1 Blockate in Collagen-Induced Arthritis and Comparison and Combined Anti-TNF-α/ Anti-CD4 Therapy," J. Immunology, 165:7240-7245 (2000).

Xu et al., "Epitope Mapping of Two Immunodominant Domains of gp41, the Transmembrane Protein of Human Immunodeficiency Virus Type 1, Using Ten Human Monoclonal Antibodies," Journal of Virology, pp. 4832-4838 (1991).

Yoon, DY., et. al., "Antibodies to domains II and III of the IL-1 receptor accessory protein inhibit IL-1 beta activity but not binding: regulation of IL-1 responses is via type I receptor, not the accessory protein," J Immunol., 160(7):3170-3179 (1998).

FIG. 1A

Heavy Chain IgG1 Constant Region

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctggggggga  360
ccgtcagtct tcctcttccc cccaaaaccc aaggacaccc tcatgatctc ccggaccsct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                    990
```

FIG. 1B

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330
```

FIG. 2A

Kappa Chain Constant Region

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                              321
```

FIG. 2B

```
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107
```

FIG. 3A

Heavy Chain IgG2 Constant Region

```
gcctccacca agggcccatc ggtcttcccc ctggcgccct gctccaggag cacctccgag    60
agcacagcgg ccctgggctg cctggtcaag gactacttcc ccgaaccggt gacggtgtcg   120
tggaactcag gcgctctgac cagcggcgtg cacaccttcc cagctgtcct acagtcctca   180
ggactctact ccctcagcag cgtggtgacc gtgccctcca gcaacttcgg cacccagacc   240
tacacctgca acgtagatca caagcccagc aacaccaagg tggacaagac agttgagcgc   300
aaatgttgtg tcgagtgccc accgtgccca gcaccacctg tggcaggacc gtcagtcttc   360
ctcttccccc caaaacccaa ggacaccctc atgatctccc ggacccctga ggtcacgtgc   420
gtggtggtgg acgtgagcca cgaagacccc gaggtccagt tcaactggta cgtggacggc   480
gtggaggtgc ataatgccaa gacaaagcca cgggaggagc agttcaacag cacgttccgt   540
gtggtcagcg tcctcaccgt tgtgcaccag gactggctga acggcaagga gtacaagtgc   600
aaggtctcca acaaaggcct cccagccccc atcgagaaaa ccatctccaa aaccaaaggg   660
cagccccgag aaccacaggt gtacaccctg cccccatccc gggaggagat gaccaagaac   720
caggtcagcc tgacctgcct ggtcaaaggc ttctacccca gcgacatcgc cgtggagtgg   780
gagagcaatg ggcagccgga gaacaactac aagaccacac ctcccatgct ggactccgac   840
ggctccttct tcctctacag caagctcacc gtggacaaga gcaggtggca gcaggggaac   900
gtcttctcat gctccgtgat gcatgaggct ctgcacaacc actacacgca gaagagcctc   960
tccctgtctc cgggtaaa                                                  978
```

FIG. 3B

```
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSPGK                                         326
```

FIG. 4A

Heavy Chain IgG4 Constant Region

```
gccagcacca agggcccatc cgtcttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca acgtagatca caagcccagc aacaccaagg tggacaagag agttgagtcc   300
aaatatggtc cccatgccca tcatgccca gcctgagt tcctggggggg accatcagtc   360
ttcctgttcc ccccaaaacc caaggacact ctcatgatct cccggacccc tgaggtcacg   420
tgcgtggtgg tggacgtgag ccaggaagac ccgaggtcc agttcaactg gtacgtggat   480
ggcgtggagg tgcataatgc caagacaaag ccgcgggagg agcagttcaa cagcacgtac   540
cgtgtggtca gcgtcctcac cgtcctgcac caggactggc tgaacggcaa ggagtacaag   600
tgcaaggtct ccaacaaagg cctcccgtcc tccatcgaga aaaccatctc caaagccaaa   660
gggcagcccc gagagccaca ggtgtacacc ctgcccccat cccaggagga gatgaccaag   720
aaccaggtca gcctgacctg cctggtcaaa ggcttctacc ccagcgacat cgccgtggag   780
tgggagagca atgggcagcc ggagaacaac tacaagacca cgcctcccgt gctggactcc   840
gacggctcct tcttcctcta cagcaggcta accgtgraca agagcaggtg gcaggagggg   900
aatgtcttct catgctccgt gakgcatgag gctctgcaca accactacac acagaagagc   960
ctctccctgt ctctgggtaa a                                              981
```

FIG. 4B

```
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                        327
```

FIG. 5A

26F5 Heavy Chain

```
atggagtttg ggctgagctg ggtcttcctc gttgctcttt taagaggtgt ccagtgtcag    60
gtgcagctgg tggagtctgg gggaggcgtg gtccagcctg ggaggtccct gagactctcc   120
tgtgcagcgt ctggattcac cttcagcaac tatggcatgc actgggtccg ccaggctcca   180
ggcaaggggc tggagtgggt ggcaggcatt tggaatgatg gaattaataa ataccatgca   240
cactccgtga ggggccgatt caccatctcc agagacaatt ccaagaacac gctgtatctg   300
caaatgaaca gcccgagagc cgaggacacg gctgtgtatt actgtgcgag agcacggtct   360
ttcgactggc tattatttga gttctggggc cagggaaccc tggtcaccgt ctctagt     417
```

FIG. 5B

```
MEFGLSWVFL VALLRGVQCQ VQLVESGGGV VQPGRSLRLS CAASGFTFSN YGMHWVRQAP    60
GKGLEWVAGI WNDGINKYHA HSVRGRFTIS RDNSKNTLYL QMNSPRAEDT AVYYCARARS   120
FDWLLFEFWG QGTLVTVSS                                                139
```

FIG. 6A

26F5 Kappa Chain

```
atggaagccc cagctcagct tctcttcctc ctgctactct ggctcccaga taccaccgga    60
gaaattgtgt tgacacagtc tccagccacc ctgtctttgt ctccagggga aagagccacc   120
ctctcctgca gggccagtca gagtgttagc agctacttag cctggtacca acagaaacct   180
ggccaggctc ccaggctcct catctatgat gcatccaaca gggccactgg catcccagcc   240
aggttcagtg gcagtgggtc tgggacagac ttcactctca ccatcagcag cctagagcct   300
gaagattttg cagtttatta ctgtcagcag cgtagcaact ggcctccgct cactttcggc   360
ggagggacca aggtggagat caaa                                          384
```

FIG. 6B

```
MEAPAQLLFL LLLWLPDTTG EIVLTQSPAT LSLSPGERAT LSCRASQSVS SYLAWYQQKP    60
GQAPRLLIYD ASNRATGIPA RFSGSGSGTD FTLTISSLEP EDFAVYYCQQ RSNWPPLTFG   120
GGTKVEIK                                                           128
```

FIG. 7A

27F2 Heavy Chain

```
atggagtttg ggctgagctg ggttttcctc gttgctcttt taagaggtgt ccagtgtcag    60
gtgcagctgg tggagtctgg gggaggcgtg gtccagcctg gaggtccct gagactctcc   120
tgtgcagtgt ctggattcac cttcagtaac tatggcatgc actgggtccg ccaggctcca   180
ggcaaggggc tggagtgggt ggcagctata tggaatgatg gagaaaataa acaccatgca   240
ggctccgtga ggggccgatt caccatctcc agagacaatt ccaagaacac gctgtatctg   300
caaatgaaca gcctgagagc cgaggacacg gctgtgtatt actgtgcgag aggacgatat   360
tttgactggt tattatttga gtattggggc cagggaaccc tggtcaccgt ctctagt      417
```

FIG. 7B

```
MEFGLSWVFL VALLRGVQCQ VQLVESGGGV VQPGRSLRLS CAVSGFTFSN YGMHWVRQAP    60
GKGLEWVAAI WNDGENKHHA GSVRGRFTIS RDNSKNTLYL QMNSLRAEDT AVYYCARGRY   120
FDWLLFEYWG QGTLVTVSS                                                139
```

FIG. 8A

15C4 Heavy Chain

```
atggggtcaa ccgccatcct cgccctcctc ctggctgttc tccaaggagt ctgtgccgag   60
gtgcagctga tgcagtctgg agcagaggtg aaaaagcccg gggagtctct gaagatctcc  120
tgtaagggtt ctggatacag cttttccttc cactggatcg cctgggtgcg ccagatgccc  180
gggaaaggcc tggagtggat ggggatcatc catcctggtg cctctgatac cagatacagc  240
ccgtccttcc aaggccaggt caccatctca gccgacaact ccaacagcgc cacctacctg  300
cagtggagca gcctgaaggc ctcggacacc gccatgtatt tctgtgcgag acaaagggaa  360
ctcgactact tgactactg gggccaggga accctggtca ccgtctctag t           411
```

FIG. 8B

```
MGSTAILALL LAVLQGVCAE VQLMQSGAEV KKPGESLKIS CKGSGYSFSF HWIAWVRQMP   60
GKGLEWMGII HPGASDTRYS PSFQGQVTIS ADNSNSATYL QWSSLKASDT AMYFCARQRE  120
LDYFDYWGQG TLVTVSS                                                 137
```

FIG. 9A

15C4 Kappa Chain

```
atgtcgccat cacaactcat tgggtttctg ctgctctggg ttccagcctc caggggtgaa      60
attgtgctga ctcagtctcc agactttcag tctgtgactc caaaggagaa agtcaccatc     120
acctgccggg ccagtcagag cattggtagt agcttacact ggtaccagca gaaaccagat     180
cagtctccaa agctcctcat caagtatgct tccagtcct tctcaggggt ccctcgagg       240
ttcagtggca gtggatctgg gacagatttc accctcacca tcaatagcct ggaagctgaa     300
gatgctgcag cgtattactg tcatcagagt agtagtttac ctctcacttt cggcggaggg     360
accaaggtgg agatcaaa                                                    378
```

FIG. 9B

```
MSPSQLIGFL LLWVPASRGE IVLTQSPDFQ SVTPKEKVTI TCRASQSIGS SLHWYQQKPD      60
QSPKLLIKYA SQSFSGVPSR FSGSGSGTDF TLTINSLEAE DAAAYYCHQS SSLPLTFGGG     120
TKVEIK                                                                 126
```

FIG. 10

```
                                                CDR1                      CDR2
26F5   QVQLVESGGG  VVQPGRSLRL  SCAASGFTFS  NYGMHWVRQA  PGKGLEWVAG  IWNDGINKYH
27F2   QVQLVESGGG  VVQPGRSLRL  SCAVSGFTFS  NYGMHWVRQA  PGKGLEWVAA  IWNDGENKHH
15C4   EVQLMQSGAE  VKKPGESLKI  SCKGSGYSFS  FHWIAWVRQM  PGKGLEWMGI  IHPGASDTRY

CDR3
26F5   AHSVRGRFTI  SRDNSKNTLY  LQMNSPRAED  TAVYYCARAR  SFDWLLFEFW  GQGTLVTVSS
27F2   AGSVRGRFTI  SRDNSKNTLY  LQMNSLRAED  TAVYYCARGR  YFDWLLFEYW  GQGTLVTVSS
15C4   SPSFQGQVTI  SADNSNSATY  LQWSSLKASD  TAMYFCARQR  ELDYFDYWGQ  GTLVTVSS
```

FIG. 11

```
                          CDR1
26F5/27F2   EIVLTQSPAT LSLSPGERAT LSCRASQSVS SYLAWYQQKP GQAPRLLIYD
15C4        EIVLTQSPDF QSVTPKEKVT ITCRASQSIG SSLHWYQQKP DQSPKLLIKY

CDR2                                          CDR3
26F5/27F2   ASNRATGIPA RFSGSGSGTD FTLTISSLEP EDFAVYYCQQ RSNWPPLTFG
15C4        ASQSFSGVPS RFSGSGSGTD FTLTINSLEA EDAAAYYCHQ SSSLPLTFGG

26F5/27F2   GGTKVEIK
15C4        GTKVEIK
```

FIG. 17

```
                                                                    K336
    hIL-1R  [diagram with disulfide bonds S—S, S—S, S—S]
                                               14
      226  P  V  I  V  S  P  A  N  E  T  M  E  V  D  L  G  S
hu    758  cctgtgattgtgagcccagctaatgagacaatggaagtagacttgggatc  807
           |||||||||| ||||||||  ||||||||| ||||||| |||  |||||
rat  1048  cctgtgattatgagcccacggaatgagacgatggaagctgacccaggatc  1097
              15           M     R                    A    P
                                                           1
           Q  I  Q  L  I  C  N  V  T  G  Q  L  S  D  I  A  Y
      808  ccagatacaattgatctgtaatgtcaccggccagttgagtgacattgctt  857
           |  ||||||| ||||||||| || ||||||| ||||||||| | ||| ||| |
     1098  cacgatacaactgatctgcaacgtcacgggccagttcacgaccttgtct  1147
              T                  2           F  T     L  3 V
           W  K  W  N  G  S  V  I  D  E  D  D  P  V  L  G
      858  actggaagtggaatgggtcagtaattgatgaagatgacccagtgctaggg  907
           |||||||||||||||||||| | |||||| || ||  ||| |  ||||
     1148  actggaagtggaatgggtcggaaattgatgggacgatccaatcctagcc  1197
                               E    E  W              I     A
                         4          5              6
           E  D  Y  Y  S  V  E  N  P  A  N  K  R  R  S  T  L
      908  gaagactattacagtgtggaaaatcctgcaaacaaaagaaggagtaccct  957
           |||||||||| |   ||||||  |  ||| ||  |||||||  ||  ||
     1198  gaagactatcagttttttggaacacccttcagccaaaagaaagtacactct  1247
                   Q 7 F  L           H     S  A        K  Y 9
                                      8
           I  T  V  L  N  I  S  E  I  E  S  R  F  Y  K  H  P
      958  catcacagtgcttaatatatcggaaattgaaagtagattttataaacatc  1007
           |||  |||   ||||||| |   ||   | ||| |||||| |||||| |||
     1248  cattacaacacttaacgtttcagaggtcaaaagccagttttatcgctatc  1297
              T  10      V           V  K   Q 11      R  Y
           F  T  C  F  A  K  N  T  H  G  I  D  A  A  Y  I
     1008  catttacctgttttgccaagaatacacatggtatagatgcagcatatatc  1057
           | ||  ||| ||| |  ||||| ||  || | ||| | |||  |  |
     1298  cgttcatctgcttcgttaagaacactcatattctggagactgcacacgta  1347
              I           V              I  L  E  T     H  V
              12              13.1
           Q  L  I  Y  P  V  T  N  F  Q  K336  tm domain begins
     1058  cagttaatatatccagtcactaatttccagaagcacatgattggtatatg  1107
           | ||||  ||||  ||||| || || ||  ||||||  || | || ||     |
     1348  cggttagtataccagttcctgacttcaagaattacctcatcgggggctt  1397
           R     V           P  D        K  tm domain begins
```

FIG. 23

```
MVHATSPLLL LLLLSLALVA PGLSARKCSL TGKWTNDLGS NMTIGAVNSK GEFTGTYTTA      60
VTATSNEIKE SPLHGTQNTI NKRTQPTFGF TVNWKFSEST TVFTGQCFID RNGKEVLKTM     120
WLLRSSVNDI GDDWKATRVG INIFTRLRTQ KEQLLASLLE ADKCKEREEK IILVSSANEI    180
DVRPCPLNPN EHKGTITWYK DDSKTPVSTE QASRIHQHKE KLWFVPAMVE DSGHYYCVVR    240
NSSYCLRIKI SAKFVENEPN LCYNAQAIFK QKLPVAGDGG LVCPYMEFFK NENNELPKLQ    300
WYKDCKPLLL DNIHFSGVKD RLIVMNVAEK HRGNYTCHAS YTYLGKQYPI TRVIEFITLE    360
ENKPTRPVIV SPANETMEVD LGSQIQLICN VTGQLSDIAY WKWNGSVIDE DDPVLGEDYY    420
SVENPANKRR STLITVLNIS EIESRFYKHP FTCFAKNTHG IDAAYIQLIY PVTNFQKDYK    480
DDDDK                                                                485
```

FIG. 24

```
  1  MVHATSPLLL LLLLSLALVA PGLSARKCSL TGKWTNDLGS NMTIGAVNSK GEFTGTYTTA
 61  VTATSNEIKE SPLHGTQNTI NKRTQPTFGF TVNWKFSEST TVFTGQCFID RNGKEVLKTM
121  WLLRSSVNDI GDDWKATRVG INIFTRLRTQ KEQLLASLLE ADKCNEREEK IILVSSANEI
181  DVRPCPLNPN EYKGTITWYK NDSKTPISTE QASRIHQHKK KLWFVPAKVE DSGHYYCVVR
241  NSSYCLRIKI TAKFVENEPN LCYNAEAIFK QRLPVAGDGG LVCPYMEFFK DENNELPKLL
301  WYKDCKPLLL DNIHFSGVKD RLIVMNVAEK HRGNYTCHAS YTYLGKQYPI TRVIEFITLE
                            mutation 1   mutation 2
                                 ↓           ↓
361  ENKPTRPVIV SPANETIEVD LGSQIQLICN VTGQLSDTAY WKWNGSFIDE DDPVLGEDYY
     human                             I          V
                      mutation 10.1  mutation 10.2
                                ↓↓
421  SVENPANKRR STLITVLNIS ETESRFYKHP FTCLARNTHG MDAAYVQLIY PVTKFQKDYK
     human                            F  K
481  DDDDK
```

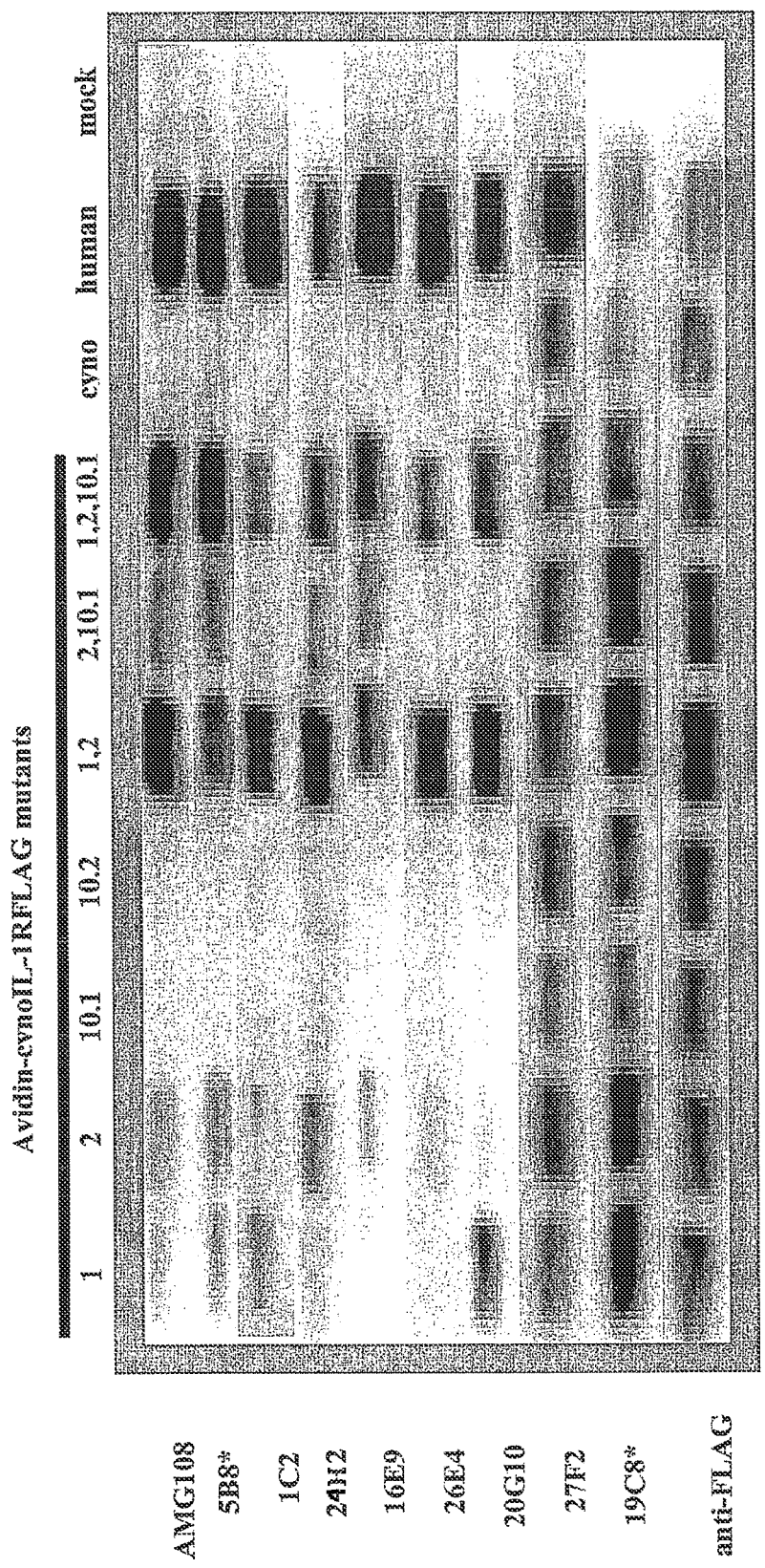

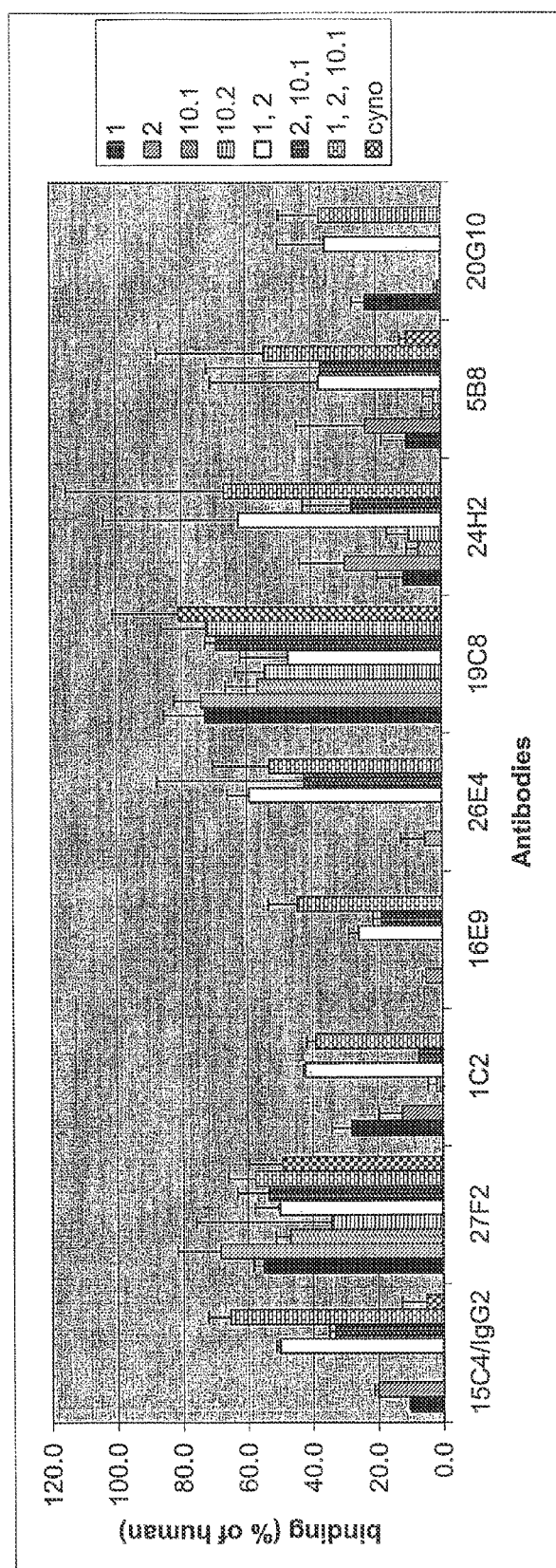

SEQUENCE LISTING

<160> NUMBER OF SEQ ID NOS: 89

<210> SEQ ID NO 1
<211> LENGTH: 990
<212> TYPE: DNA
<213> ORGANISM: Homo Sapiens

<400> SEQUENCE: 1

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990
```

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 321
<212> TYPE: DNA
<213> ORGANISM: Homo Sapiens

<400> SEQUENCE: 3
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321

<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
                85                  90                  95

Pro Val Thr Lys Ser Phe Asn Arg Gly Glu Cys
        100                 105

<210> SEQ ID NO 5
<211> LENGTH: 978
<212> TYPE: DNA
<213> ORGANISM: Homo sapiens

<400> SEQUENCE: 5
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac tcccatgct ggactccgac     840 ggctccttct cctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                  978

<210> SEQ ID NO 6
<211> LENGTH: 326
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

```
Thr Leu Met Ile Ser Arg Thr Pro Glu Val Thr Cys Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 7
<211> LENGTH: 981
<212> TYPE: DNA
<213> ORGANISM: Homo Sapiens

<400> SEQUENCE: 7
gccagcacca aggggccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtgraca agagcaggtg gcaggagggg     900
aatgtcttct catgctccgt gakgcatgag gctctgcaca accactacac acagaagagc     960
ctctccctgt ctctgggtaa a                                              981
```

<210> SEQ ID NO 8
<211> LENGTH: 327
<212> TYPE: PRT
<213> ORGANISM: Homo sapiens

<400> SEQUENCE: 8

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 9
<211> LENGTH: 417
<212> TYPE: DNA
<213> ORGANISM: Homo Sapiens

<400> SEQUENCE: 9

```
atggagtttg ggctgagctg ggtcttcctc gttgctcttt taagaggtgt ccagtgtcag      60
gtgcagctgg tggagtctgg gggaggcgtg gtccagcctg gaggtccct  gagactctcc     120 tgtgcagcgt ctggattcac cttcagcaac tatggcatgc actgggtccg ccaggctcca    180 ggcaagggc tggagtgggt ggcaggcatt tggaatgatg aattaataa ataccatgca      240 cactccgtga ggggccgatt caccatctcc agagacaatt ccaagaacac gctgtatctg    300
caaatgaaca gcccgagagc cgaggacacg gctgtgtatt actgtgcgag agcacggtct    360
ttcgactggc tattatttga gttctggggc cagggaaccc tggtcaccgt ctctagt       417
```

```
<210> SEQ ID NO 10
<211> LENGTH: 139
<212> TYPE: PRT
<213> ORGANISM: Homo sapiens

<400> SEQUENCE: 10

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Asn Tyr Gly Met His Trp Val Arg Gln Ala Pro Gly Lys Gly Leu
        50                  55                  60

Glu Trp Val Ala Gly Ile Trp Asn Asp Gly Ile Asn Lys Tyr His Ala
65                  70                  75                  80

His Ser Val Arg Gly Arg Phe Thr Ile Ser Arg Asp Asn Ser Lys Asn
                85                  90                  95

Thr Leu Tyr Leu Gln Met Asn Ser Pro Arg Ala Glu Asp Thr Ala Val
            100                 105                 110

Tyr Tyr Cys Ala Arg Ala Arg Ser Phe Asp Trp Leu Leu Phe Glu Phe
        115                 120                 125

Trp Gly Gln Gly Thr Leu Val Thr Val Ser Ser
    130                 135
```

```
<210> SEQ ID NO 11
<211> LENGTH: 384
<212> TYPE: DNA
<213> ORGANISM: Homo Sapiens

<400> SEQUENCE: 11
atggaagccc cagctcagct tctcttcctc ctgctactct ggctcccaga taccaccgga     60
gaaattgtgt tgacacagtc tccagccacc ctgtctttgt ctccagggga aagagccacc   120
ctctcctgca gggccagtca gagtgttagc agctactag  cctggtacca acagaaacct   180
ggccaggctc ccaggctcct catctatgat gcatccaaca gggccactgg catcccagcc  240
aggttcagtg gcagtgggtc tgggacagac ttcactctca ccatcagcag cctagagcct  300
gaagattttg cagtttatta ctgtcagcag cgtagcaact ggcctccgct cactttcggc  360
ggagggacca aggtggagat caaa                                          384
```

```
<210> SEQ ID NO 12
<211> LENGTH: 128
<212> TYPE: PRT
<213> ORGANISM: Homo sapiens

<400> SEQUENCE: 12

Met Glu Ala Pro Ala Gln Leu Leu Phe Leu Leu Leu Leu Trp Leu Pro
```

```
                 1               5                  10                 15
Asp Thr Thr Gly Glu Ile Val Leu Thr Gln Ser Pro Ala Thr Leu Ser
                20                  25                 30

Leu Ser Pro Gly Glu Arg Ala Thr Leu Ser Cys Arg Ala Ser Gln Ser
                35                  40                 45

Val Ser Ser Tyr Leu Ala Trp Tyr Gln Gln Lys Pro Gly Gln Ala Pro
                50                  55                 60

Arg Leu Leu Ile Tyr Asp Ala Ser Asn Arg Ala Thr Gly Ile Pro Ala
65                  70                  75                 80

Arg Phe Ser Gly Ser Gly Ser Gly Thr Asp Phe Thr Leu Thr Ile Ser
                85                  90                 95

Ser Leu Glu Pro Glu Asp Phe Ala Val Tyr Tyr Cys Gln Gln Arg Ser
                100                 105                110

Asn Trp Pro Pro Leu Thr Phe Gly Gly Gly Thr Lys Val Glu Ile Lys
                115                 120                125

<210> SEQ ID NO 13
<211> LENGTH: 417
<212> TYPE: DNA
<213> ORGANISM: Homo Sapiens

<400> SEQUENCE: 13
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120 tgtgcagtgt ctggattcac cttcagtaac tatggcatgc actgggtccg ccaggctcca    180 ggcaagggc tggagtgggt ggcagctata tggaatgatg agaaaataa acaccatgca      240 ggctccgtga ggggccgatt caccatctcc agagacaatt ccaagaacac gctgtatctg    300
caaatgaaca gcctgagagc cgaggacacg gctgtgtatt actgtgcgag aggacgatat    360
tttgactggt tattatttga gtattggggc cagggaaccc tggtcaccgt ctctagt       417

<210> SEQ ID NO 14
<211> LENGTH: 139
<212> TYPE: PRT
<213> ORGANISM: Homo sapiens

<400> SEQUENCE: 14

Met Glu Phe Gly Leu Ser Trp Val Phe Leu Val Ala Leu Leu Arg Gly
1               5                   10                 15

Val Gln Cys Gln Val Gln Leu Val Glu Ser Gly Gly Gly Val Val Gln
                20                  25                 30

Pro Gly Arg Ser Leu Arg Leu Ser Cys Ala Val Ser Gly Phe Thr Phe
                35                  40                 45

Ser Asn Tyr Gly Met His Trp Val Arg Gln Ala Pro Gly Lys Gly Leu
                50                  55                 60

Glu Trp Val Ala Ala Ile Trp Asn Asp Gly Glu Asn Lys His His Ala
65                  70                  75                 80

Gly Ser Val Arg Gly Arg Phe Thr Ile Ser Arg Asp Asn Ser Lys Asn
                85                  90                 95

Thr Leu Tyr Leu Gln Met Asn Ser Leu Arg Ala Glu Asp Thr Ala Val
                100                 105                110

Tyr Tyr Cys Ala Arg Gly Arg Tyr Phe Asp Trp Leu Leu Phe Glu Tyr
                115                 120                125

Trp Gly Gln Gly Thr Leu Val Thr Val Ser Ser
                130                 135
```

<210> SEQ ID NO 15
<211> LENGTH: 411
<212> TYPE: DNA
<213> ORGANISM: Homo Sapiens

<400> SEQUENCE: 15

```
atggggtcaa ccgccatcct cgccctcctc ctggctgttc tccaaggagt ctgtgccgag      60
gtgcagctga tgcagtctgg agcagaggtg aaaaagcccg gggagtctct gaagatctcc     120
tgtaagggtt ctggatacag cttttccttc actggatcg cctgggtgcg ccagatgccc      180
gggaaaggcc tggagtggat ggggatcatc catcctggtg cctctgatac cagatacagc     240
ccgtccttcc aaggccaggt caccatctca gccgacaact ccaacagcgc cacctacctg     300
cagtggagca gcctgaaggc ctcggacacc gccatgtatt tctgtgcgag acaaagggaa     360
ctcgactact ttgactactg gggccaggga accctggtca ccgtctctag t              411
```

<210> SEQ ID NO 16
<211> LENGTH: 137
<212> TYPE: PRT
<213> ORGANISM: Homo sapiens

<400> SEQUENCE: 16

```
Met Gly Ser Thr Ala Ile Leu Ala Leu Leu Ala Val Leu Gln Gly
1               5                   10                  15

Val Cys Ala Glu Val Gln Leu Met Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Ser Phe His Trp Ile Ala Trp Val Arg Gln Met Pro Gly Lys Gly Leu
    50                  55                  60

Glu Trp Met Gly Ile Ile His Pro Gly Ala Ser Asp Thr Arg Tyr Ser
65                  70                  75                  80

Pro Ser Phe Gln Gly Gln Val Thr Ile Ser Ala Asp Asn Ser Asn Ser
                85                  90                  95

Ala Thr Tyr Leu Gln Trp Ser Ser Leu Lys Ala Ser Asp Thr Ala Met
            100                 105                 110

Tyr Phe Cys Ala Arg Gln Arg Glu Leu Asp Tyr Phe Asp Tyr Trp Gly
        115                 120                 125

Gln Gly Thr Leu Val Thr Val Ser Ser
    130                 135
```

<210> SEQ ID NO 17
<211> LENGTH: 378
<212> TYPE: DNA
<213> ORGANISM: Homo Sapiens

<400> SEQUENCE: 17

```
atgtcgccat cacaactcat tgggtttctg ctgctctggg ttccagcctc cagggggtgaa     60
attgtgctga ctcagtctcc agactttcag tctgtgactc caaaggagaa agtcaccatc     120
acctgccggg ccagtcagag cattggtagt agcttacact ggtaccagca gaaaccagat     180
cagtctccaa agctcctcat caagtatgct tcccagtcct tctcaggggt cccctcgagg     240
ttcagtggca gtggatctgg gacagatttc accctcacca tcaatagcct ggaagctgaa     300
gatgctgcag cgtattactg tcatcagagt agtagtttac ctctcacttt cggcggaggg     360
accaaggtgg agatcaaa                                                    378
```

<210> SEQ ID NO 18
<211> LENGTH: 126
<212> TYPE: PRT
<213> ORGANISM: Homo sapiens

<400> SEQUENCE: 18

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Leu Thr Phe Gly Gly Gly Thr Lys Val Glu Ile Lys
        115                 120                 125

<210> SEQ ID NO 19
<211> LENGTH: 1407
<212> TYPE: DNA
<213> ORGANISM: Homo Sapiens

<400> SEQUENCE: 19
atggagtttg ggctgagctg ggtcttcctc gttgctcttt taagaggtgt ccagtgtcag      60
gtgcagctgg tggagtctgg gggaggcgtg gtccagcctg ggaggtccct gagactctcc     120
tgtgcagcgt ctggattcac cttcagcaac tatggcatgc actgggtccg ccaggctcca     180 ggcaagggc tggagtgggt ggcaggcatt tggaatgatg aattaataa ataccatgca       240 cactccgtga gggcgcgatt caccatctcc agagacaatt ccaagaacac gctgtatctg     300
caaatgaaca gcccgagagc cgaggacacg gctgtgtatt actgtgcgag agcacggtct     360
ttcgactggc tattatttga gttctggggc cagggaaccc tggtcaccgt ctctagtgcc     420
tccaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggatgagctg     1140 accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260

```
gactccgacg gctccttctt cctctatagc aagctcaccg tggacaagag caggtggcag    1320
caggggaacg tcttctcatg ctccgtgatg catgaggctc tgcacaacca ctacacgcag    1380
aagagcctct ccctgtctcc gggtaaa                                        1407
```

<210> SEQ ID NO 20
<211> LENGTH: 469
<212> TYPE: PRT
<213> ORGANISM: Homo sapiens

<400> SEQUENCE: 20

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Gly Ile Trp Asn Asp Gly Ile Asn Lys Tyr His Ala
65                  70                  75                  80

His Ser Val Arg Gly Arg Phe Thr Ile Ser Arg Asp Asn Ser Lys Asn
                85                  90                  95

Thr Leu Tyr Leu Gln Met Asn Ser Pro Arg Ala Glu Asp Thr Ala Val
            100                 105                 110

Tyr Tyr Cys Ala Arg Ala Arg Ser Phe Asp Trp Leu Leu Phe Glu Phe
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350
```

```
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
        370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
            405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 21
<211> LENGTH: 1395
<212> TYPE: DNA
<213> ORGANISM: Homo sapiens

<400> SEQUENCE: 21
atggagtttg ggctgagctg ggtcttcctc gttgctcttt taagaggtgt ccagtgtcag      60
gtgcagctgg tggagtctgg gggaggcgtg gtccagcctg gaggtccct gagactctcc     120 tgtgcagcgt ctggattcac cttcagcaac tatggcatgc actgggtccg ccaggctcca     180
ggcaaggggc tggagtgggt ggcaggcatt tggaatgatg gaattaataa ataccatgca     240
cactccgtga ggggccgatt caccatctcc agagacaatt ccaagaacac gctgtatctg     300
caaatgaaca gcccgagagc cgaggacacg gctgtgtatt actgtgcgag agcacggtct     360
ttcgactggc tattatttga gttctggggc cagggaaccc tggtcaccgt ctctagtgcc     420
tccaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600
ctctactccc tcagcagcgt ggtgaccgtg ccctccagca cttcggcac ccagacctac     660 acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
ccccgagaac acaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaa                                                    1395
```

<210> SEQ ID NO 22
<211> LENGTH: 465
<212> TYPE: PRT
<213> ORGANISM: Homo sapiens

<400> SEQUENCE: 22

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Asn Tyr Gly Met His Trp Val Arg Gln Ala Pro Gly Lys Gly Leu
    50                  55                  60

Glu Trp Val Ala Gly Ile Trp Asn Asp Gly Ile Asn Lys Tyr His Ala
65                  70                  75                  80

His Ser Val Arg Gly Arg Phe Thr Ile Ser Arg Asp Asn Ser Lys Asn
                85                  90                  95

Thr Leu Tyr Leu Gln Met Asn Ser Pro Arg Ala Glu Asp Thr Ala Val
            100                 105                 110

Tyr Tyr Cys Ala Arg Ala Arg Ser Phe Asp Trp Leu Leu Phe Glu Phe
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
            405                 410                 415

Asp Ser Asp Gly Ser Phe Phe Leu Tyr Ser Lys Leu Thr Val Asp Lys
        420                 425                 430

Ser Arg Trp Gln Gln Gly Asn Val Phe Ser Cys Ser Val Met His Glu
    435                 440                 445

Ala Leu His Asn His Tyr Thr Gln Lys Ser Leu Ser Leu Ser Pro Gly
    450                 455                 460

Lys
465

<210> SEQ ID NO 23
<211> LENGTH: 1398
<212> TYPE: DNA
<213> ORGANISM: homo sapiens

<400> SEQUENCE: 23
atggagtttg ggctgagctg ggtcttcctc gttgctcttt taagaggtgt ccagtgtcag      60
gtgcagctgg tggagtctgg gggaggcgtg gtccagcctg gaggtccct gagactctcc      120 tgtgcagcgt ctggattcac cttcagcaac tatggcatgc actgggtccg ccaggctcca      180
ggcaaggggc tggagtgggt ggcaggcatt tggaatgatg aattaataa ataccatgca      240 cactccgtga ggggccgatt caccatctcc agagacaatt ccaagaacac gctgtatctg      300
caaatgaaca gcccgagagc cgaggacacg gctgtgtatt actgtgcgag agcacggtct      360
ttcgactggc tattatttga gttctggggc cagggaaccc tggtcaccgt ctctagtgcc      420
agcaccaagg ggccatccgt cttccccctg gcgccctgct ccaggagcac ctccgagagc      480
acagccgccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac gaagacctac      660
acctgcaacg tagatcacaa gcccagcaac accaaggtgg acaagagagt tgagtccaaa      720
tatggtcccc catgcccatc atgcccagca cctgagttcc tggggggacc atcagtcttc      780
ctgttccccc caaaacccaa ggacactctc atgatctccc ggacccctga ggtcacgtgc      840
gtggtggtgg acgtgagcca ggaagacccc gaggtccagt tcaactggta cgtggatggc      900
gtggaggtgc ataatgccaa gacaaagccg cgggaggagc agttcaacag cacgtaccgt      960
gtggtcagcg tcctcaccgt cctgcaccag gactggctga acggcaagga gtacaagtgc     1020
aaggtctcca acaaaggcct cccgtcctcc atcgagaaaa ccatctccaa agccaaaggg     1080
cagccccgag agccacaggt gtacaccctg cccccatccc aggaggagat gaccaagaac     1140
caggtcagcc tgacctgcct ggtcaaaggc ttctacccca gcgacatcgc cgtggagtgg     1200
gagagcaatg ggcagccgga gaacaactac aagaccacgc ctcccgtgct ggactccgac     1260
ggctccttct tcctctacag caggctaacc gtgacaaga gcaggtggca ggaggggaat     1320
gtcttctcat gctccgtgak gcatgaggct ctgcacaacc actacacaca gaagagcctc     1380
tccctgtctc tgggtaaa                                                   1398

<210> SEQ ID NO 24
<211> LENGTH: 466
<212> TYPE: PRT
<213> ORGANISM: Homo sapiens
```

```
<400> SEQUENCE: 24

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Gly Ile Trp Asn Asp Gly Ile Asn Lys Tyr His Ala
65                  70                  75                  80

His Ser Val Arg Gly Arg Phe Thr Ile Ser Arg Asp Asn Ser Lys Asn
                85                  90                  95

Thr Leu Tyr Leu Gln Met Asn Ser Pro Arg Ala Glu Asp Thr Ala Val
            100                 105                 110

Tyr Tyr Cys Ala Arg Ala Arg Ser Phe Asp Trp Leu Leu Phe Glu Phe
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Glu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415
```

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 25
<211> LENGTH: 1407
<212> TYPE: DNA
<213> ORGANISM: Homo Sapiens

<400> SEQUENCE: 25

```
atggagtttg ggctgagctg ggttttcctc gttgctcttt taagaggtgt ccagtgtcag    60
gtgcagctgg tggagtctgg gggaggcgtg gtccagcctg gaggtccct  gagactctcc   120
tgtgcagtgt ctggattcac cttcagtaac tatggcatgc actgggtccg ccaggctcca   180
ggcaagggc  tggagtgggt ggcagctata tggaatgatg agaaaataa  acaccatgca   240
ggctccgtga ggggccgatt caccatctcc agagacaatt ccaagaacac gctgtatctg   300
caaatgaaca gcctgagagc cgaggacacg gctgtgtatt actgtgcgag aggacgatat   360
tttgactggt tattatttga gtattgggc  cagggaaccc tggtcaccgt ctctagtgcc   420
tccaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttccccc  aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagccgc gggaggagca gtacaacagc   960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggatgagctg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctatagc aagctcaccg tggacaagag caggtggcag  1320
caggggaacg tcttctcatg ctccgtgatg catgaggctc tgcacaacca ctacacgcag  1380
aagagcctct ccctgtctcc gggtaaa                                      1407
```

<210> SEQ ID NO 26
<211> LENGTH: 469
<212> TYPE: PRT
<213> ORGANISM: Homo sapiens

<400> SEQUENCE: 26

Met Glu Phe Gly Leu Ser Trp Val Phe Leu Val Ala Leu Leu Arg Gly
1               5                   10                  15

```
Val Gln Cys Gln Val Gln Leu Val Glu Ser Gly Gly Val Val Gln
            20                  25                  30

Pro Gly Arg Ser Leu Arg Leu Ser Cys Ala Val Ser Gly Phe Thr Phe
                35                  40                  45

Ser Asn Tyr Gly Met His Trp Val Arg Gln Ala Pro Gly Lys Gly Leu
 50                  55                  60

Glu Trp Val Ala Ala Ile Trp Asn Asp Gly Glu Asn Lys His His Ala
 65                  70                  75                  80

Gly Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Arg Gly Arg Tyr Phe Asp Trp Leu Leu Phe Glu Tyr
                115                 120                 125

Trp Gly Gln Gly Thr Leu Val Thr Val Ser Ser Ala Ser Thr Lys Gly
                130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
 210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
 290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445
```

Val Met His Glu Ala Leu His Asn His Tyr Thr Gln Lys Ser Leu Ser
    450                 455                 460

Leu Ser Pro Gly Lys
465

<210> SEQ ID NO 27
<211> LENGTH: 1395
<212> TYPE: DNA
<213> ORGANISM: Homo sapiens

<400> SEQUENCE: 27

| | | | | | | |
|---|---|---|---|---|---|---|
| atggagtttg | ggctgagctg | ggttttcctc | gttgctcttt | taagaggtgt | ccagtgtcag | 60 |
| gtgcagctgg | tggagtctgg | gggaggcgtg | gtccagcctg | gaggtccct | gagactctcc | 120 |
| tgtgcagtgt | ctggattcac | cttcagtaac | tatggcatgc | actgggtccg | ccaggctcca | 180 |
| ggcaaggggc | tggagtgggt | ggcagctata | tggaatgatg | agaaaataa | acaccatgca | 240 |
| ggctccgtga | ggggccgatt | caccatctcc | agagacaatt | ccaagaacac | gctgtatctg | 300 |
| caaatgaaca | gcctgagagc | cgaggacacg | gctgtgtatt | actgtgcgag | aggacgatat | 360 |
| tttgactggt | tattatttga | gtattggggc | cagggaaccc | tggtcaccgt | ctctagtgcc | 420 |
| tccaccaagg | gcccatcggt | cttccccctg | gcgccctgct | ccaggagcac | ctccgagagc | 480 |
| acagcggccc | tgggctgcct | ggtcaaggac | tacttcccg | aaccggtgac | ggtgtcgtgg | 540 |
| aactcaggcg | ctctgaccag | cggcgtgcac | accttcccag | ctgtcctaca | gtcctcagga | 600 |
| ctctactccc | tcagcagcgt | ggtgaccgtg | ccctccagca | acttcggcac | ccagacctac | 660 |
| acctgcaacg | tagatcacaa | gcccagcaac | accaaggtgg | acaagacagt | tgagcgcaaa | 720 |
| tgttgtgtcg | agtgcccacc | gtgcccagca | ccacctgtgg | caggaccgtc | agtcttcctc | 780 |
| ttccccccaa | aacccaagga | caccctcatg | atctcccgga | cccctgaggt | cacgtgcgtg | 840 |
| gtggtggacg | tgagccacga | agaccccgag | gtccagttca | actggtacgt | ggacggcgtg | 900 |
| gaggtgcata | atgccaagac | aaagccacgg | gaggagcagt | tcaacagcac | gttccgtgtg | 960 |
| gtcagcgtcc | tcaccgttgt | gcaccaggac | tggctgaacg | gcaaggagta | caagtgcaag | 1020 |
| gtctccaaca | aaggcctccc | agcccccatc | gagaaaacca | tctccaaaac | caaagggcag | 1080 |
| ccccgagaac | cacaggtgta | caccctgccc | ccatcccggg | aggagatgac | caagaaccag | 1140 |
| gtcagcctga | cctgcctggt | caaaggcttc | taccccagcg | acatcgccgt | ggagtgggag | 1200 |
| agcaatgggc | agccggagaa | caactacaag | accacacctc | ccatgctgga | ctccgacggc | 1260 |
| tccttcttcc | tctacagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaa | | | | | 1395 |

<210> SEQ ID NO 28
<211> LENGTH: 465
<212> TYPE: PRT
<213> ORGANISM: Homo sapiens

<400> SEQUENCE: 28

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Val Ser Gly Phe Thr Phe
        35                  40                  45

```
Ser Asn Tyr Gly Met His Trp Val Arg Gln Ala Pro Gly Lys Gly Leu
     50                  55                  60
Glu Trp Val Ala Ala Ile Trp Asn Asp Gly Glu Asn Lys His His Ala
 65                  70                  75                  80
Gly Ser Val Arg Gly Arg Phe Thr Ile Ser Arg Asp Asn Ser Lys Asn
                 85                  90                  95
Thr Leu Tyr Leu Gln Met Asn Ser Leu Arg Ala Glu Asp Thr Ala Val
                100                 105                 110
Tyr Tyr Cys Ala Arg Gly Arg Tyr Phe Asp Trp Leu Leu Phe Glu Tyr
            115                 120                 125
Trp Gly Gln Gly Thr Leu Val Thr Val Ser Ser Ala Ser Thr Lys Gly
        130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Asn Phe Gly Thr Gln Thr Tyr Thr Cys Asn Val
210                 215                 220
Asp His Lys Pro Ser Asn Thr Lys Val Asp Lys Thr Val Glu Arg Lys
225                 230                 235                 240
Cys Cys Val Glu Cys Pro Pro Cys Pro Ala Pro Pro Val Ala Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Gln Phe Asn Trp Tyr Val Asp Gly Val Glu Val His Asn
290                 295                 300
Ala Lys Thr Lys Pro Arg Glu Glu Gln Phe Asn Ser Thr Phe Arg Val
305                 310                 315                 320
Val Ser Val Leu Thr Val Val His Gln Asp Trp Leu Asn Gly Lys Glu
                325                 330                 335
Tyr Lys Cys Lys Val Ser Asn Lys Gly Leu Pro Ala Pro Ile Glu Lys
            340                 345                 350
Thr Ile Ser Lys Thr Lys Gly Gln Pro Arg Glu Pro Gln Val Tyr Thr
        355                 360                 365
Leu Pro Pro Ser Arg Glu Glu Met Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Met Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
450                 455                 460

Lys
465
```

<210> SEQ ID NO 29
<211> LENGTH: 1398
<212> TYPE: DNA
<213> ORGANISM: Homo sapiens

<400> SEQUENCE: 29

```
atggagtttg ggctgagctg ggttttcctc gttgctcttt taagaggtgt ccagtgtcag    60
gtgcagctgg tggagtctgg gggaggcgtg gtccagcctg ggaggtccct gagactctcc   120
tgtgcagtgt ctggattcac cttcagtaac tatggcatgc actgggtccg ccaggctcca   180
ggcaaggggc tggagtgggt ggcagctata tggaatgatg gagaaaataa acaccatgca   240
ggctccgtga ggggccgatt caccatctcc agagacaatt ccaagaacac gctgtatctg   300
caaatgaaca gcctgagagc cgaggacacg gctgtgtatt actgtgcgag aggacgatat   360
tttgactggt tattatttga gtattggggc cagggaaccc tggtcaccgt ctctagtgcc   420
agcaccaagg ggccatccgt cttccccctg gcgccctgct ccaggagcac ctccgagagc   480
acagccgccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac gaagacctac   660
acctgcaacg tagatcacaa gcccagcaac accaaggtgg acaagagagt tgagtccaaa   720
tatggtcccc catgcccatc atgcccagca cctgagttcc tggggggacc atcagtcttc   780
ctgttccccc caaaacccaa ggacactctc atgatctccc ggaccccktga ggtcacgtgc   840
gtggtggtgg acgtgagcca ggaagacccc gaggtccagt tcaactggta cgtggatggc   900
gtggaggtgc ataatgccaa gacaaagccg cgggaggagc agttcaacag cacgtaccgt   960
gtggtcagcg tcctcaccgt cctgcaccag gactggctga acggcaagga gtacaagtgc  1020
aaggtctcca acaaaggcct cccgtcctcc atcgagaaaa ccatctccaa agccaaaggg  1080
cagccccgag agccacaggt gtacaccctg cccccatccc aggaggagat gaccaagaac  1140
caggtcagcc tgacctgcct ggtcaaaggc ttctacccca gcgacatcgc cgtggagtgg  1200
gagagcaatg ggcagccgga gaacaactac aagaccacgc ctcccgtgct ggactccgac  1260
ggctccttct tcctctacag caggctaacc gtgracaaga gcaggtggca ggaggggaat  1320
gtcttctcat gctccgtgak gcatgaggct ctgcacaacc actacacaca gaagagcctc  1380
tccctgtctc tgggtaaa                                                1398
```

<210> SEQ ID NO 30
<211> LENGTH: 466
<212> TYPE: PRT
<213> ORGANISM: Homo sapiens

<400> SEQUENCE: 30

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Val Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Ala Ile Trp Asn Asp Gly Glu Asn Lys His His Ala
65                  70                  75                  80
```

-continued

Gly Ser Val Arg Gly Arg Phe Thr Ile Ser Arg Asp Asn Ser Lys Asn
            85                  90                  95

Thr Leu Tyr Leu Gln Met Asn Ser Leu Arg Ala Glu Asp Thr Ala Val
            100                 105                 110

Tyr Tyr Cys Ala Arg Gly Arg Tyr Phe Asp Trp Leu Leu Phe Glu Tyr
            115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Glu Gly Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
    275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
            435                 440                 445

Glu Ala Leu His Asn His Tyr Thr Gln Lys Ser Leu Ser Leu Ser Leu
    450                 455                 460

Gly Lys
465

<210> SEQ ID NO 31
<211> LENGTH: 1401
<212> TYPE: DNA
<213> ORGANISM: Homo Sapiens

```
<400> SEQUENCE: 31
atggggtcaa ccgccatcct cgccctcctc ctggctgttc tccaaggagt ctgtgccgag      60
gtgcagctga tgcagtctgg agcagaggtg aaaaagcccg gggagtctct gaagatctcc     120
tgtaagggtt ctggatacag cttttccttc cactggatcg cctgggtgcg ccagatgccc     180
gggaaaggcc tggagtggat ggggatcatc atcctggtg cctctgatac agatacagc       240
ccgtccttcc aaggccaggt caccatctca gccgacaact ccaacagcgc cacctacctg     300
cagtggagca gcctgaaggc ctcggacacc gccatgtatt tctgtgcgag acaaagggaa     360
ctcgactact ttgactactg gggccaggga accctggtca ccgtctctag tgcctccacc     420
aagggcccat cggtcttccc cctggcaccc tcctccaaga gcacctctgg ggcacagcg      480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720
gacaaaactc acacatgccc accgtgccca gcacctgaac tcctgggggg accgtcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggatga gctgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca agagcaggtg gcagcagggg    1320
aacgtcttct catgctccgt gatgcatgag gctctgcaca accactacac gcagaagagc    1380
ctctccctgt ctccgggtaa a                                              1401

<210> SEQ ID NO 32
<211> LENGTH: 467
<212> TYPE: PRT
<213> ORGANISM: Homo sapiens

<400> SEQUENCE: 32

Met Gly Ser Thr Ala Ile Leu Ala Leu Leu Ala Val Leu Gln Gly
1               5                   10                  15

Val Cys Ala Glu Val Gln Leu Met Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Ser Phe His Trp Ile Ala Trp Val Arg Gln Met Pro Gly Lys Gly Leu
    50                  55                  60

Glu Trp Met Gly Ile Ile His Pro Gly Ala Ser Asp Thr Arg Tyr Ser
65                  70                  75                  80

Pro Ser Phe Gln Gly Gln Val Thr Ile Ser Ala Asp Asn Ser Asn Ser
                85                  90                  95

Ala Thr Tyr Leu Gln Trp Ser Ser Leu Lys Ala Ser Asp Thr Ala Met
            100                 105                 110
```

```
Tyr Phe Cys Ala Arg Gln Arg Glu Leu Asp Tyr Phe Asp Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
                290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
450                 455                 460

Pro Gly Lys
465

<210> SEQ ID NO 33
<211> LENGTH: 1389
<212> TYPE: DNA
<213> ORGANISM: Homo sapiens

<400> SEQUENCE: 33
atggggtcaa ccgccatcct cgccctcctc ctggctgttc tccaaggagt ctgtgccgag      60
gtgcagctga tgcagtctgg agcagaggtg aaaaagcccg ggagtctctg aagatctcc     120
```

-continued

```
tgtaagggtt ctggatacag cttttccttc cactggatcg cctgggtgcg ccagatgccc      180
gggaaaggcc tggagtggat ggggatcatc catcctggtg cctctgatac cagatacagc      240
ccgtccttcc aaggccaggt caccatctca gccgacaact ccaacagcgc cacctacctg      300
cagtggagca gcctgaaggc ctcggacacc gccatgtatt tctgtgcgag acaaagggaa      360
ctcgactact ttgactactg gggccaggga accctggtca ccgtctctag tgcctccacc      420
aagggcccat cggtcttccc cctggcgccc tgctccagga gcacctccga gagcacagcg      480
gccctgggct gcctggtcaa ggactacttc cccgaaccgg tgacggtgtc gtggaactca      540
ggcgctctga ccagcggcgt gcacaccttc ccagctgtcc tacagtcctc aggactctac      600
tccctcagca gcgtggtgac cgtgccctcc agcaacttcg gcacccagac ctacacctgc      660
aacgtagatc acaagcccag caacaccaag gtggacaaga cagttgagcg caaatgttgt      720
gtcgagtgcc caccgtgccc agcaccacct gtggcaggac cgtcagtctt cctcttcccc      780
ccaaaaccca aggacaccct catgatctcc cggacccctg aggtcacgtg cgtggtggtg      840
gacgtgagcc acgaagaccc cgaggtccag ttcaactggt acgtggacgg cgtggaggtg      900
cataatgcca agacaaagcc acgggaggag cagttcaaca gcacgttccg tgtggtcagc      960
gtcctcaccg ttgtgcacca ggactggctg aacggcaagg agtacaagtg caaggtctcc     1020
aacaaaggcc tcccagcccc catcgagaaa accatctcca aaaccaaagg cagcccccga     1080
gaaccacagg tgtacaccct gcccccatcc cgggaggaga tgaccaagaa ccaggtcagc     1140
ctgacctgcc tggtcaaagg cttctacccc agcgacatcg ccgtggagtg ggagagcaat     1200
gggcagccgg agaacaacta caagaccaca cctcccatgc tggactccga cggctccttc     1260
ttcctctaca gcaagctcac cgtggacaag agcaggtggc agcaggggaa cgtcttctca     1320
tgctccgtga tgcatgaggc tctgcacaac cactacacgc agaagagcct ctccctgtct     1380
ccgggtaaa                                                              1389
```

<210> SEQ ID NO 34
<211> LENGTH: 463
<212> TYPE: PRT
<213> ORGANISM: Homo sapiens

<400> SEQUENCE: 34

```
Met Gly Ser Thr Ala Ile Leu Ala Leu Leu Leu Ala Val Leu Gln Gly
1               5                   10                  15

Val Cys Ala Glu Val Gln Leu Met Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Ser Phe His Trp Ile Ala Trp Val Arg Gln Met Pro Gly Lys Gly Leu
    50                  55                  60

Glu Trp Met Gly Ile Ile His Pro Gly Ala Ser Asp Thr Arg Tyr Ser
65                  70                  75                  80

Pro Ser Phe Gln Gly Gln Val Thr Ile Ser Ala Asp Asn Ser Asn Ser
                85                  90                  95

Ala Thr Tyr Leu Gln Trp Ser Ser Leu Lys Ala Ser Asp Thr Ala Met
            100                 105                 110

Tyr Phe Cys Ala Arg Gln Arg Glu Leu Asp Tyr Phe Asp Tyr Trp Gly
        115                 120                 125

Gln Gly Thr Leu Val Thr Val Ser Ser Ala Ser Thr Lys Gly Pro Ser
    130                 135                 140
```

```
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 35
<211> LENGTH: 1392
<212> TYPE: DNA
<213> ORGANISM: Homo sapiens

<400> SEQUENCE: 35 atgggtcaa ccgccatcct cgccctcctc ctggctgttc tccaaggagt ctgtgccgag    60
gtgcagctga tgcagtctgg agcagaggtg aaaaagcccg ggagtctct gaagatctcc   120 tgtaagggtt ctggatacag cttttccttc actggatcg cctgggtgcg ccagatgccc   180
gggaaaggcc tggagtggat ggggatcatc atcctggtg cctctgatac agatacagc    240 ccgtccttcc aaggccaggt caccatctca gccgacaact ccaacagcgc cacctacctg   300
cagtggagca gcctgaaggc ctcggacacc gccatgtatt tctgtgcgag acaaagggaa   360
```

```
ctcgactact tgactactg gggccaggga accctggtca ccgtctctag tgccagcacc   420
aaggggccat ccgtcttccc cctggcgccc tgctccagga gcacctccga gagcacagcc   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcagcttgg gcacgaagac ctacacctgc   660
aacgtagatc acaagcccag caacaccaag gtggacaaga gagttgagtc caaatatggt   720
cccccatgcc catcatgccc agcacctgag ttcctggggg gaccatcagt cttcctgttc   780
cccccaaaac ccaaggacac tctcatgatc tcccggaccc ctgaggtcac gtgcgtggtg   840
gtggacgtga gccaggaaga ccccgaggtc cagttcaact ggtacgtgga tggcgtggag   900
gtgcataatg ccaagacaaa gccgcgggag gagcagttca acagcacgta ccgtgtggtc   960
agcgtcctca ccgtcctgca ccaggactgg ctgaacggca aggagtacaa gtgcaaggtc  1020
tccaacaaag gcctcccgtc ctccatcgag aaaaccatct ccaaagccaa agggcagccc  1080
cgagagccac aggtgtacac cctgccccca tcccaggagg agatgaccaa gaaccaggtc  1140
agcctgacct gcctggtcaa aggcttctac cccagcgaca tcgccgtgga gtgggagagc  1200
aatgggcagc cggagaacaa ctacaagacc acgcctcccg tgctggactc cgacggctcc  1260
ttcttcctct acagcaggct aaccgtgrac aagagcaggt ggcaggaggg gaatgtcttc  1320
tcatgctccg tgakgcatga ggctctgcac aaccactaca cacagaagag cctctccctg  1380
tctctgggta aa                                                      1392

<210> SEQ ID NO 36
<211> LENGTH: 464
<212> TYPE: PRT
<213> ORGANISM: Homo sapiens

<400> SEQUENCE: 36

Met Gly Ser Thr Ala Ile Leu Ala Leu Leu Ala Val Leu Gln Gly
1               5                   10                  15

Val Cys Ala Glu Val Gln Leu Met Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Ser Phe His Trp Ile Ala Trp Val Arg Gln Met Pro Gly Lys Gly Leu
    50                  55                  60

Glu Trp Met Gly Ile Ile His Pro Gly Ala Ser Asp Thr Arg Tyr Ser
65                  70                  75                  80

Pro Ser Phe Gln Gly Gln Val Thr Ile Ser Ala Asp Asn Ser Asn Ser
                85                  90                  95

Ala Thr Tyr Leu Gln Trp Ser Ser Leu Lys Ala Ser Asp Thr Ala Met
            100                 105                 110

Tyr Phe Cys Ala Arg Gln Arg Glu Leu Asp Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190
```

```
Val Leu Gln Ser Ser Gly Leu Tyr Ser Leu Ser Ser Val Val Thr Val
        195                 200                 205
Pro Ser Ser Leu Gly Thr Lys Thr Tyr Thr Cys Asn Val Asp His
    210                 215                 220
Lys Pro Ser Asn Thr Lys Val Asp Lys Arg Val Glu Ser Lys Tyr Gly
225                 230                 235                 240
Pro Pro Cys Pro Ser Cys Pro Ala Pro Glu Phe Glu Gly Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser Gln Glu Asp Pro
        275                 280                 285
Glu Val Gln Phe Asn Trp Tyr Val Asp Gly Val Glu Val His Asn Ala
    290                 295                 300
Lys Thr Lys Pro Arg Glu Glu Gln Phe Asn Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Gly Leu Pro Ser Ser Ile Glu Lys Thr
            340                 345                 350
Ile Ser Lys Ala Lys Gly Gln Pro Arg Glu Pro Gln Val Tyr Thr Leu
        355                 360                 365
Pro Pro Ser Gln Glu Glu Met Thr Lys Asn Gln Val Ser Leu Thr Cys
    370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Arg Leu Thr Val Asp Lys Ser
            420                 425                 430
Arg Trp Gln Glu Gly Asn Val Phe Ser Cys Ser Val Met His Glu Ala
        435                 440                 445
Leu His Asn His Tyr Thr Gln Lys Ser Leu Ser Leu Ser Leu Gly Lys
    450                 455                 460

<210> SEQ ID NO 37
<211> LENGTH: 705
<212> TYPE: DNA
<213> ORGANISM: Homo Sapiens

<400> SEQUENCE: 37
atggaagccc cagctcagct tctcttcctc ctgctactct ggctcccaga taccaccgga      60
gaaattgtgt tgacacagtc tccagccacc ctgtctttgt ctccagggga agagccacc     120 ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaact ggcctccgct cacttttcggc     360 ggagggacca aggtggagat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca aagcagacta cgagaaacac aaagtctacg cctgcgaagt cacccatcag     660
```

```
ggcctgagct cgcccgtcac aaagagcttc aacagggag agtgt              705
```

<210> SEQ ID NO 38
<211> LENGTH: 235
<212> TYPE: PRT
<213> ORGANISM: Homo sapiens

<400> SEQUENCE: 38

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 39
<211> LENGTH: 699
<212> TYPE: DNA
<213> ORGANISM: Homo Sapiens

<400> SEQUENCE: 39

```
atgtcgccat acaactcat tgggtttctg ctgctctggg ttccagcctc cagggggtgaa      60 attgtgctga ctcagtctcc agactttcag tctgtgactc caaaggagaa agtcaccatc     120
acctgccggg ccagtcagag cattggtagt agcttacact ggtaccagca gaaaccagat     180
cagtctccaa agctcctcat caagtatgct tcccagtcct tctcaggggt cccctcgagg     240
ttcagtggca gtggatctgg gacagatttc acccctcacca tcaatagcct ggaagctgaa     300
gatgctgcag cgtattactg tcatcagagt agtagtttac ctctcacttt cggcggaggg     360
accaaggtgg agatcaaacg aactgtggct gcaccatctg tcttcatctt cccgccatct     420
gatgagcagt tgaaatctgg aactgcctct gttgtgtgcc tgctgaataa cttctatccc     480
```

```
agagaggcca aagtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgt                           699
```

<210> SEQ ID NO 40
<211> LENGTH: 233
<212> TYPE: PRT
<213> ORGANISM: Homo sapiens

<400> SEQUENCE: 40

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 41
<211> LENGTH: 5
<212> TYPE: PRT
<213> ORGANISM: Homo sapiens

<400> SEQUENCE: 41

```
Leu Ser Asp Ile Ala
1               5
```

<210> SEQ ID NO 42
<211> LENGTH: 4
<212> TYPE: PRT
<213> ORGANISM: Homo sapiens

<400> SEQUENCE: 42

Val Ile Asp Glu
1

<210> SEQ ID NO 43
<211> LENGTH: 4
<212> TYPE: PRT
<213> ORGANISM: Homo sapiens

<400> SEQUENCE: 43

Thr Cys Phe Ala
1

<210> SEQ ID NO 44
<211> LENGTH: 24
<212> TYPE: DNA
<213> ORGANISM: Artifical sequence
<220> FEATURE:
<223> OTHER INFORMATION: Synthetic
<220> FEATURE:
<223> OTHER INFORMATION: oligonucleotide primer for PCR
<220> FEATURE:
<221> NAME/KEY: misc_feature
<222> LOCATION: (18)..(23)
<223> OTHER INFORMATION: n is a, c, t, or g

<400> SEQUENCE: 44
ggccggatag gcctccannn nnnt                                          24

<210> SEQ ID NO 45
<211> LENGTH: 26
<212> TYPE: DNA
<213> ORGANISM: Artifical sequence
<220> FEATURE:
<223> OTHER INFORMATION: Synthetic
<220> FEATURE:
<223> OTHER INFORMATION: oligonucleotide primer for PCR

<400> SEQUENCE: 45
ggacactgac atggactgaa ggagta                                        26

<210> SEQ ID NO 46
<211> LENGTH: 26
<212> TYPE: DNA
<213> ORGANISM: Artifical sequence
<220> FEATURE:
<223> OTHER INFORMATION: Synthetic
<220> FEATURE:
<223> OTHER INFORMATION: oligonucleotide primer for PCR

<400> SEQUENCE: 46
ggacactgac atggactgaa ggagta                                        26

<210> SEQ ID NO 47
<211> LENGTH: 46
<212> TYPE: DNA
<213> ORGANISM: Artifical sequence
<220> FEATURE:
<223> OTHER INFORMATION: Synthetic
<220> FEATURE:
<223> OTHER INFORMATION: oligonucleotide primer for PCR

<400> SEQUENCE: 47
cagcagaagc ttctagacca ccatgtcgcc atcacaactc attggg                  46

<210> SEQ ID NO 48
<211> LENGTH: 34
<212> TYPE: DNA
<213> ORGANISM: Artifical sequence
<220> FEATURE:

-continued

<223> OTHER INFORMATION: Synthetic
<220> FEATURE:
<223> OTHER INFORMATION: oligonucleotide primer for PCR

<400> SEQUENCE: 48
cttgtcgact caacactctc ccctgttgaa gctc        34

<210> SEQ ID NO 49
<211> LENGTH: 8
<212> TYPE: PRT
<213> ORGANISM: Artifical sequence
<220> FEATURE:
<223> OTHER INFORMATION: Synthetic
<220> FEATURE:
<223> OTHER INFORMATION: amino acid sequence encoded by 5' anti-IL-1R1
      15C4 kappa primer

<400> SEQUENCE: 49

Met Ser Pro Ser Gln Leu Ile Gly
1               5

<210> SEQ ID NO 50
<211> LENGTH: 7
<212> TYPE: PRT
<213> ORGANISM: Artifical sequence
<220> FEATURE:
<223> OTHER INFORMATION: Synthetic
<220> FEATURE:
<223> OTHER INFORMATION: amino acid sequence encoded by 3' anti-IL-1R1
      15C4 kappa primer

<400> SEQUENCE: 50

Cys Glu Gly Arg Asn Phe Ser
1               5

<210> SEQ ID NO 51
<211> LENGTH: 1409
<212> TYPE: DNA
<213> ORGANISM: Homo sapiens

<400> SEQUENCE: 51
tctagaccac catggacatc aggctcagct tagttttcct tgtccttttc ataaaaggtg     60
tccagtgtga ggtagaactg gtggagtctg ggggcggctt agtacaacct ggaaggtcca    120
tgacactctc ctgtgcagcc tcggattca ctttcagaac ctatggcatg gcctgggtcc    180
gccaggcccc aacgaagggt ctggagtggg tctcatcaat tactgctagt ggtggtacca    240
cctactatcg agactccgtg aagggccgct tcactatttt tagggataat gcaaaaagta    300
ccctatacct gcagatggac agtccgaggt ctgaggacac ggccacttat ttctgtacat    360
caatttcgga atactggggc cacggagtca tggtcaccgt ctctagtgcc tccaccaagg    420
gcccatcggt cttccccctg gcaccctcct ccaagagcac ctctgggggc acagcggccc    480
tgggctgcct ggtcaaggac tacttccccg aaccggtgac ggtgtcgtgg aactcaggcg    540
ccctgaccag cggcgtgcac accttccggg ctgtcctaca gtcctcagga ctctactccc    600
tcagcagcgt ggtgaccgtg ccctccagca gcttgggcac ccagacctac atctgcaacg    660
tgaatcacaa gcccagcaac accaaggtgg acaagaaagt tgagcccaaa tcttgtgaca    720
aaactcacac atgcccaccg tgcccagcac ctgaactcct ggggggaccg tcagtcttcc    780
tcttcccccc aaaacccaag gacaccctca tgatctcccg gacccctgag gtcacatgcg    840
tggtggtgga cgtgagccac gaagaccctg aggtcaagtt caactggtac gtggacggcg    900
tggaggtgca taatgccaag acaaagccgc gggaggagca gtacaacagc acgtaccgtg    960

```
tggtcagcgt cctcaccgtc ctgcaccagg actggctgaa tggcaaggag tacaagtgca    1020
aggtctccaa caaagccctc ccagccccca tcgagaaaac catctccaaa gccaaagggc    1080
agccccgaga accacaggtg tacaccctgc cccatcccg ggatgagctg accaagaacc     1140
aggtcagcct gacctgcctg gtcaaaggct tctatcccag cgacatcgcc gtggagtggg    1200
agagcaatgg gcagccggag aacaactaca agaccacgcc tcccgtgctg gactccgacg    1260
gctccttctt cctctatagc aagctcaccg tggacaagag caggtggcag caggggaacg    1320
tcttctcatg ctccgtgatg catgaggctc tgcacaacca ctacacgcag aagagcctct    1380
ccctgtctcc gggtaaatga taagtcgac                                      1409
```

<210> SEQ ID NO 52
<211> LENGTH: 19
<212> TYPE: DNA
<213> ORGANISM: Artifical sequence
<220> FEATURE:
<223> OTHER INFORMATION: Synthetic
<220> FEATURE:
<223> OTHER INFORMATION: oligonucleotide primer for PCR

<400> SEQUENCE: 52

```
tgaggacgct gaccacacg                                                    19
```

<210> SEQ ID NO 53
<211> LENGTH: 44
<212> TYPE: DNA
<213> ORGANISM: Artifical sequence
<220> FEATURE:
<223> OTHER INFORMATION: Synthetic
<220> FEATURE:
<223> OTHER INFORMATION: oligonucleotide primer for PCR

<400> SEQUENCE: 53

```
cagcagaaagc ttctagacca ccatggggtc aaccgccatc ctcg                       44
```

<210> SEQ ID NO 54
<211> LENGTH: 32
<212> TYPE: DNA
<213> ORGANISM: Artifical sequence
<220> FEATURE:
<223> OTHER INFORMATION: Synthetic
<220> FEATURE:
<223> OTHER INFORMATION: oligonucleotide primer for PCR

<400> SEQUENCE: 54

```
gtggaggcac tagagacggt gaccagggtt cc                                     32
```

<210> SEQ ID NO 55
<211> LENGTH: 7
<212> TYPE: PRT
<213> ORGANISM: Artifical sequence
<220> FEATURE:
<223> OTHER INFORMATION: Synthetic
<220> FEATURE:
<223> OTHER INFORMATION: amino acid sequence encoded by 5' anti-IL-1R1
      15C4 heavy chain prime

<400> SEQUENCE: 55

Met Gly Ser Thr Ala Ile Leu
1               5

<210> SEQ ID NO 56
<211> LENGTH: 11
<212> TYPE: PRT
<213> ORGANISM: Artifical sequence
<220> FEATURE:

<223> OTHER INFORMATION: Synthetic
<220> FEATURE:
<223> OTHER INFORMATION: amino acid sequence encoded by 3' anti-IL-1R1
      15C4 heavy chain prime

<400> SEQUENCE: 56

Thr Ser Ala Ser Ser Val Thr Val Leu Thr Gly
1               5                   10

<210> SEQ ID NO 57
<211> LENGTH: 1415
<212> TYPE: DNA
<213> ORGANISM: homo sapiens

<400> SEQUENCE: 57

```
tctagaccac catggacatg agggtcccccg ctcagctcct ggggctcctg ctattgtggt      60
tgagaggtgc cagatgtgag gtccagctgg tgcagtctgg gggaggcttg gtacatcctg     120
gggggtccct gagactctcc tgtgcaggct ctggattcac cttcagtggc catgctttgc     180
actgggttcg ccaggctcca ggaaaaggtc tggagtgggt atcaggtatt ggtactcatg     240
gtgggacata ctatgcagac tccgtgaagg gccgattcac catctccaga gacaatgcca     300
agaactcctt gtttcttcaa atgaacagcc tgagcgccga ggacatggct gtgtattact     360
gtacaagaag aaactgggga caatttgact actggggcca gggaaccctg gtcaccgtct     420
ctagtgcctc caccaagggc ccatcggtct tccccctggc gccctgctcc aggagcacct     480
ccgagagcac agcggccctg ggctgcctgg tcaaggacta cttccccgaa ccggtgacgg     540
tgtcgtggaa ctcaggcgct ctgaccagcg gcgtgcacac cttcccagct gtcctacagt     600
cctcaggact ctactccctc agcagcgtgg tgaccgtgcc ctcagcaac ttcggcaccc      660
agacctacac ctgcaacgta gatcacaagc ccagcaacac caaggtggac aagacagttg     720
agcgcaaatg ttgtgtcgag tgcccaccgt gcccagcacc acctgtggca ggaccgtcag     780
tcttcctctt ccccccaaaa cccaaggaca ccctcatgat ctcccggacc cctgaggtca     840
cgtgcgtggt ggtggacgtg agccacgaag accccgaggt ccagttcaac tggtacgtgg     900
acggcgtgga ggtgcataat gccaagacaa agccacggga ggagcagttc aacagcacgt     960
tccgtgtggt cagcgtcctc accgttgtgc accaggactg gctgaacggc aaggagtaca    1020
agtgcaaggt ctccaacaaa ggcctcccag ccccatcga gaaaaccatc tccaaaacca     1080
aagggcagcc ccgagaacca caggtgtaca ccctgccccc atcccgggag gagatgacca    1140
agaaccaggt cagcctgacc tgcctggtca aaggcttcta ccccagcgac atcgccgtgg    1200
agtgggagag caatgggcag ccggagaaca actacaagac cacacctccc atgctggact    1260
ccgacggctc cttcttcctc tacagcaagc tcaccgtgga cagagcagg tggcagcagg     1320
ggaacgtctt ctcatgctcc gtgatgcatg aggctctgca caaccactac acgcagaaga    1380
gcctctccct gtctccgggt aaatgataag tcgac                                1415
```

<210> SEQ ID NO 58
<211> LENGTH: 1418
<212> TYPE: DNA
<213> ORGANISM: Homo sapiens

<400> SEQUENCE: 58

```
tctagaccac catggacatg agggtcccccg ctcagctcct ggggctcctg ctattgtggt      60
tgagaggtgc cagatgtgag gtccagctgg tgcagtctgg gggaggcttg gtacatcctg     120
gggggtccct gagactctcc tgtgcaggct ctggattcac cttcagtggc catgctttgc     180
```

```
actgggttcg ccaggctcca ggaaaaggtc tggagtgggt atcaggtatt ggtactcatg       240
gtgggacata ctatgcagac tccgtgaagg gccgattcac catctccaga gacaatgcca       300
agaactcctt gtttcttcaa atgaacagcc tgagcgccga ggacatggct gtgtattact       360
gtacaagaag aaactgggga caatttgact actggggcca gggaaccctg gtcaccgtct       420
ctagtgccag caccaagggg ccatccgtct tccccctggc gccctgctcc aggagcacct       480
ccgagagcac agccgccctg gctgcctgg tcaaggacta cttccccgaa ccggtgacgg        540
tgtcgtggaa ctcaggcgcc ctgaccagcg gcgtgcacac cttcccggct gtcctacagt       600
cctcaggact ctactccctc agcagcgtgg tgaccgtgcc ctccagcagc ttgggcacga       660
agacctacac ctgcaacgta gatcacaagc ccagcaacac caaggtggac aagagagttg       720
agtccaaata tggtccccca tgcccatcat gcccagcacc tgagttcctg ggggaccat       780 cagtcttcct gttccccca aacccaagg acactctcat gatctcccgg acccctgagg         840
tcacgtgcgt ggtggtggac gtgagccagg aagaccccga ggtccagttc aactggtacg       900
tggatggcgt ggaggtgcat aatgccaaga caaagccgcg ggaggagcag ttcaacagca       960
cgtaccgtgt ggtcagcgtc ctcaccgtcc tgcaccagga ctggctgaac ggcaaggagt      1020
acaagtgcaa ggtctccaac aaaggcctcc cgtcctccat cgagaaaacc atctccaaag      1080
ccaaagggca gccccgagag ccacaggtgt acaccctgcc cccatcccag gaggagatga      1140
ccaagaacca ggtcagcctg acctgcctgg tcaaaggctt ctaccccagc gacatcgccg      1200
tggagtggga gagcaatggg cagccggaga acaactacaa gaccacgcct cccgtgctgg      1260
actccgacgg ctccttcttc ctctacagca ggctaaccgt ggacaagagc aggtggcagg      1320
aggggaatgt cttctcatgc tccgtgatgc atgaggctct gcacaaccac tacacacaga      1380
agagcctctc cctgtctctg ggtaaatgat aagtcgac                              1418
```

<210> SEQ ID NO 59
<211> LENGTH: 485
<212> TYPE: PRT
<213> ORGANISM: Homo sapiens

<400> SEQUENCE: 59

```
Met Val His Ala Thr Ser Pro Leu Leu Leu Leu Leu Leu Ser Leu
1               5                   10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
        35                  40                  45

Ser Lys Gly Glu Phe Thr Gly Thr Tyr Thr Thr Ala Val Thr Ala Thr
    50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Leu Glu
145                 150                 155                 160
```

```
Ala Asp Lys Cys Lys Glu Arg Glu Lys Ile Ile Leu Val Ser Ser
            165                 170                 175
Ala Asn Glu Ile Asp Val Arg Pro Cys Pro Leu Asn Pro Asn Glu His
            180                 185                 190
Lys Gly Thr Ile Thr Trp Tyr Lys Asp Asp Ser Lys Thr Pro Val Ser
            195                 200                 205
Thr Glu Gln Ala Ser Arg Ile His Gln His Lys Glu Lys Leu Trp Phe
            210                 215                 220
Val Pro Ala Met Val Glu Asp Ser Gly His Tyr Tyr Cys Val Val Arg
225                 230                 235                 240
Asn Ser Ser Tyr Cys Leu Arg Ile Lys Ile Ser Ala Lys Phe Val Glu
                    245                 250                 255
Asn Glu Pro Asn Leu Cys Tyr Asn Ala Gln Ala Ile Phe Lys Gln Lys
                    260                 265                 270
Leu Pro Val Ala Gly Asp Gly Gly Leu Val Cys Pro Tyr Met Glu Phe
                    275                 280                 285
Phe Lys Asn Glu Asn Asn Glu Leu Pro Lys Leu Gln Trp Tyr Lys Asp
            290                 295                 300
Cys Lys Pro Leu Leu Leu Asp Asn Ile His Phe Ser Gly Val Lys Asp
305                 310                 315                 320
Arg Leu Ile Val Met Asn Val Ala Glu Lys His Arg Gly Asn Tyr Thr
                    325                 330                 335
Cys His Ala Ser Tyr Thr Tyr Leu Gly Lys Gln Tyr Pro Ile Thr Arg
                    340                 345                 350
Val Ile Glu Phe Ile Thr Leu Glu Glu Asn Lys Pro Thr Arg Pro Val
            355                 360                 365
Ile Val Ser Pro Ala Asn Glu Thr Met Glu Val Asp Leu Gly Ser Gln
370                 375                 380
Ile Gln Leu Ile Cys Asn Val Thr Gly Gln Leu Ser Asp Ile Ala Tyr
385                 390                 395                 400
Trp Lys Trp Asn Gly Ser Val Ile Asp Glu Asp Pro Val Leu Gly
            405                 410                 415
Glu Asp Tyr Tyr Ser Val Glu Asn Pro Ala Asn Lys Arg Arg Ser Thr
            420                 425                 430
Leu Ile Thr Val Leu Asn Ile Ser Glu Ile Glu Ser Arg Phe Tyr Lys
            435                 440                 445
His Pro Phe Thr Cys Phe Ala Lys Asn Thr His Gly Ile Asp Ala Ala
            450                 455                 460
Tyr Ile Gln Leu Ile Tyr Pro Val Thr Asn Phe Gln Lys Asp Tyr Lys
465                 470                 475                 480
Asp Asp Asp Asp Lys
            485

<210> SEQ ID NO 60
<211> LENGTH: 485
<212> TYPE: PRT
<213> ORGANISM: Artifical sequence
<220> FEATURE:
<223> OTHER INFORMATION: Synthetic
<220> FEATURE:
<223> OTHER INFORMATION: avidin-cynomolgus IL-1R1-FLAG chimeric protein

<400> SEQUENCE: 60

Met Val His Ala Thr Ser Pro Leu Leu Leu Leu Leu Leu Ser Leu
1               5                   10                  15
Ala Leu Val Ala Pro Gly Leu Ser Ala Arg Lys Cys Ser Leu Thr Gly
            20                  25                  30
```

Lys Trp Thr Asn Asp Leu Gly Ser Asn Met Thr Ile Gly Ala Val Asn
         35                  40                  45

Ser Lys Gly Glu Phe Thr Gly Thr Tyr Thr Thr Ala Val Thr Ala Thr
 50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
             115                 120                 125

Asp Ile Gly Asp Asp Trp Lys Ala Thr Arg Val Gly Ile Asn Ile Phe
         130                 135                 140

Thr Arg Leu Arg Thr Gln Lys Glu Gln Leu Leu Ala Ser Leu Leu Glu
145                 150                 155                 160

Ala Asp Lys Cys Asn Glu Arg Glu Lys Ile Ile Leu Val Ser Ser
                165                 170                 175

Ala Asn Glu Ile Asp Val Arg Pro Cys Pro Leu Asn Pro Asn Glu Tyr
                180                 185                 190

Lys Gly Thr Ile Thr Trp Tyr Lys Asn Asp Ser Lys Thr Pro Ile Ser
             195                 200                 205

Thr Glu Gln Ala Ser Arg Ile His Gln His Lys Lys Lys Leu Trp Phe
         210                 215                 220

Val Pro Ala Lys Val Glu Asp Ser Gly His Tyr Tyr Cys Val Val Arg
225                 230                 235                 240

Asn Ser Ser Tyr Cys Leu Arg Ile Lys Ile Thr Ala Lys Phe Val Glu
                245                 250                 255

Asn Glu Pro Asn Leu Cys Tyr Asn Ala Glu Ala Ile Phe Lys Gln Arg
                260                 265                 270

Leu Pro Val Ala Gly Asp Gly Gly Leu Val Cys Pro Tyr Met Glu Phe
             275                 280                 285

Phe Lys Asp Glu Asn Asn Glu Leu Pro Lys Leu Leu Trp Tyr Lys Asp
         290                 295                 300

Cys Lys Pro Leu Leu Leu Asp Asn Ile His Phe Ser Gly Val Lys Asp
305                 310                 315                 320

Arg Leu Ile Val Met Asn Val Ala Glu Lys His Arg Gly Asn Tyr Thr
                325                 330                 335

Cys His Ala Ser Tyr Thr Tyr Leu Gly Lys Gln Tyr Pro Ile Thr Arg
                340                 345                 350

Val Ile Glu Phe Ile Thr Leu Glu Glu Asn Lys Pro Thr Arg Pro Val
             355                 360                 365

Ile Val Ser Pro Ala Asn Glu Thr Ile Glu Val Asp Leu Gly Ser Gln
         370                 375                 380

Ile Gln Leu Ile Cys Asn Val Thr Gly Gln Leu Ser Asp Thr Ala Tyr
385                 390                 395                 400

Trp Lys Trp Asn Gly Ser Phe Ile Asp Glu Asp Pro Val Leu Gly
                405                 410                 415

Glu Asp Tyr Tyr Ser Val Glu Asn Pro Ala Asn Lys Arg Arg Ser Thr
             420                 425                 430

Leu Ile Thr Val Leu Asn Ile Ser Glu Thr Glu Ser Arg Phe Tyr Lys
         435                 440                 445

His Pro Phe Thr Cys Leu Ala Arg Asn Thr His Gly Met Asp Ala Ala

```
                450             455             460
Tyr Val Gln Leu Ile Tyr Pro Val Thr Lys Phe Gln Lys Asp Tyr Lys
465                 470             475                 480

Asp Asp Asp Asp Lys
                485
```

<210> SEQ ID NO 61
<211> LENGTH: 5
<212> TYPE: PRT
<213> ORGANISM: Homo sapiens

<400> SEQUENCE: 61

```
Asn Tyr Gly Met His
1               5
```

<210> SEQ ID NO 62
<211> LENGTH: 8
<212> TYPE: PRT
<213> ORGANISM: Homo sapiens

<400> SEQUENCE: 62

```
Thr Phe Ser Asn Tyr Gly Met His
1               5
```

<210> SEQ ID NO 63
<211> LENGTH: 5
<212> TYPE: PRT
<213> ORGANISM: Homo sapiens

<400> SEQUENCE: 63

```
Phe His Trp Ile Ala
1               5
```

<210> SEQ ID NO 64
<211> LENGTH: 17
<212> TYPE: PRT
<213> ORGANISM: Homo sapiens

<400> SEQUENCE: 64

```
Gly Ile Trp Asn Asp Gly Ile Asn Lys Tyr His Ala His Ser Val Arg
1               5                   10                  15

Gly
```

<210> SEQ ID NO 65
<211> LENGTH: 17
<212> TYPE: PRT
<213> ORGANISM: Homo sapiens

<400> SEQUENCE: 65

```
Ala Ile Trp Asn Asp Gly Glu Asn Lys His His Ala Gly Ser Val Arg
1               5                   10                  15

Gly
```

<210> SEQ ID NO 66
<211> LENGTH: 17
<212> TYPE: PRT
<213> ORGANISM: Homo sapiens

<400> SEQUENCE: 66

```
Ile Ile His Pro Gly Ala Ser Asp Thr Arg Tyr Ser Pro Ser Phe Gln
1               5                   10                  15

Gly
```

<210> SEQ ID NO 67
<211> LENGTH: 11
<212> TYPE: PRT
<213> ORGANISM: Homo sapiens

<400> SEQUENCE: 67

Ala Arg Ser Phe Asp Trp Leu Leu Phe Glu Phe
1               5                   10

<210> SEQ ID NO 68
<211> LENGTH: 11
<212> TYPE: PRT
<213> ORGANISM: Homo sapiens

<400> SEQUENCE: 68

Gly Arg Tyr Phe Asp Trp Leu Leu Phe Glu Tyr
1               5                   10

<210> SEQ ID NO 69
<211> LENGTH: 9
<212> TYPE: PRT
<213> ORGANISM: Homo sapiens

<400> SEQUENCE: 69

Gln Arg Glu Leu Asp Tyr Phe Asp Tyr
1               5

<210> SEQ ID NO 70
<211> LENGTH: 11
<212> TYPE: PRT
<213> ORGANISM: Homo sapiens

<400> SEQUENCE: 70

Arg Ala Ser Gln Ser Val Ser Ser Tyr Leu Ala
1               5                   10

<210> SEQ ID NO 71
<211> LENGTH: 11
<212> TYPE: PRT
<213> ORGANISM: Homo sapiens

<400> SEQUENCE: 71

Arg Ala Ser Gln Ser Ile Gly Ser Ser Leu His
1               5                   10

<210> SEQ ID NO 72
<211> LENGTH: 7
<212> TYPE: PRT
<213> ORGANISM: Homo sapiens

<400> SEQUENCE: 72

Asp Ala Ser Asn Arg Ala Thr
1               5

<210> SEQ ID NO 73
<211> LENGTH: 7
<212> TYPE: PRT
<213> ORGANISM: Homo sapiens

<400> SEQUENCE: 73

Tyr Ala Ser Gln Ser Phe Ser
1               5

<210> SEQ ID NO 74
<211> LENGTH: 10

```
<212> TYPE: PRT
<213> ORGANISM: Homo sapiens

<400> SEQUENCE: 74

Gln Gln Arg Ser Asn Trp Pro Pro Leu Thr
1               5                   10

<210> SEQ ID NO 75
<211> LENGTH: 9
<212> TYPE: PRT
<213> ORGANISM: Homo sapiens

<400> SEQUENCE: 75

His Gln Ser Ser Ser Leu Pro Leu Thr
1               5

<210> SEQ ID NO 76
<211> LENGTH: 111
<212> TYPE: PRT
<213> ORGANISM: Homo sapiens

<400> SEQUENCE: 76

Pro Val Ile Val Ser Pro Ala Asn Glu Thr Met Glu Val Asp Leu Gly
1               5                   10                  15

Ser Gln Ile Gln Leu Ile Cys Asn Val Thr Gly Gln Leu Ser Asp Ile
            20                  25                  30

Ala Tyr Trp Lys Trp Asn Gly Ser Val Ile Asp Glu Asp Asp Pro Val
        35                  40                  45

Leu Gly Glu Asp Tyr Tyr Ser Val Glu Asn Pro Ala Asn Lys Arg Arg
    50                  55                  60

Ser Thr Leu Ile Thr Val Leu Asn Ile Ser Glu Ile Glu Ser Arg Phe
65                  70                  75                  80

Tyr Lys His Pro Phe Thr Cys Phe Ala Lys Asn Thr His Gly Ile Asp
                85                  90                  95

Ala Ala Tyr Ile Gln Leu Ile Tyr Pro Val Thr Asn Phe Gln Lys
            100                 105                 110

<210> SEQ ID NO 77
<211> LENGTH: 350
<212> TYPE: DNA
<213> ORGANISM: Homo sapiens

<400> SEQUENCE: 77
cctgtgattg tgagcccagc taatgagaca atggaagtag acttgggatc ccagatacaa      60
ttgatctgta atgtcaccgg ccagttgagt gacattgctt actggaagtg gaatgggtca     120
gtaattgatg aagatgaccc agtgctaggg aagactatt acagtgtgga aaatcctgca      180
aacaaaagaa ggagtaccct catcacagtg cttaatatat cggaaattga agtagatttt     240
tataaacatc catttacctg ttttgccaag aatacacatg gtagatgc agcatatatc       300 cagttaatat atccagtcac taatttccag aagcacatga ttggtatatg                350

<210> SEQ ID NO 78
<211> LENGTH: 350
<212> TYPE: DNA
<213> ORGANISM: Rattus sp.

<400> SEQUENCE: 78
cctgtgatta tgagcccacg gaatgagacg atggaagctg acccaggatc cacgatacaa      60
ctgatctgca acgtcacggg ccagttcacc gaccttgtct actggaagtg gaatgggtcg     120
```

```
gaaattgaat gggacgatcc aatcctagcc gaagactatc agttttgga acacccttca    180 gccaaaagaa agtacactct cattacaaca cttaacgttt cagaggtcaa aagccagttt    240
tatcgctatc cgttcatctg cttcgttaag aacactcata ttctggagac tgcacacgta    300
cggttagtat acccagttcc tgacttcaag aattacctca tcggggctt                350
```

<210> SEQ ID NO 79
<211> LENGTH: 111
<212> TYPE: PRT
<213> ORGANISM: Rattus Sp.

<400> SEQUENCE: 79

```
Pro Val Ile Met Ser Pro Arg Asn Glu Thr Met Glu Ala Asp Pro Gly
1               5                   10                  15

Ser Thr Ile Gln Leu Ile Cys Asn Val Thr Gly Gln Phe Thr Asp Leu
            20                  25                  30

Val Tyr Trp Lys Trp Asn Gly Ser Glu Ile Glu Trp Asp Asp Pro Ile
        35                  40                  45

Leu Ala Glu Asp Tyr Gln Phe Leu Glu His Pro Ser Ala Lys Arg Lys
    50                  55                  60

Tyr Thr Leu Ile Thr Thr Leu Asn Val Ser Glu Val Lys Ser Gln Phe
65                  70                  75                  80

Tyr Arg Tyr Pro Phe Ile Cys Phe Val Lys Asn Thr His Ile Leu Glu
                85                  90                  95

Thr Ala His Val Arg Leu Val Tyr Pro Val Pro Asp Phe Lys Lys
            100                 105                 110
```

<210> SEQ ID NO 80
<211> LENGTH: 118
<212> TYPE: PRT
<213> ORGANISM: Homo sapiens

<400> SEQUENCE: 80

```
Glu Val Gln Leu Met Gln Ser Gly Ala Glu Val Lys Lys Pro Gly Glu
1               5                   10                  15

Ser Leu Lys Ile Ser Cys Lys Gly Ser Gly Tyr Ser Phe Ser Phe His
            20                  25                  30

Trp Ile Ala Trp Val Arg Gln Met Pro Gly Lys Gly Leu Glu Trp Met
        35                  40                  45

Gly Ile Ile His Pro Gly Ala Ser Asp Thr Arg Tyr Ser Pro Ser Phe
    50                  55                  60

Gln Gly Gln Val Thr Ile Ser Ala Asp Asn Ser Asn Ser Ala Thr Tyr
65                  70                  75                  80

Leu Gln Trp Ser Ser Leu Lys Ala Ser Asp Thr Ala Met Tyr Phe Cys
                85                  90                  95

Ala Arg Gln Arg Glu Leu Asp Tyr Phe Asp Tyr Trp Gly Gln Gly Thr
            100                 105                 110

Leu Val Thr Val Ser Ser
            115
```

<210> SEQ ID NO 81
<211> LENGTH: 107
<212> TYPE: PRT
<213> ORGANISM: Homo sapiens

<400> SEQUENCE: 81

```
Glu Ile Val Leu Thr Gln Ser Pro Asp Phe Gln Ser Val Thr Pro Lys
1               5                   10                  15
```

```
Glu Lys Val Thr Ile Thr Cys Arg Ala Ser Gln Ser Ile Gly Ser Ser
             20                  25                  30

Leu His Trp Tyr Gln Gln Lys Pro Asp Gln Ser Pro Lys Leu Leu Ile
         35                  40                  45

Lys Tyr Ala Ser Gln Ser Phe Ser Gly Val Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys His Gln Ser Ser Ser Leu Pro Leu
                 85                  90                  95

Thr Phe Gly Gly Gly Thr Lys Val Glu Ile Lys
            100                 105
```

<210> SEQ ID NO 82
<211> LENGTH: 120
<212> TYPE: PRT
<213> ORGANISM: Homo sapiens

<400> SEQUENCE: 82

```
Gln Val Gln Leu Val Glu Ser Gly Gly Gly Val Val Gln Pro Gly Arg
1               5                  10                  15

Ser Leu Arg Leu Ser Cys Ala Val Ser Gly Phe Thr Phe Ser Asn Tyr
             20                  25                  30

Gly Met His Trp Val Arg Gln Ala Pro Gly Lys Gly Leu Glu Trp Val
         35                  40                  45

Ala Ala Ile Trp Asn Asp Gly Glu Asn Lys His His Ala Gly Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Tyr Phe Asp Trp Leu Leu Phe Glu Tyr Trp Gly Gln
                100                 105                 110

Gly Thr Leu Val Thr Val Ser Ser
            115                 120
```

<210> SEQ ID NO 83
<211> LENGTH: 108
<212> TYPE: PRT
<213> ORGANISM: Homo sapiens

<400> SEQUENCE: 83

```
Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Leu Thr Phe Gly Gly Gly Thr Lys Val Glu Ile Lys
                100                 105
```

```
<210> SEQ ID NO 84
<211> LENGTH: 120
<212> TYPE: PRT
<213> ORGANISM: Homo sapiens

<400> SEQUENCE: 84

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Gly Ile Trp Asn Asp Gly Ile Asn Lys Tyr His Ala His Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Pro Arg Ala Glu Asp Thr Ala Val Tyr Tyr Cys
                85                  90                  95

Ala Arg Ala Arg Ser Phe Asp Trp Leu Leu Phe Glu Phe Trp Gly Gln
            100                 105                 110

Gly Thr Leu Val Thr Val Ser Ser
        115                 120

<210> SEQ ID NO 85
<211> LENGTH: 354
<212> TYPE: DNA
<213> ORGANISM: homo sapiens

<400> SEQUENCE: 85
gaggtgcagc tgatgcagtc tggagcagag gtgaaaaagc ccggggagtc tctgaagatc      60
tcctgtaagg gttctggata cagcttttcc ttccactgga tcgcctgggt gcgccagatg    120
cccgggaaag gcctggagtg gatggggatc atccatcctg gtgcctctga taccagatac    180
agcccgtcct tccaaggcca ggtcaccatc tcagccgaca actccaacag cgccacctac    240
ctgcagtgga gcagcctgaa ggcctcggac accgccatgt atttctgtgc agacaaagg     300 gaactcgact actttgacta ctggggccag ggaaccctgg tcaccgtctc tagt          354

<210> SEQ ID NO 86
<211> LENGTH: 321
<212> TYPE: DNA
<213> ORGANISM: homo sapiens

<400> SEQUENCE: 86
gaaattgtgc tgactcagtc tccagacttt cagtctgtga ctccaaagga gaaagtcacc     60
atcacctgcc gggccagtca gagcattggt agtagcttac actggtacca gcagaaacca   120
gatcagtctc caaagctcct catcaagtat gcttcccagt ccttctcagg ggtcccctcg   180
aggttcagtg gcagtggatc tgggacagat ttcaccctca ccatcaatag cctggaagct   240
gaagatgctg cagcgtatta ctgtcatcag agtagtagtt acctctcac tttcggcgga   300 gggaccaagg tggagatcaa a                                              321

<210> SEQ ID NO 87
<211> LENGTH: 360
<212> TYPE: DNA
<213> ORGANISM: homo sapiens

<400> SEQUENCE: 87
caggtgcagc tggtggagtc tgggggaggc gtggtccagc ctggagggtc cctgagactc     60
```

-continued

```
tcctgtgcag tgtctggatt caccttcagt aactatggca tgcactgggt ccgccaggct    120
ccaggcaagg ggctggagtg ggtggcagct atatggaatg atggagaaaa taaacaccat    180
gcaggctccg tgaggggccg attcaccatc tccagagaca attccaagaa cacgctgtat    240
ctgcaaatga acagcctgag agccgaggac acggctgtgt attactgtgc gagaggacga    300
tattttgact ggttattatt tgagtattgg ggccagggaa ccctggtcac cgtctctagt    360

<210> SEQ ID NO 88
<211> LENGTH: 324
<212> TYPE: DNA
<213> ORGANISM: homo sapiens

<400> SEQUENCE: 88
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgct cactttcggc    300
ggagggacca aggtggagat caaa                                           324

<210> SEQ ID NO 89
<211> LENGTH: 360
<212> TYPE: DNA
<213> ORGANISM: homo sapiens

<400> SEQUENCE: 89
caggtgcagc tggtggagtc tgggggaggc gtggtccagc ctgggaggtc cctgagactc     60
tcctgtgcag cgtctggatt caccttcagc aactatggca tgcactgggt ccgccaggct    120
ccaggcaagg ggctggagtg ggtggcaggc atttggaatg atggaattaa taaataccat    180
gcacactccg tgaggggccg attcaccatc tccagagaca attccaagaa cacgctgtat    240
ctgcaaatga acagcccgag agccgaggac acggctgtgt attactgtgc gagagcacgg    300
tctttcgact ggctattatt tgagttctgg ggccagggaa ccctggtcac cgtctctagt    360
```

THERAPEUTIC HUMAN ANTI-IL-1R1 MONOCLONAL ANTIBODY

RELATED APPLICATIONS

This application is a continuation of and claims priority to U.S. application Ser. No. 13/450,126, filed Apr. 18, 2012, which is a continuation of U.S. application Ser. No. 12/210, 313, filed Sep. 15, 2008, now U.S. Pat. No. 8,236,559, which is a continuation of U.S. application Ser. No. 10/656,769, filed Sep. 5, 2003, now U.S. Pat. No. 7,438,910, which claims the benefit of U.S. provisional application Ser. No. 60/408, 719, filed Sep. 6, 2002. The specifications of each of the foregoing applications are incorporated herein by reference in their entirety.

FIELD OF THE INVENTION

The invention relates to antibodies that bind interleukin-1 receptor type 1 (IL-1R1) protein. Compositions, particularly pharmaceutical compositions and methods for treating of IL-1 mediated diseases, such as rheumatoid arthritis, osteoarthritis, and other inflammatory conditions, are also provided.

The instant application contains a sequence listing which has been submitted via EFS-Web and is incorporated herein by reference in its entirety. Said ASCII copy, created on Aug. 7, 2013, is named 102728-0041-104_Seq.txt, and is 113,487 bytes in size.

BACKGROUND OF THE INVENTION

Antibody Development

Inflammation is the body's response to injuries resulting from mechanical damage, infection, or antigenic stimulation. Inflammatory reactions often are expressed pathologically. Such conditions arise when the inflammation is expressed in an exaggerated manner, is inappropriately stimulated, or persists after the injurious agent is removed.

The inflammatory response is mediated, inter alia, by cytokines. One of the most potent inflammatory cytokines yet discovered is interleukin-1 (IL-1). An increase in IL-1 signaling causes persistent inflammation associated with several diseases, and IL-1 is thought to be a key mediator in many diseases and medical conditions. This cytokine is manufactured primarily (though not exclusively) by cells of the macrophage/monocyte lineage and may be produced in two forms: IL-1 alpha (IL-1α) and IL-1 beta (IL-1β).

IL-1 stimulates cellular responses by interacting with a heterodimeric receptor complex comprised of two transmembrane proteins, IL-1 receptor type I (IL-1R1) and IL-1 receptor accessory protein (IL-1RAcP). IL-1 first binds to IL-1R1; IL-1RAcP is then recruited to this complex (Greenfeder et al., 1995, *J. Biol. Chem.* 270:13757-13765; Yoon and Dinarello, 1998, *J. Immunology* 160:3170-3179; Cullinan et al., 1998, *J. Immunology* 161:5614-5620), followed by signal transduction resulting in the induction of a cellular response.

Cell-based binding studies suggest that IL-1RAcP stabilizes the IL-1R signaling complex by slowing the ligand off-rate (Wesche et al., 1998, *FEBS Letters* 429:303-306). While the interaction of the IL-1 with IL-1R has been thoroughly characterized, the interaction of IL-1RAcP with ligand-bound receptor remains poorly defined. Since IL-1RAcP has no significant affinity for either IL-1 or IL-1R1 alone, but high affinity for the complex, it follows that novel binding sites for IL-1RAcP are created by the IL-1/IL-1R binding event, which may even include contributions from IL-1 residues (Ettorre et al., 1997, *Eur. Cytokine Netw.* 8:161-171). Another molecule, IL-1 receptor antagonist (IL-1ra) competes with IL-1α and IL-1β for receptor binding but fails to recruit IL-1RAcP, resulting in an occupied but non-signaling receptor. IL-1 activity can additionally be counterbalanced by IL-1R type II, a decoy receptor that binds ligand but does not participate in signaling due to a truncated intracellular domain. IL-1ra and IL-1R type II act to reduce the severity and duration of IL-1 mediated inflammatory events (Wesche et al., 1998, *FEBS Letters* 429:303-306; Dripps et al., 1991, *J. Biol. Chem.* 266:10331-10336; Dripps et al., 1991, *J. Biol. Chem.* 266:20331-20335).

Interleukin-1 inhibitors may be produced from any protein capable of specifically preventing activation of cellular receptors to IL-1, which may result from a number of mechanisms. Such mechanisms include down-regulating IL-1 production, binding free IL-1, interfering with IL-1 binding to IL-1R, interfering with formation of the IL-1R-IL-1RAcP complex, or interfering with modulation of IL-1 signaling after binding to its receptor. Classes of IL-1 inhibitors include:

- interleukin-1 receptor antagonists such as IL-1ra, as described below;
- anti-IL-1R monoclonal antibodies (e.g., as disclosed in published European Patent Application No. EP 623674, the disclosure of which is hereby incorporated by reference);
- IL-1 binding proteins such as soluble IL-1 receptors (e.g., as disclosed in U.S. Pat. Nos. 5,492,888; 5,488,032; 5,464,937; 5,319,071; and 5,180,812; the disclosures of which are hereby incorporated by reference);
- anti-IL-1 monoclonal antibodies (e.g., as disclosed in International Patent Application Publication Nos. WO 9501997, WO 9402627, WO 9006371, U.S. Pat. No. 4,935,343, EP 364778, EP 267611 and EP 220063, the disclosures of which are hereby incorporated by reference);
- IL-1 receptor accessory proteins and antibodies thereto (e.g., as disclosed in International Patent Application Publication Nos. WO 96/23067 and WO 99/37773, the disclosure of which is hereby incorporated by reference); and
- inhibitors of interleukin-β converting enzyme (ICE) or caspase I (e.g., as disclosed in International Patent Application Publication Nos. WO 99/46248, WO 99/47545, and WO 99/47154, the disclosures of which are hereby incorporated by reference), which can be used to inhibit IL-1β production and secretion;
- interleukin-1β protease inhibitors; and
- other compounds and proteins that block in vivo synthesis or extracellular release of IL-1.

Exemplary IL-1 inhibitors are disclosed in the following references: U.S. Pat. Nos. 5,747,444; 5,359,032; 5,608,035; 5,843,905; 5,359,032; 5,866,576; 5,869,660; 5,869,315; 5,872,095; 5,955,480; and 5,965,564; International Patent Application Publication Nos WO98/21957, WO96/09323, WO91/17184, WO96/40907, WO98/32733, WO98/42325, WO98/44940, WO98/47892, WO98/56377, WO99/03837. WO99/06426, WO99/06042, WO91/17249, WO98/32733, WO98/17661, WO97/08174, WO95/34326, WO99/36426, and WO99/36415; European patent applications Publication Nos. EP534978 and EP89479; and French patent application no. FR 2762514. The disclosures of all of the aforementioned references are hereby incorporated by reference.

Interleukin-1 receptor antagonist (IL-1ra) is a human protein that acts as a natural inhibitor of interleukin-1 and is a member of the IL-1 family, which includes IL-1α and IL-13. Preferred receptor antagonists (including IL-1ra and variants and derivatives thereof), as well as methods of making and using thereof, are described in U.S. Pat. No. 5,075,222; International Patent Application Publication Nos. WO 91/08285; WO 91/17184; WO92/16221; WO93/21946; WO 94/06457; WO 94/21275; WO 94/21235; DE 4219626, WO 94/20517; WO 96/22793; WO 97/28828; and WO 99/36541, Australian Patent Application No. AU9173636; and French Patent Application No. FR2706772; the disclosures of which are incorporated herein by reference. The proteins include glycosylated as well as non-glycosylated forms of IL-1 receptor antagonists.

Specifically, three useful forms of IL-1ra and variants thereof are disclosed and described in U.S. Pat. No. 5,075,222 ("the '222 patent"). IL-1raα is characterized by SDS-PAGE as a 22-23 kD molecule having an approximate isoelectric point of 4.8, eluting from a Mono Q FPLC column at around 52 mM NaCl in Tris buffer, pH 7.6. IL-1rafβ is characterized as a 22-23 kD protein, eluting from a Mono Q column at 48 mM NaCl. Both IL-1rat and IL-1raβ are glycosylated. IL-1rax is characterized as a 20 kD protein, eluting from a Mono Q column at 48 mM NaCl, and is non-glycosylated. The '222 patent also discloses methods for isolating the genes responsible for coding the inhibitors, cloning the gene in suitable vectors and cell types, and expressing the gene to produce the inhibitors. While effective, IL-1ra has a relatively short half-life. In current use, IL-1ra is administered once a day. The art would thus benefit from an antagonist of the IL-1 receptor with an appreciably longer half-life.

Preventing IL-1 signaling by inhibiting IL-1 from binding the IL-1 receptor is an attractive therapeutic approach for treating IL-1 mediated diseases. There is a need in the art for clinically effective inhibitors of the IL-1 signaling pathway that may ameliorate the effects of IL-1 mediated diseases and are suitable for delivery into human patients. A human antibody that blocks IL-1 signaling would be particularly advantageous in fulfilling this need and would provide a longer half-life than currently available therapy.

SUMMARY OF THE INVENTION

The invention provides monoclonal antibodies that bind to interleukin-1 receptor type I (IL-1R1). Preferably, the antibodies inhibit IL-1 signaling by competing with IL-1β and IL-1α binding to IL-1R1. Also provided by this invention are hybridoma cell lines that produce, and most preferably, secrete into cell culture media the monoclonal antibodies of the invention. The antibodies of the invention successfully block IL-1 signaling in human cells and are useful thereby in treating patients with IL-1 mediated diseases. The invention further provides fusion proteins comprising the sequence of an antibody Fc region and one or more sequences selected from the group consisting of SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, and SEQ ID NO: 40. Such molecules can be prepared using methods as described, for example, in WO 00/24782, which is incorporated by reference. Such molecules can be expressed, for example, in mammalian cells (e.g. Chinese Hamster Ovary cells) or bacterial cells (e.g. E. coli cells).

In certain aspects, the invention provides antibodies, preferably monoclonal antibodies, most preferably human antibodies, comprising a heavy chain and a light chain, wherein the heavy chain comprises an amino acid sequence as set forth in any of SEQ ID NO: 2, SEQ ID NO: 6, or SEQ ID NO: 8, or an antigen-binding or an immunologically functional immunoglobulin fragment thereof.

The invention also provides antibodies, preferably monoclonal antibodies, most preferably human antibodies, comprising a heavy chain and a light chain, wherein the light chain comprises an amino acid sequence as set forth in SEQ ID NO: 4 or an antigen-binding or an immunologically functional immunoglobulin fragment thereof.

In certain aspects, antibodies of the invention comprise a heavy chain and a light chain, wherein the variable region of the heavy chain comprises an amino acid sequence as set forth in any of SEQ ID NO: 10, SEQ ID NO: 14, or SEQ ID NO: 16 or an antigen-binding or an immunologically functional immunoglobulin fragment thereof. In other aspects, the light chain variable region comprises an amino acid sequence as set forth in any of SEQ ID NO: 12 or SEQ ID NO: 18, or an antigen-binding or an immunologically functional immunoglobulin fragment thereof. In additional aspects, the heavy chain comprises an amino acid sequence as set forth in any of SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36, or an antigen-binding or an immunologically functional immunoglobulin fragment thereof. In still further aspects, the light chain comprises an amino acid sequence as set forth in any of SEQ ID NO: 38 or SEQ ID NO: 40, or an antigen-binding or an immunologically functional immunoglobulin fragment thereof. Such antibody chains are useful in preparing antibodies that bind specifically to IL-1R1 and also in preparation of bispecific antibodies in which the resulting molecule binds to IL-1R1 and/or to another target molecule (e.g., TNF or a TNF receptor).

The invention also provides antibodies that bind specifically to IL-1R1, wherein the heavy chain comprises a heavy chain variable region comprising an amino acid sequence as set forth in SEQ ID NO: 10, or an antigen-binding or an immunologically functional immunoglobulin fragment thereof, and the light chain comprises a light chain variable region comprising an amino acid sequence as set forth in SEQ ID NO: 12, or an antigen-binding or an immunologically functional immunoglobulin fragment thereof.

In certain aspects, the invention also provides antibodies, comprising a heavy chain and a light chain, wherein the heavy chain comprises a first variable region, and wherein the first variable region comprises a sequence that has at least 90%, more preferably at least 95%, and most preferably about 99% identity to the amino acid sequence as set forth in SEQ ID NO: 10, and wherein the light chain comprises a second variable region, and wherein the second variable region comprises a sequence that has at least 90%, more preferably at least 95%, and most preferably about 99%, identity to the amino acid sequence as set forth in SEQ ID NO: 12, wherein the antibody interacts with IL-1R1.

The invention further provides antibodies that specifically bind to IL-1R1, wherein the heavy chain comprises a heavy chain variable region comprising an amino acid sequence as set forth in SEQ ID NO: 14, or an antigen-binding or an immunologically functional immunoglobulin fragment thereof, and the light chain comprises a light chain variable region comprising an amino acid sequence as set forth in SEQ ID NO: 12, or an antigen-binding or an immunologically functional immunoglobulin fragment thereof.

In certain aspects, the invention provides antibodies, comprising a heavy chain and a light chain, wherein the heavy chain comprises a first variable region, and wherein the first variable region comprises a sequence that has at least 90%, more preferably at least 95%, and most preferably about 99%, identity to the amino acid sequence as set forth in SEQ ID NO: 14, and wherein the light chain comprises a second variable region, and wherein the second variable region comprises a sequence that has at least 90%, more preferably at least 95%, and most preferably about 99%, identity to the amino acid sequence as set forth in SEQ ID NO: 12, wherein the antibody interacts with IL-1R1.

The invention also provides antibodies that bind specifically to IL-1R1, wherein the heavy chain comprises a heavy chain variable region comprising an amino acid sequence as set forth in SEQ ID NO: 16, or an antigen-binding or an immunologically functional immunoglobulin fragment thereof, and the light chain comprises a light chain variable region comprising an amino acid sequence as set forth in SEQ ID NO: 18, or an antigen-binding or an immunologically functional immunoglobulin fragment thereof.

In certain aspects, the invention provides antibodies, comprising a heavy chain and a light chain, wherein the heavy chain comprises a first variable region, and wherein the first variable region comprises a sequence that has at least 90%, more preferably at least 95%, and most preferably about 99%, identity to the amino acid sequence as set forth in SEQ ID NO: 16, and wherein the light chain comprises a second variable region, and wherein the second variable region comprises an amino acid sequence that has at least 90%, more preferably at least 95%, and most preferably about 99%, identity to the amino acid sequence as set forth in SEQ ID NO: 18, wherein the antibody interacts with IL-1R1.

The invention also provides antibodies that bind specifically to IL-1R1, wherein the heavy chain comprises an amino acid sequence as set forth in SEQ ID NO: 20, SEQ ID NO: 22, SEQ ID NO: 24, SEQ ID NO: 26, SEQ ID NO: 28, or SEQ ID NO: 30, or an antigen-binding or an immunologically functional immunoglobulin fragment thereof, and the light chain comprises an amino acid sequence as set forth in SEQ ID NO: 38, or an antigen-binding or an immunologically functional immunoglobulin fragment thereof.

The invention further provides antibodies that bind specifically to IL-1R1, wherein the heavy chain comprises an amino acid sequence as set forth in SEQ ID NO: 32, SEQ ID NO: 34, or SEQ ID NO: 36, or an antigen-binding or an immunologically functional immunoglobulin fragment thereof, and the light chain comprises an amino acid sequence as set forth in SEQ ID NO: 40, or an antigen-binding or an immunologically functional immunoglobulin fragment thereof.

The invention also provides embodiments of all of the foregoing that are single chain antibodies, single chain Fv antibodies, Fab antibodies, Fab' antibodies and (Fab')$_2$ antibodies.

In particular aspects, the invention provides a light chain comprising an amino acid sequence as set forth in any of SEQ ID NO: 38 or SEQ ID NO: 40, or an antigen-binding or an immunologically functional immunoglobulin fragment thereof.

In addition, the invention provides a heavy chain comprising an amino acid sequence as set forth in any of SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36, or an antigen-binding or an immunologically functional immunoglobulin fragment thereof.

The invention also relates to isolated human antibodies that specifically bind IL-1R1, wherein the antibody comprises: (a) human heavy chain framework regions, a human heavy chain CDR1 region, a human heavy chain CDR2 region, and a human heavy chain CDR3 region; and (b) human light chain framework regions, a human light chain CDR1 region, a human light chain CDR2 region, and a human light chain CDR3 region. In certain aspects, the human heavy chain CDR1 region can be the heavy chain CDR1 region of 26F5, 27F2, or 15C4 as shown in FIG. 10 and the human light chain CDR1 region can be the light chain CDR1 region of 26F5, 27F2, or 15C4 as shown in FIG. 11. In other aspects, the human heavy chain CDR2 region can be the heavy chain CDR2 region of 26F5, 27F2, or 15C4 as shown in FIG. 10 and the human light chain CDR2 region can be the light chain CDR2 region of 26F5, 27F2, or 15C4 as shown in FIG. 11. In still other aspects, the human heavy chain CDR3 region is the heavy chain CDR3 region of 26F5, 27F2, or 15C4 as shown in FIG. 10, and the human light chain CDR3 region is the light chain CDR3 region of 26F5, 27F2, or 15C4 as shown in FIG. 11.

In addition, the invention provides an isolated human antibody that specifically binds to interleukin-1 receptor type 1 (IL-1R1), comprising: a human heavy chain CDR1 region, wherein the heavy chain CDR1 has the amino acid sequence of SEQ ID NO: 61, SEQ ID NO: 62, or SEQ ID NO: 63; a human heavy chain CDR2 region, wherein the heavy chain CDR2 has the amino acid sequence of SEQ ID NO: 64, SEQ ID NO: 65, or SEQ ID NO: 66; and/or a human heavy chain CDR3 region, wherein the heavy chain CDR3 has the amino acid sequence of SEQ ID NO: 67, SEQ ID NO: 68, or SEQ ID NO: 69.

The invention also provides an isolated human antibody that specifically binds to interleukin-1 receptor type 1 (IL-1R1), comprising: a human light chain CDR1 region, wherein the light chain CDR1 has the amino acid sequence of SEQ ID NO: 70 or SEQ ID NO: 71; a human heavy chain CDR2 region, wherein the heavy chain CDR2 has the amino acid sequence of SEQ ID NO: 72 or SEQ ID NO: 73; and/or a human heavy chain CDR3 region, wherein the heavy chain CDR3 has the amino acid sequence of SEQ ID NO: 74 or SEQ ID NO: 75.

In certain embodiments, the antibodies of the invention bind to the third domain of IL-1R1, which is shown in FIG. 17. Preferably, the epitope for an antibody of the invention consists of the amino acid sequence YSV, which is referred to as Epitope 4 herein and shown in FIG. 24. The invention further relates to fusion proteins and other molecules capable of binding to Epitope 4 (together with the aforementioned antibodies, collectively referred to herein as "specific binding partners"), such as may be prepared using methods as described, for example, in WO 00/24782, which is incorporated by reference. Such molecules can be expressed, for example, in mammalian cells (e.g. Chinese Hamster Ovary cells) or bacterial cells (e.g. *E. coli* cells).

Furthermore, the invention provides a method for epitope mapping of a selected antigen. In one aspect, the method comprises the steps of: (a) generating a set of fusion proteins, wherein each fusion protein comprises (i) avidin and (ii) a fragment of the antigen; (b) screening the set of fusion proteins for binding to one or more specific binding partners for the antigen; (c) isolating the fusion proteins on a medium comprising biotin, whereby the avidin binds to the biotin; and (d) analyzing the fusion proteins bound by the specific binding partner or partners to determine binding sites on the antigen for the specific binding partner or partners. In a particular aspect, the specific binding partners are antibodies.

In additional embodiments, the invention provides methods for treating an IL-1 mediated disease, condition or disorder, comprising the step of administering a pharmaceutically effective amount of one or a plurality of monoclonal antibodies of the invention or an antigen-binding or an immunologically functional immunoglobulin fragment thereof to an individual in need thereof.

The invention also provides methods for detecting the level of IL-1R1 in a biological sample, comprising the step of contacting the sample with a monoclonal antibody of the invention or antigen-binding fragment thereof. The anti-IL-1R antibodies of the invention may be employed in any known assay method, such as competitive binding assays, direct and indirect sandwich assays, immunoprecipitation assays and enzyme-linked immunosorbent assays (ELISA) (See, Sola, 1987, *Monoclonal Antibodies: A Manual of Techniques*, pp. 147-158, CRC Press, Inc.) for the detection and quantitation of IL-1R. The antibodies can bind IL-1R with an affinity that is appropriate for the assay method being employed.

Specific preferred embodiments of the invention will become evident from the following more detailed description of certain preferred embodiments and the claims.

BRIEF DESCRIPTION OF THE FIGURES

FIGS. 1A-1B depict a cDNA sequence (FIG. 1A) encoding a human anti-IL-1R1 antibody heavy chain IgG1 constant region (SEQ ID NO: 1) and the amino acid sequence (FIG. 1B) of a human anti-IL-1R1 antibody heavy chain IgG1 constant region (SEQ ID NO: 2).

FIGS. 2A-2B depict a cDNA sequence (FIG. 2A) encoding a human anti-IL-1R1 antibody kappa chain constant region (SEQ ID NO: 3) and the amino acid sequence (FIG. 2B) of a human anti-IL-1R1 antibody kappa chain constant region (SEQ ID NO: 4).

FIGS. 3A-3B depict a cDNA sequence (FIG. 3A) encoding a human anti-IL-1R1 antibody heavy chain IgG2 constant region (SEQ ID NO: 5) and the amino acid sequence (FIG. 3B) of a human anti-IL-1R1 antibody heavy chain IgG2 constant region (SEQ ID NO: 6).

FIGS. 4A-4B depict a cDNA sequence (FIG. 4A) encoding a human anti-IL-1R1 antibody heavy chain IgG4 constant region (SEQ ID NO: 7) and the amino acid sequence (FIG. 4B) of a human anti-IL-1R1 antibody heavy chain IgG4 constant region (SEQ ID NO: 8).

FIGS. 5A-5B depict a cDNA sequence (FIG. 5A) encoding the 26F5 anti-IL-1R1 antibody heavy chain variable region (SEQ ID NO: 9) and the amino acid sequence (FIG. 5B) of the 26F5 anti-IL-1R1 antibody heavy chain variable region (SEQ ID NO: 10).

FIGS. 6A-6B depict a cDNA sequence (FIG. 6A) encoding the 26F5 anti-IL-1R1 antibody kappa chain variable region (SEQ ID NO: 11) and the amino acid sequence (FIG. 6B) of the 26F5 anti-IL-1R1 antibody kappa chain variable region (SEQ ID NO: 12).

FIGS. 7A-7B depict a cDNA sequence (FIG. 7A) encoding the 27F2 anti-IL-1R1 antibody heavy chain variable region (SEQ ID NO: 13) and the amino acid sequence (FIG. 7B) of the 27F2 anti-IL-1R1 antibody heavy chain variable region (SEQ ID NO: 14).

FIGS. 8A-8B depict a cDNA sequence (FIG. 8A) encoding the 15C4 anti-IL-1R1 antibody heavy chain variable region (SEQ ID NO: 15) and the amino acid sequence (FIG. 8B) of the 15C4 anti-IL-1R1 antibody heavy chain variable region (SEQ ID NO: 16).

FIGS. 9A-9B depict a cDNA sequence (FIG. 9A) encoding the 15C4 anti-IL-1R1 antibody kappa chain variable region (SEQ ID NO: 17) and the amino acid sequence (FIG. 9B) of the 15C4 anti-IL-1R1 antibody kappa chain variable region (SEQ ID NO: 18).

FIG. 10 shows an amino acid sequence alignment of heavy chains from anti-IL-1R1 antibodies designated 15C4 (SEQ ID NO: 80), 27F2 (SEQ ID NO: 82), and 26F5 (SEQ ID NO: 84). The complementarity determining regions (CDRs) are underlined. CDR1 for 26F5 is designated SEQ ID NO: 61; for 27F2 is designated SEQ ID NO: 62; for 15C4 is designated SEQ ID NO: 63. CDR2 for 26F5 is designated SEQ ID NO: 64; for 27F2 is designated SEQ ID NO: 65; for 15C4 is designated SEQ ID NO: 66. CDR1 for 26F5 is designated SEQ ID NO: 67; for 27F2 is designated SEQ ID NO: 68; for 15C4 is designated SEQ ID NO: 69.

FIG. 11 shows an amino acid sequence alignment of light chains from anti-IL-R1-γ antibodies designated 15C4 (SEQ ID NO: 81), 27F2 (SEQ ID NO: 83), and 26F5 (SEQ ID NO: 83). CDR1 for 26F5/27F2 is designated SEQ ID NO: 70; for 15C4 is designated SEQ ID NO: 71. CDR2 for 26F5/27F2 is designated SEQ ID NO: 72; for 15C4 is designated SEQ ID NO: 73. CDR3 for 26F5/27F2 is designated SEQ ID NO: 74; for 15C4 is designated SEQ ID NO: 75.

FIG. 17 depicts human amino acid (SEQ ID NO: 76) and nucleotide (SEQ ID NO: 77) and rat nucleotide (SEQ ID NO: 78) and amino acid (SEQ ID NO: 79) $3^{rd}$ domain IL-1R1 sequences. The numbered bars above the human sequence indicate the 15 different sites mutated to construct the 15 different mutated proteins. The rat residues introduced by mutation are listed below the rat nucleic acid sequence.

FIG. 23 depicts the amino acid sequence (SEQ ID NO: 59) of the avidin-human IL-1R1-FLAG chimeric protein of the invention.

FIG. 24 depicts the amino acid sequence (SEQ ID NO: 60) of an avidin-cynomolgus IL-1R1-FLAG chimeric protein. The recombinant chicken avidin (italicized) is joined to the mature extracellular domain of cynomolgus IL-1R1 (underlined, with C-terminal FLAG tag in bold) by a 6 amino acid linker. Four amino acids from human IL-1R1 that were introduced alone and in combination into the cynomolgus sequence are in bold under the cynomolgus sequence. Epitope 4 is bold, italicized, and underlined.

FIG. 25A shows a Western blot analysis of anti-human IL1-1R1 antibody (anti-huIL1-R1) binding to II-1R1. The * indicates that antibodies were used at 5 μg/mL, whereas in the remainder antibodies were used at 1 μg/mL.

FIG. 25B shows a summary of the densitometric analysis of a duplicate set of Western blot experiments.

DETAILED DESCRIPTION OF CERTAIN PREFERRED EMBODIMENTS

Figure 12:
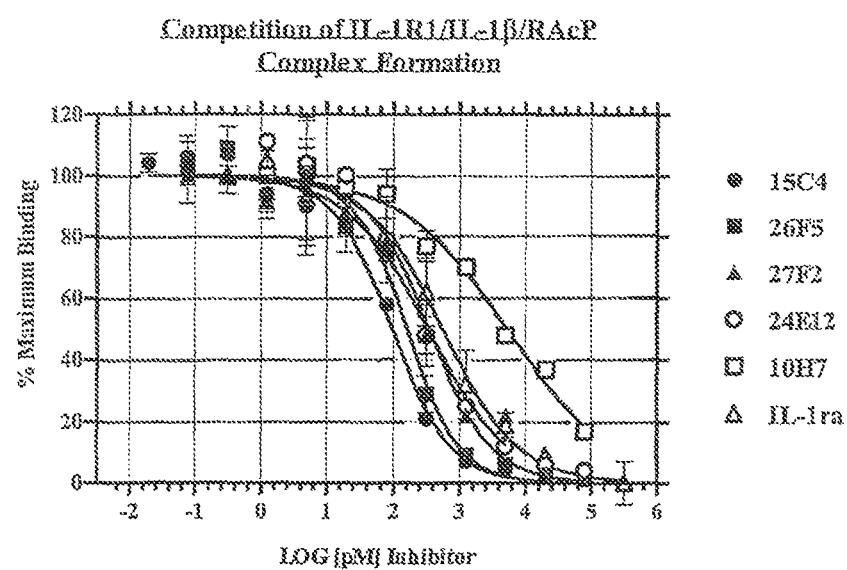
FIG. 12 is a graph illustrating the inhibitory effect of anti-IL-1R1 antibodies on IL-1R/IL-13/IL-1RAcP complex formation.

The section headings used herein are for organizational purposes only and are not to be construed as limiting the subject matter described. All references cited in this application are expressly incorporated by reference herein for any purpose.

Definitions

A disease or medical condition is considered to be an "interleukin-1 (IL-1) mediated disease" if the naturally-occurring or experimentally-induced disease or medical condition is associated with elevated levels of IL-1 in bodily fluids or tissue or if cells or tissues taken from the body produce elevated levels of IL-1 in culture. Elevated levels of IL-1 can include, for example, levels that exceed those normally found in a particular cell or tissue, or can be any detectable level of IL-1 in a cell or tissue that normally does not express IL-1. In many cases, IL-1 mediated diseases are also recognized by the following additional two conditions: (1) pathological findings associated with the disease or medical condition can be mimicked experimentally in animals by administration of IL-1 or up-regulation of expression of IL-1; and (2) a pathology induced in experimental animal models of the disease or medical condition can be inhibited or abolished by treatment with agents that inhibit the action of IL-1. In most IL-1 mediated diseases at least two of the three conditions are met, and in many IL-1 mediated diseases all three conditions are met.

A non-exclusive list of acute and chronic IL-1-mediated diseases includes but is not limited to the following: acute pancreatitis; amyelolateroschlerosis (ALS); Alzheimer's disease; cachexia/anorexia, including AIDS-induced cachexia; asthma and other pulmonary diseases; atherosclerosis; autoimmune vasculitis; chronic fatigue syndrome; *Clostridium* associated illnesses, including *Clostridium*-associated diarrhea; coronary conditions and indications, including congestive heart failure, coronary restenosis, myocardial infarction, myocardial dysfunction (e.g., related to sepsis), and coronary artery bypass graft; cancer, such as multiple myeloma and myelogenous (e.g., AML or CML) and other leukemias, as well as tumor metastasis; diabetes (e.g., insulin-dependent diabetes); endometriosis; fever, fibromyalgia; glomerulonephritis; graft versus host disease/transplant rejection; hemorrhagic shock; hyperalgesia; inflammatory bowel disease; inflammatory conditions of a joint, including osteoarthritis, psoriatic arthritis and rheumatoid arthritis; inflammatory eye disease, as may be associated with, e.g., corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); multiple sclerosis; myopathies (e.g., muscle protein metabolism, especially in sepsis); neurotoxicity (e.g., as induced by HIV); osteoporosis; pain, including cancer-related pain; Parkinson's disease; periodontal disease; pre-term labor; psoriasis; reperfusion injury; septic shock; side effects from radiation therapy; temporal mandibular joint disease; sleep disturbance; uveitis; or an inflammatory condition resulting from strain, sprain, cartilage damage, trauma, orthopedic surgery, infection or other disease processes. Methods of the invention for treating these acute and chronic IL-1-mediated diseases, as well as other IL-1-mediated conditions and diseases, are described below.

Conventional techniques may be used for preparing recombinant DNA, performing oligonucleotide synthesis, and practicing tissue culture and transformation (e.g., electroporation, transfection or lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., 2001, *Molecular Cloning: A Laboratory Manual*, 3rd ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" means that the subject polynucleotide, (1) is not associated (covalently or noncovalently) with all or a portion of other polynucleotides with which the subject polynucleotide is associated in nature, (2) is associated with a molecule with which it is not associated in nature, or (3) does not occur in nature associated with any other polynucleotides. Such an isolated polynucleotide may be genomic DNA, cDNA, mRNA or other RNA, of synthetic origin, or any combination thereof.

The term "isolated protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass anti-IL1-R1 antibodies, or sequences that have deletions from, additions to, and/or substitutions of one or more amino acid of an anti-ILR-1R1 antibody. Thus, a "polypeptide" or a "protein" can comprising one (termed "a monomer") or a plurality (termed "a multimer") of amino acid chains.

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 8, 10, 14, 20, 50, 70, 100, 110, 150, 200, 250, 300, 350, 400, or 450 amino acids long. Particularly useful polypeptide fragments include functional domains, including binding domains. In the case of an anti-IL1-R1 antibody, useful fragments include, but are not limited to: a CDR region, especially a CDR3 region of the heavy or light chain; a variable domain of a heavy or light chain; a portion of an antibody chain or just its variable region including two CDRs; and the like.

The term "immunologically functional immunoglobulin fragment" as used herein refers to a polypeptide fragment that contains at least the variable domains of the immunoglobulin heavy and light chains. An immunologically functional immunoglobulin fragment of the invention is capable of binding to a ligand, preventing binding of the ligand to its receptor, interrupting the biological response resulting from ligand binding to the receptor, or any combination thereof. Preferably, an immunologically functional immunoglobulin fragment of the invention binds specifically to IL-1R1.

The terms "naturally occurring" and "native" mean that the biological materials (molecules, sequences, protein complexes, cells, and the like) to which the terms are applied can be found in nature and are not manipulated by man. For example, a polypeptide or polynucleotide sequence that is present in an organism (including viruses) that can be isolated from a source in nature and that has not been intentionally modified by man is naturally occurring. Likewise, the terms "non-naturally occurring" or "non-native" refer to a material that is not found in nature or that has been structurally modified or synthesized by man.

The term "operably linked" means that the components to which the term is applied are in a relationship that allows them to carry out their inherent functions under suitable conditions. For example, a control sequence "operably linked" to a protein coding sequence is ligated thereto so that expression of the protein coding sequence is achieved under conditions compatible with the transcriptional activity of the control sequences.

The term "control sequence" means that the subject polynucleotide sequence can effect expression and processing of coding sequences to which it is ligated. The nature of such control sequences may depend upon the host organism. In particular embodiments, control sequences for prokaryotes may include a promoter, ribosomal binding site, and transcription termination sequence. In other particular embodiments, control sequences for eukaryotes may include promoters comprising one or a plurality of recognition sites for transcription factors, transcription enhancer sequences, and transcription termination sequence. In certain embodiments, "control sequences" can include leader sequences and/or fusion partner sequences.

The term "polynucleotide" means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term includes single and double stranded forms of DNA.

The term "oligonucleotide" means a polynucleotide comprising a length of 200 bases or fewer. In preferred embodiments, oligonucleotides are 10 to 60 bases in length. In more preferred embodiments, oligonucleotides are 12, 13, 14, 15, 16, 17, 18, 19, or 20 to 40 bases in length. Oligonucleotides may be single stranded or double stranded, e.g., for use in the construction of a mutant gene. Oligonucleotides of the invention may be sense or antisense oligonucleotides.

The term "naturally occurring nucleotides" includes deoxyribonucleotides and ribonucleotides. The term "modified nucleotides" includes nucleotides with modified or substituted sugar groups or modified or substituted bases. The term "oligonucleotide linkages" includes linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. (1986), *Nucl. Acids Res.* 14:9081; Stec et al. (1984), *J. Am. Chem. Soc.* 106:6077; Stein et al. (1988), *Nucl. Acids Res.* 16:3209; Zon et al. (1991), *Anti-Cancer Drug Design* 6:539; Zon et al. (1991), *Oligonucleotides and Analogues: A Practical Approach*, pp. 87-108 (F. Eckstein, ed.), Oxford University Press, Oxford England; Stec et al., U.S. Pat. No. 5,151,510; Uhlmann and Peyman (1990), *Chemical Reviews* 90:543, the disclosures of which are hereby incorporated by reference for any purpose. An oligonucleotide of the invention can include a label, including a radiolabel, a fluorescent label, a hapten or an antigenic label, for detection assays.

The term "vector" means any molecule (e.g., nucleic acid, plasmid, or virus) used to transfer coding information to a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and RNA splicing, if introns are present, of a coding region operably linked thereto.

The term "host cell" means a cell that has been transformed, or is capable of being transformed, with a nucleic acid sequence and thereby expresses a selected gene of interest. The term includes the progeny of the parent cell, whether or not the progeny is identical in morphology or in genetic make-up to the original parent cell, so long as the selected gene is present.

The term "transduction" means the transfer of genes from one bacterium to another, usually by phage. "Transduction" also refers to the acquisition and transfer of eukaryotic cellular sequences by retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, *Molecular Cloning: A Laboratory Manual, Id.*; Davis et al., 1986, *Basic Methods in Molecular Biology, Elsevier*; and Chu et al., 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA. For example, a cell is transformed where it is genetically modified from its native state by transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In preferred embodiments, an antibody is said to specifically bind an antigen when the dissociation constant is less than or equal to about 10 nM, more preferably when the dissociation constant is less than or equal to about 100 pM, and most preferably when the dissociation constant is less than or equal to about 10 pM.

The term "identity" refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between sequences of two or more nucleotides or two or more amino acids. "Identity" measures the percentage of identical matches between the smaller of two or more sequences with gap alignments (if any) addressed by a particular mathematical model or computer program (i.e., "algorithms").

The term "similarity" is used in the art with regard to a related concept; in contrast to "identity," however, "similarity" refers to a measure of relatedness that includes both identical matches and conservative substitution matches. If two polypeptide sequences have, for example, 10/20 identical amino acids, and the remainder are all non-conservative substitutions, then the percentage identity and similarity would both be 50%. If in the same example, there are five more positions where there are conservative substitutions, then the percentage identity remains 50%, but the percentage similarity would be 75% (15/20). Therefore, in cases where there are conservative substitutions, the percentage similarity between two polypeptides will be higher than the percentage identity between those two polypeptides.

Identity and similarity of related nucleic acids and polypeptides can be readily calculated by known methods. Such methods include, but are not limited to, those described in *Computational Molecular Biology*, (Lesk, A. M., ed.), 1988, Oxford University Press, New York; *Biocomputing: Informatics and Genome Projects*, (Smith, D. W., ed.), 1993. Academic Press, New York; *Computer Analysis of Sequence Data*, Part 1, (Griffin, A. M., and Griffin, H. G., eds.), 1994, Humana Press, New Jersey; von Heinje, G., *Sequence Analysis in Molecular Biology*, 1987, Academic Press; *Sequence Analysis Primer*, (Gribskov, M. and Devereux, J., eds.), 1991, M. Stockton Press, New York; Carillo et al., 1988, *SIAM J. Applied Math.* 48:1073; and Durbin et al., 1998, *Biological Sequence Analysis*, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, *Nucl. Acid. Res.* 12:387; Genetics Computer Group, University of Wisconsin, Madison, Wis.), BLASTP, BLASTN, and FASTA (Altschul et al., 1990, *J. Mol. Biol.* 215:403-410). The BLASTX program is publicly available from the National Center for Biotechnology Information (NCBI) and other sources (*BLAST Manual*, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid sequences may result in matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percentage sequence identity is to be determined are aligned for optimal matching of their respective amino acids (the "matched span", as determined by the algorithm). In certain embodiments, a gap opening penalty (which is calculated as three-times the average diagonal; where the "average diagonal" is the average of the diagonal of the comparison matrix being used; the "diagonal" is the score or number assigned to each perfect amino acid match by the particular comparison matrix) and a gap extension penalty (which is usually one-tenth of the gap opening penalty), as well as a comparison matrix such as PAM250 or BLOSUM 62 are used in conjunction with the algorithm. In certain embodiments, a standard comparison matrix (see Dayhoff et al., 1978, *Atlas of Protein Sequence and Structure* 5:345-352 for the PAM 250 comparison matrix; Henikoff et al., 1992, *Proc. Nail. Acad. Sci. USA* 89:10915-10919 for the BLOSUM 62 comparison matrix) is also used by the algorithm.

In certain embodiments, the parameters for a polypeptide sequence comparison include the following:

Algorithm: Needleman et al. (1970), *J. Mol. Biol.* 48:443-453;

Comparison matrix: BLOSUM 62 from Henikoff et al. (1992), supra;

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

The term "naturally occurring," as used to refer to amino acids, refers to the twenty conventional amino acids. See *Immunology—A Synthesis*, 2nd Edition, (E. S. Golub and D. R. Gren, eds.), Sinauer Associates: Sunderland, Mass. (1991), incorporated herein by reference for any purpose.

Peptide analogs are commonly used in the pharmaceutical industry as non-peptide drugs with properties analogous to those of the template peptide. These types of non-peptide compounds are termed "peptide mimetics" or "peptidomimetics". See Fauchere (1986), *Adv. Drug Res.* 15:29; Veber & Freidinger, 1985, *TINS* p. 392; and Evans et al. (1987), *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm peptide or polypeptide (i.e., a peptide or polypeptide that has a biochemical property or pharmacological activity), such as human antibody, but have one or more peptide linkages optionally replaced by a linkage selected from: —$CH_2$—NH—, —$CH_2$—S—, —$CH_2$—$CH_2$—, —CH=CH-(cis and trans), —$COCH_2$—, —CH(OH)$CH_2$—, and —$CH_2$SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies.

The term "heavy chain" includes a full-length heavy chain and fragments thereof having sufficient variable region sequence to confer specificity for IL-1R1. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxyl-terminus.

The term "light chain" includes a full-length light chain and fragments thereof having sufficient variable region sequence to confer specificity for IL-1R1. A full-length light chain includes a variable region domain, $V_L$, and a constant region domain, $C_L$. Like the heavy chain, the variable region domain of the light chain is at the amino-terminus of the polypeptide.

A "Fab fragment" is comprised of one light chain and the $C_H1$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_H1$ and $C_H2$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference for any purpose.

A "bivalent antibody" other than a "multispecific" or "multifunctional" antibody, in certain embodiments, is understood to comprise binding sites having identical antigenic specificity.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann (1990), *Clin. Exp. Immunol.* 79:315-321; Kostelny et al. (1992), *J. Immunol.* 148:1547-1553.

In assessing antibody binding and specificity according to the invention, an antibody "substantially inhibits" adhesion of a ligand to a receptor when an excess of antibody reduces the quantity of receptor bound to counterreceptor by at least about 20%, 40%, 60%, 80%, 85%, or more (as measured in an in vitro competitive binding assay).

The term "agent" means a chemical compound, a mixture of chemical compounds, a biological macromolecule, or an extract made from biological materials.

The terms "label" or "labeled" refers to incorporation of a detectable marker, e.g., by incorporation of a radiolabeled amino acid or attachment to a polypeptide of biotin moieties that can be detected by marked avidin (e.g., streptavidin preferably comprising a detectable marker such as a fluorescent marker, a chemiluminescent marker or an enzymatic activity that can be detected by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to, the following: radioisotopes or radionuclides (e.g., $^3H$, $^{14}C$, $^{15}N$, $^{35}S$, $^{90}Y$, $^{99m}Tc$, $^{111}In$, $^{125}I$, $^{131}I$), fluorescent labels (e.g., fluorescein isothiocyanate (FITC), rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, epitope tags). In certain embodiments, labels are attached by spacer arms (such as $(CH_2)_n$, where n<about 20) of various lengths to reduce potential steric hindrance.

The term "biological sample" includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph, lymph nodes, synovial tissue, chondrocytes, synovial macrophages, endothelial cells, vascular tissue (particularly inflamed vascular tissue), and skin. The terms "pharmaceutical agent" and "drug" refer to a chemical compound or composition capable of inducing a desired therapeutic effect when properly administered to a patient.

The term "patient" includes human and animal subjects.

Unless otherwise required by context, singular terms shall include pluralities and plural terms shall include the singular.

Amino Acids

The twenty naturally-occurring amino acids and their abbreviations follow conventional usage. See *Immunology—A Synthesis,* 2nd Edition, (E. S. Golub and D. R. Gren, eds.), Sinauer Associates: Sunderland, Mass. (1991), incorporated herein by reference for any purpose. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences".

Naturally occurring amino acid residues may be divided into classes based on common side chain properties:
1) hydrophobic: norleucine (Nor or Nle), Met, Ala, Val, Leu, Ile;
2) neutral hydrophilic: Cys, Ser. Thr, Asn, Gln;
3) acidic: Asp. Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced, for example, into regions of a human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

| Amino Acid Substitutions | | |
|---|---|---|
| Original Residues | Exemplary Substitutions | Preferred Substitutions |
| Ala | Val, Leu, Ile | Val |
| Arg | Lys, Gln, Asn | Lys |
| Asn | Gln | Gln |
| Asp | Glu | Glu |

TABLE 1-continued

Amino Acid Substitutions

| Original Residues | Exemplary Substitutions | Preferred Substitutions |
|---|---|---|
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, Curr. Op. in Biotech. 7:422-427; Chou et al., 1974, Biochemistry 13:222-245; Chou et al., 1974, Biochemistry 113:211-222; Chou et al., 1978, Adv. Enzymol. Relat. Areas Mol. Biol. 47:45-148; Chou et al., 1979, Ann. Rev. Biochem. 47:251-276; and Chou et al., 1979, Biophys. J. 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, Nucl. Acid. Res. 27:244-247. It has been suggested (Brenner et al., 1997, Curr. Op. Struct. Biol. 7:369-376) that there are a limited number of folds in a given polypeptide or protein and that once a critical number of structures have been resolved, structural prediction will become dramatically more accurate.

Additional methods of predicting secondary structure include "threading" (Jones, 1997, Curr. Opin. Struct. Biol. 7:377-87; Sippl et al., 1996, Structure 4:15-19), "profile analysis" (Bowie et al., 1991, Science 253:164-170; Gribskov et al., 1990, Meth. Enzym. 183:146-159; Gribskov et al., 1987, Proc. Nat. Acad. Sci. 84:4355-4358), and "evolutionary linkage" (See Holm, 1999, supra; and Brenner, 1997, supra).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In preferred embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles, (Creighton, ed.), 1984, W. H. Freeman and Company, New York; Introduction to Protein Structure (C. Branden and J. Tooze, eds.), 1991, Garland Publishing, New York, N.Y.; and Thornton et al. (1991), Nature 354:105, each of which are incorporated herein by reference.

Preparation of Antibodies

Naturally occurring antibody structural units typically comprise a tetramer. Each such tetramer typically is composed of two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, a "J" region of about 12 or more amino acids joins the variable region and constant regions, with the heavy chain also including a "D" region of about 10 more amino acids. See, e.g., Fundamental Immunology, Ch. 7, $2^{nd}$ ed., (Paul, W., ed.), 1989, Raven Press, N.Y. (incorporated by reference in its entirety for all purposes). The combination of the variable regions of each light chain/heavy chain pair typically forms the antigen-binding site.

The variable regions of each of the heavy chains and light chains typically exhibit the same general structure comprising four relatively conserved framework regions (FR) joined by three hyper variable regions, also called complementarity determining regions or CDRs. The CDRs from the two chains of each pair typically are aligned by the framework regions, which alignment may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (1987 and 1991, National Institutes of Health, Bethesda, Md.), Chothia & Lesk, 1987, J. Mol. Biol. 196:901-917, or Chothia et al., 1989, Nature 342:878-883).

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 13:3001; and Brodeur et al., 1987, Monoclonal Antibody Production Techniques and Applications, (Marcel Dekker, Inc., New York), pp. 51-63).

Monoclonal antibodies may be modified for use as therapeutics. One example is a "chimeric" antibody in which a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Other examples are fragments of such antibodies, so long as they exhibit the desired biological activity. See, U.S. Pat. No. 4,816,567; and Morrison et al. (1985), Proc. Natl. Acad. Sci. USA 81:6851-6855. A related development is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass.

Another development is the "humanized" antibody. Methods for humanizing non-human antibodies are well known in the art. (See U.S. Pat. Nos. 5,585,089, and 5,693,762). Generally, a humanized antibody is produced by a non-human animal, and then certain amino acid residues, typically from non-antigen recognizing portions of the antibody, are modified to be homologous to said residues in a human antibody of corresponding isotype. Humanization can be performed, for example, using methods described in the art (Jones et al., 1986, Nature 321:522-525; Riechmann et al., 1988, Nature 332:323-327; Verhoeyen et al., 1988, Science 239:1534-1536), by substituting at least a portion of a rodent variable region for the corresponding regions of a human antibody.

More recent and more promising is the development of human antibodies without exposure of antigen to human beings ("fully human antibodies"). Using transgenic animals (e.g., mice) that are capable of producing a repertoire of human antibodies in the absence of endogenous mouse immunoglobulin production, such antibodies are produced by immunization with an antigen (typically having at least 6 contiguous amino acids), optionally conjugated to a carrier. See, for example, Jakobovits et al., 1993, Proc. Natl. Acad. Sci. USA 90:2551-2555; Jakobovits et al., 1993, Nature 362:255-258; and Bruggermann et al., 1993, Year in Immunol. 7:33. In one example of these methods, transgenic animals are produced by incapacitating the endogenous mouse immunoglobulin loci encoding the mouse heavy and light immunoglobulin chains therein, and inserting loci encoding human heavy and light chain proteins into the genome thereof. Partially modified animals, which have less than the full complement of modifications, are then cross-bred to obtain an animal having all of the desired immune system modifications. When administered an immunogen, these transgenic animals produce antibodies that are immunospecific for these antigens having human (rather than murine) amino acid sequences, including variable regions. See PCT Publication Nos. WO96/33735 and WO94/02602, incorporated by reference. Additional methods are described in U.S. Pat. No. 5,545,807, PCT Publication Nos. WO91/10741, WO90/04036, and in EP 546073B1 and EP 546073A 1, incorporated by reference. Human antibodies may also be produced by the expression of recombinant DNA in host cells or by expression in hybridoma cells as described herein.

Fully human antibodies can also be produced from phage-display libraries (as disclosed in Hoogenboom et al., 1991, J. Mol. Biol. 227:381; and Marks et al., 1991, J. Mol. Biol. 222:581). These processes mimic immune selection through the display of antibody repertoires on the surface of filamentous bacteriophage, and subsequent selection of phage by their binding to an antigen of choice. One such technique is described in PCT Publication No. WO99/10494, incorporated by reference, which describes the isolation of high affinity and functional agonistic antibodies for MPL- and msk-receptors using such an approach.

Once the nucleotide sequences encoding such antibodies have been determined, chimeric, CDR-grafted, humanized, and fully human antibodies also may be produced by recombinant methods. Nucleic acids encoding the antibodies are introduced into host cells and expressed using materials and procedures generally known in the art.

The invention provides one or a plurality of fully human monoclonal antibodies against human IL-1R1. Preferably, the antibodies bind the third domain of IL-1R1. In preferred embodiments, the invention provides nucleotide sequences encoding, and amino acid sequences comprising, heavy and light chain immunoglobulin molecules, particularly sequences corresponding to the variable regions thereof. In preferred embodiments, sequences corresponding to complementarity determining regions (CDR's), specifically from CDR1 through CDR3, are provided. In additional preferred embodiments, the invention provides hybridoma cell lines expressing such immunoglobulin molecules and monoclonal antibodies produced therefrom, most preferably purified human monoclonal antibodies against human IL-1R1.

The ability to clone and reconstruct megabase-sized human loci in yeast artificial chromosomes (YACs) and to introduce them into the mouse germline provides an advantageous approach to elucidating the functional components of very large or crudely mapped loci as well as generating useful models of human disease. Furthermore, the utilization of such technology for substitution of mouse loci with their human equivalents provides unique insights into expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy provides a source for production of fully human monoclonal antibodies (MAbs), particularly for use as therapeutic agents. Fully human antibodies are expected to minimize the immunogenic and allergic responses intrinsic to mouse or mouse-derivatized Mabs, and to thereby increase the efficacy and safety of administered antibodies in therapeutic applications. Fully human antibodies can be used in the treatment of chronic and recurring human diseases, such as osteoarthritis, rheumatoid arthritis, and other inflammatory conditions, the treatment thereof requiring repeated antibody administration.

One skilled in the art can engineer mouse strains deficient in mouse antibody production with large fragments of the human Ig loci so that such mice produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains yields high affinity antibodies against any antigen of interest, including human antigens. Using the hybridoma technology, antigen-specific human MAbs with the desired specificity may be produced and selected.

In certain embodiments, the skilled artisan can use constant regions from species other than human along with the human variable region(s) in such mice to produce chimeric antibodies. The antibodies of the invention can be produced by immunizing such animals with full-length IL-1R1, soluble forms of IL-1R1, or a fragment thereof. See, for example, International Patent Application, Publication WO 93/12227).

The CDRs of the light and heavy chain variable regions of anti-IL-1R1 antibodies of the invention can be grafted to framework regions (FRs) from the same, or another, species. In certain embodiments, the CDRs of the light and heavy chain variable regions of anti-IL-1R1 antibody may be grafted to consensus human FRs. To create consensus human FRs, FRs from several human heavy chain or light chain amino acid sequences are aligned to identify a consensus amino acid sequence. The FRs of the anti-IL-1R1 antibody heavy chain or light chain can be replaced with the FRs from a different heavy chain or light chain. Rare amino acids in the FRs of the heavy and light chains of anti-IL-1R1 antibody typically are not replaced, while the rest of the FR amino acids can be replaced. Rare amino acids are specific amino acids that are in positions in which they are not usually found in FRs. The grafted variable regions from anti-IL-1R1 antibodies of the invention can be used with a constant region that is different from the constant region of anti-IL-1R1 antibody. Alternatively, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

In certain embodiments, the invention provides anti-IL1-R1 antibodies that comprise a human heavy chain CDR1 region having an amino acid sequence of SEQ ID NO: 61, SEQ ID NO: 62, or SEQ ID NO: 63; a human heavy chain CDR2 region having an amino acid sequence of SEQ ID NO: 64, SEQ ID NO: 65, or SEQ ID NO: 66; and/or a human heavy chain CDR3 region having an amino acid sequence of SEQ ID NO: 67, SEQ ID NO: 68, or SEQ ID NO: 69.

In other embodiments, the invention provides anti-IL1-R1 antibodies that comprise a human light chain CDR1 region having an amino acid sequence of SEQ ID NO: 70 or SEQ ID NO: 71; a human heavy chain CDR2 region having an amino acid sequence of SEQ ID NO: 72 or SEQ ID NO: 73; and/or a human heavy chain CDR3 region having an amino acid sequence of SEQ ID NO: 74 or SEQ ID NO: 75.

Antibodies of the invention are preferably prepared using transgenic mice that have a substantial portion of the human antibody-producing locus inserted in antibody-producing cells of the mice, and that are further engineered to be deficient in producing endogenous, murine, antibodies. Such mice are capable of producing human immunoglobulin molecules and antibodies and do not produce or produce substantially reduced amounts of murine immunoglobulin molecules and antibodies. Technologies utilized for achieving this result are disclosed in the patents, applications, and references disclosed in the specification herein. In preferred embodiments, the skilled worker may employ methods as disclosed in International Patent Application Publication No. WO 98/24893, which is hereby incorporated by reference for any purpose. See also Mendez et al., 1997, *Nature Genetics* 15:146-156, which is hereby incorporated by reference for any purpose.

The monoclonal antibodies (MAbs) of the invention can be produced by a variety of techniques, including conventional monoclonal antibody methodology, e.g., the standard somatic cell hybridization technique of Kohler and Milstein, 1975,

*Nature* 256:495. Although somatic cell hybridization procedures are preferred, in principle, other techniques for producing monoclonal antibodies can be employed, e.g., viral or oncogenic transformation of B-lymphocytes.

In a preferred embodiment, human monoclonal antibodies directed against IL-1R1 can be generated using mice referred to as "HuMab" mice, contain a human immunoglobulin gene minilocus that encodes unrearranged human heavy (μ and γ) and κ light chain immunoglobulin sequences, together with targeted mutations that inactivate the endogenous μ and κ chain loci. Lonberg et al., 1994, *Nature* 368:856-859. Accordingly, the mice exhibit reduced expression of mouse IgM or K and in response to immunization, the introduced human heavy and light chain transgenes undergo class switching and somatic mutation to generate high affinity human IgG κ monoclonal antibodies. Lonberg et al., supra; Lonberg and Huszar, 1995, *Intern. Rev. Immunol.* 13:65-93; Harding and Lonberg, 1995. *Ann. N.Y. Acad. Sci.* 764:536-546. The preparation of HuMab mice is described in detail in Taylor et al., 1992, *Nucleic Acids Res.* 20:6287-6295; Chen et al., 1993, *International Immunology* 1:647-656; Tuaillon et al., 1994, *J. Immunol.* 152:2912-2920; Lonberg et al., 1994, *Nature* 368: 856-859; Lonberg, 1994, *Handbook of Exp. Pharmacology* 113:49-101; Taylor et al., 1994, *International Immunology* 6:579-591; Lonberg & Huszar, 1995, *Intern. Rev. Immunol.* 13:65-93; Harding & Lonberg, 1995, *Ann. N.Y. Acad. Sci.* 764:536-546; Fishwild et al., 1996, *Nature Biotechnology* 14:845-851, the contents of all of which are hereby incorporated by reference in their entirety. See further U.S. Pat. Nos. 5,545,806; 5,569,825; 5.625,126; 5,633,425; 5,789,650; 5.877,397; 5,661,016; 5,814,318; 5,874,299; and 5,770,429; all to Lonberg and Kay, as well as U.S. Pat. No. 5,545,807 to Surani et al.; International Patent Application Publication Nos. WO 93/1227, published Jun. 24, 1993; WO 92/22646, published Dec. 23, 1992; and WO 92/03918, published Mar. 19, 1992, the disclosures of all of which are hereby incorporated by reference in their entirety. Alternatively, the HCo7 and HCo12 transgenic mice strains described in the Examples below can be used to generate human anti-IL-1R1 antibodies.

Advantageously, fully human monoclonal antibodies specific for IL-1R1 are produced as follows. Transgenic mice containing human immunoglobulin genes are immunized with the IL-1R1-related antigen of interest. Lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to IL-1R1 is provided.

In preferred embodiments, antibodies of the invention are produced by hybridoma lines. In these embodiments, the antibodies of the invention bind to IL-1R1 with a dissociation constant (IK) of between approximately 4 pM and 100 pM. In certain embodiments of the invention, the antibodies bind to IL-1R1 with a $K_d$ of less than about 20 pM. In other embodiments, the antibodies of the invention bind to the third domain of IL-1R1. The nucleotide and amino acid sequences of the third domain of human and rat IL-R1 are shown in FIG. 17.

In preferred embodiments, the antibodies of the invention are of the IgG1, IgG2, or IgG4 isotype, with the IgG2 isotype most preferred. In preferred embodiments of the invention, the antibodies comprise a human kappa light chain and a human IgG1, IgG2, or IgG4 heavy chain. In particular embodiments, the variable regions of the antibodies are ligated to a constant region other than the constant region for the IgG1, IgG2, or IgG4 isotype. In certain embodiments, the antibodies of the invention have been cloned for expression in mammalian cells.

In certain embodiments, conservative amino acid substitutions to the heavy and light chains of anti-IL-1R1 antibody (and corresponding modifications to the encoding nucleotides) will produce anti-IL-1R1 antibodies having functional and chemical characteristics similar to those of anti-IL-1R1 antibody. In contrast, substantial modifications in the functional and/or chemical characteristics of anti-IL-1R1 antibody may be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis" (Wells, 1991, *Methods Enzymol.* 202:390 (ed. J. J. Langone), Academic Press, London).

Desired amino acid substitutions (whether conservative or non-conservative) can be determined by those skilled in the art at the time such substitutions are desired. In certain embodiments, amino acid substitutions can be used to identify important residues of anti-IL-1R1 antibody, or to increase or decrease the affinity of the anti-IL-1R1 antibodies described herein.

In alternative embodiments, antibodies of the invention can be expressed in cell lines other than hybridoma cell lines. In these embodiments, sequences encoding particular antibodies can be used for transformation of a suitable mammalian host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Such procedures are exemplified by U.S. Pat. Nos. 4,399,216, 4,912,040, 4,740, 461, and 4,959,455 (all of which are hereby incorporated herein by reference for any purpose). Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

According to certain embodiments of the methods of the invention, a nucleic acid molecule encoding the amino acid sequence of a heavy chain constant region, a heavy chain variable region, a light chain constant region, or a light chain variable region of an IL-1R1 antibody of the invention is inserted into an appropriate expression vector using standard ligation techniques. In a preferred embodiment, the IL-1R1 heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, *Meth. Enzymiol. Vol.* 185, Academic Press. N.Y.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the IL-1R1 polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification or detection of the IL-1R1 antibody from the host cell. Affinity purification can be accomplished, for example, by column chromatography using antibodies against the tag as an affinity matrix. Optionally, the tag can subsequently be removed from the purified IL-1R1 polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Preferred selectable markers are the kanamycin resistance gene, the ampicillin resistance gene, and the tetracycline resistance gene. A neomycin resistance gene may also be used for selection in both prokaryotic and eukaryotic host cells.

Other selectable genes may be used to amplify the gene that will be expressed. Amplification is the process wherein genes that are in greater demand for the production of a protein critical for growth or cell survival are reiterated generally in tandem within the chromosomes of successive generations of recombinant cells. Examples of suitable selectable markers for mammalian cells include dihydrofolate reductase (DHFR) and promoterless thymidine kinase. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as IL-1R1 polypeptide comprising the vector. As a result, increased quantities of a polypeptide such as IL-1R1 polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

The expression and cloning vectors of the invention will typically contain a promoter that is recognized by the host organism and operably linked to the molecule encoding the anti-IL-1R1 antibody. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding heavy chain or light chain comprising an anti-IL-1R1 antibody of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: the SV40 early promoter region (Bernoist and Chambon, 1981, *Nature* 290:304-10); the CMV promoter, the promoter contained in the 3' long terminal repeat of Rous sarcoma virus (Yamamoto et al., 1980, *Cell* 22:787-97); the herpes thymidine kinase promoter (Wagner et al., 1981, *Proc. Natl. Acad. Sci. USA* 78:1444-45); the regulatory sequences of the metallothionine gene (Brinster et al., 1982, *Nature* 296:39-42); prokaryotic expression vectors such as the beta-lactamase promoter (VIIIa-Kamaroff et al., 1978, *Proc. Natl. Acad. Sci. USA* 75:3727-31); or the tac promoter (DeBoer et al., 1983, *Proc. Natl. Acad. Sci. USA* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region that is active in pancreatic beta cells (Hanahan, 1985, *Nature* 315:115-22); the immunoglobulin gene control region that is active in lymphoid cells (Grosschedl et al., 1984, *Cell* 38:647-58; Adames et al., 1985, *Nature* 318:533-38; Alexander et al., 1987, *Mol. Cell. Biol.* 7:1436-44); the mouse mammary tumor virus control region that is active in testicular, breast, lymphoid and mast cells (Leder et al., 1986, *Cell* 45:485-95); the albumin gene control region that is active in liver (Pinkert et al., 1987, *Genes and Devel.* 1:268-76); the alpha-fetoprotein gene control region that is active in liver (Krumlauf et al., 1985, *Mol. Cell. Biol.* 5:1639-48; Hammer et al., 1987, *Science* 235:53-58); the alpha 1-antitrypsin gene control region that is active in liver (Kelsey et al., 1987, *Genes and Devel.* 1:161-71); the beta-globin gene control region that is active in myeloid cells (Mogram et al., 1985, *Nature* 315:338-40; Kollias et al., 1986, *Cell* 46:89-94); the myelin basic protein gene control region that is active in oligodendrocyte cells in the brain (Readhead et al., 1987, *Cell* 48:703-12); the myosin light chain-2 gene control region that is active in skeletal muscle (Sani, 1985, *Nature* 314:283-86); and the gonadotropic releasing hormone gene control region that is active in the hypothalamus (Mason et al., 1986, *Science* 234:1372-78).

An enhancer sequence may be inserted into the vector to increase transcription of DNA encoding light chain or heavy chain comprising an anti-IL-1R1 antibody of the invention by higher eukaryotes. Enhancers are cis-acting elements of DNA, usually about 10-300 bp in length, that act on the promoter to increase transcription. Enhancers are relatively orientation- and position-independent. They have been found 5' and 3' to the transcription unit. Several enhancer sequences available from mammalian genes (e.g., globin, elastase, albumin, alpha-feto-protein and insulin) are known. Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be spliced into the vector at a position 5' or 3' to a nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain or heavy chain or light chain and heavy chain comprising an anti-IL-1R1 antibody has been inserted into the proper site of the vector, the completed vector may be inserted into a suitable host cell for amplification and/or polypeptide expression. The transformation of an expression vector for an anti-IL-1R1 antibody into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

The host cell, when cultured under appropriate conditions, synthesizes an anti-IL-1R1 antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (A.T.C.C.), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, one may select cell lines by determining which cell lines have high expression levels and produce antibodies with constitutive IL-1R1 binding properties. In another embodiment, one may select a cell line from the B cell lineage that does not make its own antibody but has a capacity to make and secrete a heterologous antibody (e.g., mouse myeloma cell lines NS0 and SP2/0).

Antibodies of the invention are useful for detecting IL-1R1 in biological samples and identification of cells or tissues that produce IL-1R1 protein. Said antibodies that bind to IL-1R1 and block interaction with other binding compounds have therapeutic use in modulating IL-1 mediated diseases. In preferred embodiments, antibodies to IL-1R1 can block IL-1R1 binding to IL-1β or IL-1a, which can result in disruption of the IL-1 signal transduction cascade.

Antibodies of the invention that specifically bind to IL-1R1 may be useful in treatment of IL-1 mediated diseases, as discussed below. Said antibodies can be used in binding assays to detect IL-1R1 binding and their capacity to inhibit IL-1R1 from forming a complex with IL-1β and IL-1R accessory protein (IL-1RAcP) or with IL-1α and IL-1RacP.

In certain embodiments, the invention provides methods for treating medical disorders associated with IL-1 mediated inflammatory reactions or IL-1 mediated immunoregulatory reactions. The methods of the invention include administering an anti-IL1R1 antibody of the invention to an individual who is afflicted with an inflammatory or immunoregulatory disease that is mediated by IL-1. As used herein, the terms "illness," "disease," "medical condition," or "abnormal condition," are used interchangeably with the term "medical disorder."

In a particular embodiment, the methods of the invention involve administering to a patient an anti-IL-1R1 antibody of the invention, thereby preventing the binding of IL-1 to its cell surface receptor (IL-1R1).

To treat a medical disorder characterized by abnormal or excess expression of IL-1 or abnormal or excess IL-1 signaling, a molecule comprising an IL-1R type I antibody of this invention is administered to the patient in an amount and for a time sufficient to induce a sustained improvement in at least one indicator that reflects the severity of the disorder. An improvement is considered "sustained" if the patient exhibits the improvement on at least two occasions separated by one to four weeks. The degree of improvement is determined based on signs or symptoms, and may also employ questionnaires that are administered to the patient, such as quality-of-life questionnaires.

Various indicators that reflect the extent of the patient's illness may be assessed for determining whether the amount and time of the treatment is sufficient. The baseline value for the chosen indicator or indicators is established by examination of the patient prior to administration of the first dose of the antibody. Preferably, the baseline examination is done within about 60 days of administering the first dose. If the IL-1R antibody is being administered to treat acute symptoms, such as, for example, to treat traumatic injuries (traumatic knee injury, stroke, head injury, etc.) the first dose is administered as soon as practically possible after the injury or event has occurred.

Improvement is induced by repeatedly administering a dose of antibody until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions.

Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

Any efficacious route of administration may be used to therapeutically administer the antibody. The antibody may be injected via intra-articular, intravenous, intramuscular, intralesional, intraperitoneal, intracranial, inhalation or subcutaneous routes by bolus injection or by continuous infusion. For example, pulmonary diseases can involve intranasal and inhalation methods. Other suitable means of administration include sustained release from implants, aerosol inhalation, eyedrops, oral preparations, including pills, syrups, lozenges or chewing gum, and topical preparations such as lotions, gels, sprays, ointments or other suitable techniques. Administration by inhalation is particularly beneficial when treating diseases associated with pulmonary disorders.

In one embodiment of the invention, an anti-IL-1R1 antibody of the invention can be administered once a month. In another embodiment the antibody is administered once every two weeks or one time per week to treat the various medical disorders disclosed herein. In yet another embodiment the antibody is administered at least two times per week, and in another embodiment is administered at least once per day. An adult patient is a person who is 18 years of age or older. If injected, the effective amount, per adult dose, ranges from 1-200 mg/m$^2$, or from 1-40 mg/m$^2$ or about 5-25 mg/m$^2$. Alternatively, a flat dose may be administered, whose amount may range from 2-400 mg/dose, 2-100 mg/dose or from about 10-80 mg/dose. If the dose is to be administered more than one time per week, an exemplary dose range is the same as the foregoing described dose ranges or lower. In one embodiment of the invention, the various indications described below are treated by administering a preparation acceptable for injection containing IL-1 receptor antibody at 80-100 mg/dose, or alternatively, containing 80 mg per dose. The dose is administered repeatedly. If a route of administration other than injection is used, the dose is appropriately adjusted in accord with standard medical practices. For example, if the route of administration is inhalation, dosing may be one to seven times per week at dose ranges from 10 mg/dose to 50 mg per dose.

In preferred embodiments, the invention also provides pharmaceutical compositions comprising a therapeutically effective amount of one or a plurality of the antibodies of the invention together with a pharmaceutically acceptable diluent, carrier, solubilizer, emulsifier, preservative and/or adjuvant. Preferably, acceptable formulation materials are nontoxic to recipients at the dosages and concentrations employed. In preferred embodiments, pharmaceutical compositions comprising a therapeutically effective amount of anti-IL-1R1 antibodies are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris- HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, trimethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, *Remington's Pharmaceutical Sciences*, 18$^{th}$ Edition, (A. R. Gennaro. ed.), 1990, Mack Publishing Company.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, anti-IL-1R1 antibody compositions may be prepared for storage by mixing the selected composition having the desired degree of purity with optional formulation agents (Remington's Pharmaceutical Sciences, supra) in the form of a lyophilized cake or an aqueous solution. Further, in certain embodiments, the anti-IL-1R1 antibody product may be formulated as a lyophilizate using appropriate excipients such as sucrose.

The pharmaceutical compositions of the invention can be selected for parenteral delivery. The compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired anti-IL-1R1 antibody in a pharmaceutically acceptable vehicle. A particularly suitable vehicle for parenteral injection is sterile distilled water in which the anti-IL-1R1 antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, anti-IL-1R1 antibodies are formulated as a dry powder for inhalation. In preferred embodiments, anti-IL-1R1 antibody inhalation solutions may also be formulated with a propellant for aerosol delivery. In certain embodiments, solutions may be nebulized. Pulmonary administration and formulation methods therefore are further described in International Patent Publication No. WO94/20069, incorporated by reference, which describes pulmonary delivery of chemically modified proteins.

It is also contemplated that formulations can be administered orally. Anti-IL-1R1 antibodies that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the anti-IL-1R1 antibody. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of anti-IL-1R1 antibodies in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving anti-IL-1R1 antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, International Patent Publication No. WO93/15722, incorporated by reference, which describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, *Biopolymers* 22:547-556), poly (2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent Application Publication No. EP 133,988). Sustained release compositions may also include liposomes that can be prepared by any of several methods known in the art. See e.g., Eppstein et al., 1985, *Proc. Natl. Acad. Sci. USA* 82:3688-3692; European Patent Application Publication Nos. EP 036,676; EP 088,046 and EP 143,949.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The effective amount of an anti-IL-1R1 antibody-containing pharmaceutical composition to be employed therapeutically will depend, for example, upon the therapeutic context and objectives. One skilled in the art will appreciate that the appropriate dosage levels for treatment will vary depending, in part, upon the molecule delivered, the indication for which the anti-IL-1R1 antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 μg/kg to up to about 100 mg/kg or more, depending on the factors mentioned above. In preferred embodiments, the dosage may range from 0.1 μg/kg up to about 100 mg/kg; more preferably from 1 μg/kg up to about 100 mg/kg; or even more preferably from 5 μg/kg up to about 100 mg/kg.

Dosing frequency will depend upon the pharmacokinetic parameters of the particular anti-IL-1R1 antibody in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use anti-IL-1R1 antibody pharmaceutical compositions according to the invention ex vivo. In such instances, cells, tissues or organs that have been removed from the patient are exposed to anti-IL-1R1 antibody pharmaceutical compositions after which the cells, tissues and/or organs are subsequently implanted back into the patient.

In particular, anti-IL-1R1 antibodies can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

In certain embodiments, the invention further encompasses the administration of an anti-IL-1R1 antibody or pharmaceutical composition of the invention concurrently with one or more other drugs that are administered to the same patient, each drug being administered according to a regimen suitable for that medicament. This encompasses pre-treatment, simultaneous treatment, sequential treatment and alternating regimens. Examples of such drugs include, but are not limited to, antivirals, antibiotics, analgesics, corticosteroids, antagonists of inflammatory cytokines, disease-modifying anti-rheumatic drugs (DMARDs), and non-steroidal anti-inflammatories.

In other embodiments, an anti-IL-1R1 antibody or pharmaceutical composition of the invention can be administered in combination with other cytokine inhibitors, including those that antagonize, for example, RANKL, TGFβ, IFNγ, IL-6 or IL-8 and TNF, particularly TNFα. In combination with IL-6, an antibody of this invention can be used to treat and prevent the recurrence of seizures, including seizures induced by $GABA_A$ receptor antagonism, seizures associated with EEG ictal episodes and motor limbic seizures occurring during status epilepticus. In combination with IFNγ inhibitor, an antibody of this invention is useful in treating idiopathic pulmonary fibrosis and cystic fibrosis. The combination of an IL-1 receptor antibody and RANKL inhibitors, e.g. a RANKL antibody is useful for preventing bone destruction in various settings including but not limited to various rheumatic disorders, osteoporosis, multiple myeloma or other malignancies that cause bone degeneration, or anti-tumor therapy aimed at preventing metastasis to bone, or bone destruction associated with prosthesis wear debris or with periodontitis. In addition, antibodies of the invention may be administered in combination with IL-17 inhibitors such soluble forms of an IL-17 receptor (such as IL-17R:Fc) or an IL-17 antibody or IL-17R antibody, IL-18 binding protein, soluble forms of IL-18 receptors, and IL-18 antibodies, antibodies against IL-18 receptors or antibodies against CD30-ligand or against CD4.

The invention further encompasses methods for using an anti-IL1R1 antibody or pharmaceutical composition of the invention in treating the herein disclosed medical disorders in combination with a TNF inhibitor, preferably TNFR:Fc (ENBREL®) and any combination of the above described cytokines or cytokine inhibitors that are active agents in combination therapies. For example, in accordance with the present invention, combination therapy methods may be used for treating rheumatoid arthritis, stroke, asthma, psoriasis, etc.

Conditions effectively treated by an anti-IL-1R1 antibody or pharmaceutical composition described herein include pulmonary diseases such as asthma, chronic obstructive pulmonary disease, pulmonary alveolar proteinosis, bleomycin-induced pneumopathy and fibrosis, radiation-induced pulmonary fibrosis, cystic fibrosis, collagen accumulation in the lungs, and ARDS, all of which may be treated with combinations of an antibody to IL-1R and an IL-4 inhibitor and/or IL-13 inhibitor, e.g. IL-4R antibody that inhibits IL-13 and IL-4 activity. The disclosed antibodies and pharmaceutical compositions of the invention also are useful for treating broncho-pulmonary dysplasia (BPD); chronic obstructive pulmonary diseases (e.g. emphysema and chronic bronchitis), and chronic fibrotic lung disease of preterm infants. In addition, the compounds, compositions and combination therapies of the invention are used to treat occupational lung diseases, including asbestosis, coal worker's pneumoconiosis, silicosis or similar conditions associated with long-term exposure to fine particles. In other aspects of the invention, the disclosed compounds, compositions and combination therapies are used to treat bronchioliterans organizing pneumonia, pulmonary fibrosis, including idiopathic pulmonary fibrosis and radiation-induced pulmonary fibrosis; pulmonary sarcoidosis; and allergies, including allergic rhinitis, contact dermatitis, atopic dermatitis and asthma.

Such combinations are useful also for treating patients suffering from various skin disorders, including but not limited to dermatitis herpetiformis (Duhring's disease), atopic dermatitis, contact dermatitis, urticaria (including chronic idiopathic urticaria), and autoimmune blistering diseases, including pemphigus vulgaris and bullous pemphigoid. Other diseases treatable with the combination of an IL-1R antibody and an IL-4 and/or IL-13 inhibitor include myesthenia gravis, sarcoidosis, including pulmonary sarcoidosis, scleroderma, reactive arthritis, hyper IgE syndrome, multiple sclerosis and idiopathic hypereosinophil syndrome. The combination is used also for treating allergic reactions to medication and as an adjuvant to allergy immunotherapy.

The IL-1 receptor antibodies and pharmaceutical compositions described herein are useful for treating protozoal diseases, including malaria and schistosomiasis and to treat erythema nodosum leprosum; bacterial or viral meningitis; tuberculosis, including pulmonary tuberculosis; and pneumonitis secondary to a bacterial or viral infection including influenza infection and infectious mononucleosis.

Cardiovascular disorders and injuries are treatable and/or preventable with disclosed either pharmaceutical compositions or anti-IL1-R1 antibodies alone or in combination with other cytokine inhibitors. Cardiovascular disorders treatable include aortic aneurysms; including abdominal aortic aneurysms, acute coronary syndrome, arteritis; vascular occlusion, including cerebral artery occlusion; complications of coronary by-pass surgery; ischemia/reperfusion injury; heart disease, including atherosclerotic heart disease, myocarditis, including chronic autoimmune myocarditis and viral myocarditis; heart failure, including chronic heart failure, congestive heart failure, cachexia of heart failure; myocardial infarction; restenosis and/or atherosclerosis after heart surgery or after carotid artery balloon angioplastic procedures; silent myocardial ischemia; left ventricular pump dysfunction, post implantation complications of left ventricular assist devices; Raynaud's phenomena; thrombophlebitis; vasculitis, including Kawasaki's vasculitis; veno-occlusive disease, giant cell arteritis, Wegener's granulomatosis; mental confusion following cardio pulmonary by pass surgery, and Schoenlein-Henoch purpura.

In certain embodiments, anti-IL-1R1 antibodies and pharmaceutical compositions of the invention can also be used to treat chronic pain conditions, such as chronic pelvic pain, including chronic prostatitis/pelvic pain syndrome, and post-herpetic pain.

Disorders of the endocrine system including juvenile onset diabetes (includes autoimmune diabetes mellitus and insulin-dependent types of diabetes) and maturity onset diabetes (includes non-insulin dependent and obesity-mediated diabetes) can also be treated with anti-IL-1R1 antibodies or pharmaceutical compositions of the invention. Such treatment includes secondary conditions associated with diabetes, such as diabetic retinopathy, kidney transplant rejection in diabetic patients, obesity-mediated insulin resistance, and renal failure, which itself may be associated with proteinurea and hypertension. Other endocrine disorders also are treatable with these compounds and include polycystic ovarian disease, X-linked adrenoleukodystrophy, hypothyroidism and thyroiditis, including Hashimoto's thyroiditis (i.e., autoimmune thyroiditis), thyroid cell dysfunction, including euthyroid sick syndrome.

Conditions of the gastrointestinal system are treatable or preventable with anti-IL-1R1 antibodies or pharmaceutical compositions of the invention, alone or in combination with other therapeutics. These conditions include coeliac disease, Crohn's disease; ulcerative colitis; idiopathic gastroparesis; pancreatitis, including chronic pancreatitis; acute pancreatitis, inflammatory bowel disease and ulcers, including gastric and duodenal ulcers.

Disorders of the genitourinary system are also treatable or preventable with the anti-IL-1R1 antibodies or pharmaceutical compositions described herein. Such disorders include glomerulonephritis, including autoimmune glomerulonephritis, glomerulonephritis due to exposure to toxins or glomerulonephritis secondary to infections with haemolytic streptococci or other infectious agents. Also treatable with the compounds, compositions and combination therapies of the invention are uremic syndrome and its clinical complications (for example, renal failure, anemia, and hypertrophic cardiomyopathy), including uremic syndrome associated with exposure to environmental toxins, drugs or other causes. Complications that arise from inflammation of the gallbladder wall that leads to alteration in absorptive function are treatable or preventable with the antibodies of this invention. Included in such complications are cholelithiasis (gallstones) and choliedocholithiasis (bile duct stones) and the recurrence of cholelithiasis and choliedocholithiasis. Further conditions treatable with the compounds, compositions and combination therapies of the invention are complications of hemodialysis; prostate conditions, including benign prostatic hypertrophy, nonbacterial prostatitis and chronic prostatitis; and complications of hemodialysis.

Also provided herein are methods for using anti-IL-1R1 antibodies of the invention, compositions, and combination therapies to treat various hematologic and oncologic disorders. For example, anti-IL-1R1 antibodies, alone or in combination with other cytokine inhibitors or other active agents as described above, can be used to treat various forms of cancer, including acute myelogenous leukemia, chronic myelogenous leukemia leukemia, Epstein-Barr virus-positive nasopharyngeal carcinoma, glioma, colon, stomach, prostate, renal cell, cervical and ovarian cancers, lung cancer (SCLC and NSCLC), including cancer-associated cachexia, fatigue, asthenia, paraneoplastic syndrome of cachexia and hypercalcemia. Solid tumors, including sarcoma, osteosarcoma, and carcinoma, such as adenocarcinoma (for example, breast cancer) and squamous cell carcinoma are also treatable. Additional treatable cancers include esophogeal cancer, gastric cancer, gall bladder carcinoma, leukemia, including acute myelogenous leukemia, chronic myelogenous leukemia, myeloid leukemia, chronic or acute lymphoblastic leukemia and hairy cell leukemia. Other malignancies with invasive metastatic potential, including multiple myeloma, can be treated with the subject compounds, compositions and combination therapies.

In addition, the disclosed anti-IL-1R1 antibodies can be used to treat anemias and hematologic disorders, including chronic idiopathic neutropenia, anemia of chronic disease, aplastic anemia, including Fanconi's aplastic anemia; idiopathic thrombocytopenic purpura (ITP); thrombotic thrombocytopenic purpura, myelodysplastic syndromes (including refractory anemia, refractory anemia with ringed sideroblasts, refractory anemia with excess blasts, refractory anemia with excess blasts in transformation); myelofibrosis/myeloid metaplasia; and sickle cell vasocclusive crisis.

Various lymphoproliferative disorders also are treatable with anti-IL-1R1 antibodies of the invention, including autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma. Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Sézary syndrome.

Hereditary conditions such as Gaucher's disease, Huntington's disease, linear IgA disease, and muscular dystrophy are treatable with the antibodies of this invention.

Other conditions treatable or preventable by the disclosed IL-1 receptor antibodies or pharmaceutical compositions include those resulting from injuries to the head or spinal cord including subdural hematoma due to trauma to the head. In connection with this therapy, the compositions and combinations described are suitable for preventing cranial neurologic damage and preventing and treating cervicogenic headache. The compositions and combinations described are further suitable for treating neurological side effects associated with brain irradiation.

Anti-IL-1R1 antibodies and pharmaceutical composition of the invention are also useful for treating conditions of the liver such as hepatitis, including acute alcoholic hepatitis, acute drug-induced or viral hepatitis, hepatitis A, B and C, sclerosing cholangitis, hepatic sinusoid epithelium, and inflammation of the liver due to unknown causes.

Disorders that involve hearing loss and that are associated with abnormal IL-expression are treatable with the anti-IL-1R1 antibodies or pharmaceutical compositions of the invention. Such disorders include cochlear nerve-associated hearing loss that is thought to result from an autoimmune process, i.e., autoimmune hearing loss. Also treatable or preventable with the anti-IL-1R1 antibodies or pharmaceutical compositions of the invention is Meniere's syndrome and cholesteatoma, a middle ear disorder often associated with hearing loss.

Non-arthritic disorders of the bones and joints and also treatable with the antibodies described herein. This encompasses osteoclast disorders that lead to bone loss, such as but not limited to osteoporosis, including post-menopausal osteoporosis, osteoarthritis, periodontitis resulting in tooth loosening or loss, and prosthesis loosening after joint replacement (generally associated with an inflammatory response to wear debris). This latter condition also is called "orthopedic implant osteolysis." Another condition treatable with the compounds, compositions and combination therapies of the invention is temporal mandibular joint dysfunction (TMJ).

The anti-IL-1R1 antibodies or pharmaceutical compositions of the invention can also be used to treat rheumatic disorders including adult and juvenile rheumatoid arthritis; scleroderma; systemic lupus erythematosus; gout; osteoarthritis; polymyalgia rheumatica; scronegative spondylarthropathies, including ankylosing spondylitis, and Reiter's disease, psoriatic arthritis and chronic Lyme arthritis. The antibodies of this invention are also useful for treating nflammation of the voluntary muscle and other muscles, including dermatomyositis, inclusion body myositis, polymyositis, and lymphangioleimyomatosis.

Another use for the antibodies and pharmaceutical compositions of the invention is the treatment and/or prevention of primary amyloidosis and the secondary amyloidosis that is characteristic of various condition including Alzheimer's disease, secondary reactive amyloidosis; Down's syndrome; and dialysis-associated amyloidosis. Also treatable with the antibodies or pharmaceutical compositions of the invention are inherited periodic fever syndromes, including familial Mediterranean fever, hyperimmunoglobulin D and periodic fever syndrome and TNF-receptor associated periodic syndromes (TRAPS).

In other embodiments, the antibodies or pharmaceutical compositions of the invention can be used to treat disorders involving the skin or mucous membranes. Such disorders include acantholytic diseases, including Darier's disease, keratosis follicularis and pemphigus vulgaris. Additional skin disorders that can be treated using antibodies of the invention include acne, acne rosacea, alopecia greata, aphthous stomatitis, bullous pemphigoid, burns, eczema, erythema, including erythema multiforme and erythema multiforme bullosum (Stevens-Johnson syndrome), inflammatory skin disease, lichen planus, linear IgA bullous disease (chronic bullous dermatosis of childhood), loss of skin elasticity, mucosal surface ulcers, including gastric ulcers, neutrophilic dermatitis (Sweet's syndrome), dermatomyositis, pityriasis rubra pilaris, psoriasis, pyoderma gangrenosum, multicentric reticulohistiocytosis, and toxic epidermal necrolysis. Other skin related conditions treatable by the therapies and combination therapies of the present invention include dermatitis herpetiformis.

Additional disorders that can be treated with the antibodies or pharmaceutical compositions of the invention include graft-versus-host disease, and complications resulting from solid organ transplantation, such as heart, liver, skin, kidney, lung (lung transplant airway obliteration) or other transplants, including bone marrow transplants.

Ocular disorders also are treatable or preventable with the disclosed anti-IL-1R1 antibodies or pharmaceutical compositions, including rhegmatogenous retinal detachment, and inflammatory eye disease, including inflammatory eye disease associated with smoking and macular degeneration.

Antibodies or pharmaceutical compositions of the invention, as described herein, are useful for treating disorders that affect the female reproductive system. Examples include, but are not limited to, multiple implant failure/infertility; fetal loss syndrome or IV embryo loss (spontaneous abortion); preeclamptic pregnancies or eclampsia; endometriosis, chronic cervicitis, and pre-term labor.

In addition, the antibodies or pharmaceutical compositions of the invention are useful for treating and/or preventing sciatica, symptoms of aging, severe drug reactions (for example, Il-2 toxicity or bleomycin-induced pneumopathy and fibrosis), or to suppress the inflammatory response prior, during or after the transfusion of allogeneic red blood cells in cardiac or other surgery, or in treating a traumatic injury to a limb or joint, such as traumatic knee injury. Various other medical disorders treatable with the disclosed anti-IL-1R1 antibodies or pharmaceutical compositions include; multiple sclerosis; Behcet's syndrome; Sjogren's syndrome; autoimmune hemolytic anemia; beta thalassemia; amyotrophic lateral sclerosis (Lou Gehrig's Disease); Parkinson's disease; and tenosynovitis of unknown cause, as well as various autoimmune disorders or diseases associated with hereditary deficiencies, including x-linked mental retardation.

Furthermore, the anti-IL-1R1 antibodies or pharmaceutical compositions of the invention are useful for treating central nervous system (CNS) injuries, including the effects of neurotoxic neurotransmitters discharged during excitation of inflammation in the central nervous system and to inhibit or prevent the development of glial scars at sites of central nervous system injury. In connection with epilepsy and the treatment of seizures, reducing the severity and number of recurring seizures, and reducing the severity of the deleterious effects of seizures, reducing neuronal loss, neuronal degeneration, and gliosis associated with seizures.

Additional uses for the antibodies or pharmaceutical compositions of the invention include, but are limited to, treating critical illness polyneuropathy and myopathy (CIPNM) acute polyneuropathy; anorexia nervosa; Bell's palsy; chronic fatigue syndrome; transmissible dementia, including Creutzfeld-Jacob disease; demyelinating neuropathy; Guillain-Barre syndrome; vertebral disc disease; Gulf war syndrome; chronic inflammatory demyelinating polyneuropathy, myasthenia gravis; silent cerebral ischemia; sleep disorders, including narcolepsy and sleep apnea; chronic neuronal degeneration; and stroke, including cerebral ischemic diseases. Still additional uses for the antibodies of the invention are anorexia and/or anorexic conditions, peritonitis, endotoxemia and septic shock, granuloma formation, heat stroke, Churg-Strauss syndrome, chronic inflammation following acute infections such as tuberculosis and leprosy, systemic sclerosis and hypertrophic scarring.

In other embodiments, avidin fusion proteins comprising an amino acid sequence of one of the IL-1R1 antibodies of the invention can be constructed for various purposes. Avidin fusion proteins can be generated, for example, using a mammalian expression vector containing cDNA sequence encoding recombinant chicken avidin adjacent to a multiple cloning site for insertion of a specific target gene fusion partner. The vector can include an avidin sequence with its endogenous signal sequence to enable secretion of discrete fusion gene partners that do not naturally contain signal sequences. The fusion protein expressed by the vector has an avidin protein tag at the N-terminal portion of the fusion partner. The fusion strategy as described herein has the capability of secreting proteins that are normally expressed intracellularly, such as signal transduction genes or nuclear hormone receptors.

Alternatively, a vector can be used that encodes avidin without its endogenous signal sequence, which will result in C-terminal tagging of fusion protein partners. A C-terminal avidin fusion also allows for protein secretion based on the endogenous signal sequence of the fusion partner. Such a strategy can be applied to allow for correct protein processing and folding or to determine validity of a proposed signal sequence. Additionally, the vector can comprise a short nucleotide sequence encoding an amino acid sequence, which can act as a specific enzyme-cleavable substrate, between the avidin and fusion partner sequences. Such enzyme-cleavable sequences allow for separation of the fusion partner from the avidin for purification or protein release purposes.

Avidin fusion proteins of the invention can be used, for example, in antibody screening, functional characterization (determination of an antibody's utility as an agonist or antagonist, neutralizing agent, etc.), epitope mapping, or immunization strategies. Avidin fusions of a target protein can also be utilized in pharmokinetic, efficacy or other standard assay formats designed to test preclinical samples or clinical patient samples for the presence of the therapeutic antibody in blood, urine, or other tissue samples. Avidin fusion protein partners can be prepared as full-length or truncated sequences, specific isolated structural domains, or as chimeric sequences with other homologs of the fusion partner from other species.

Avidin fusion proteins can be expressed using any standard means of introducing genes into cells, as described herein and known in the art. The proteins can be expressed in, for example, 293 or CHO cells by transfecting the cells with an avidin fusion construct in a solution of lipids, such as in Lipofectamine (Invitrogen, Carlsbad, Calif.).

Conditioned media and/or cell lysates from cells expressing the fusion proteins can be collected and applied to an assay substrate, such as biotin-coated polystyrene beads or biotin-coated ELISA plates. Collecting the conditioned media and/or cell lysate can be conducted at a time point that allows for optimum expression of the fusion protein. The time point can be determined experimentally by those skilled in the art, but is usually about 48 hours post-transfection. Fusion proteins can also be analyzed at the cell membrane or intracellularly for expression and functionality in binding known ligands, receptors, or antibodies.

Avidin fusion proteins of the invention can be analyzed by any known or previously characterized method that utilizes biotin-avidin interactions. Such methods include, but are not limited to, flow cytometry and fluorescent imaging/microscopy. For example, avidin fusions expressed in media or cell lysates can be applied to biotin-coated beads and stained with a fluorescently tagged anti-avidin antibody to indicate expression level. Also, fluorescent antibodies can be applied that recognize the specific fusion protein partner in a multi-colorimetric assay format. Additionally, unlabeled antibodies specific for the fusion protein partner can be applied simultaneously with fluorescently tagged antibodies in a competition assay.

In certain embodiments, the invention provides methods for mapping epitopes using avidin fusion proteins. An example of an epitope mapping method of the invention is provided below with respect to mapping epitopes for anti-IL-1R1 antibodies. However, one of skill in the art will recognize that such methods can be readily applied to mapping epitopes for any antibody and is not limited to anti-IL-1R1 antibodies. For example, cDNA encoding chicken avidin (with endogenous signal sequence) can be joined with the 5' end of cDNAs encoding a protein of interest (i.e. a protein that is recognized by antibodies for which determining an epitope is desired) fused to a FLAG-tag sequence at the 3' end. The FLAG-tagged fusion genes can be assembled in an expression vector using conventional molecular techniques. A panel of mutant avidin-FLAG tagged proteins in which certain amino acids have been substituted (e.g., with corresponding amino acid residues from another animal species) can be generated using conventional techniques. The mutant and wild type proteins can be expressed in host cells and binding of the wild-type or mutant proteins with an antibody of interest can be detected using, for example, Western blot analysis or bead-based binding assays as described herein. Thus, an epitope can be defined by determining which substitutions in the mutant proteins destroy binding to the antibody of interest.

EXAMPLES

The following examples, including the experiments conducted and results achieved are provided for illustrative purposes only and are not to be construed as limiting the invention.

Example 1

Production of Human Monoclonal Antibodies Against Interleukin-1 Receptor Type I (IL-1R1)

Transgenic HuMab Mice

Fully human monoclonal antibodies to IL-1 receptor type I (IL-1R1) were prepared using the HCo7 strain of transgenic mice, which expresses human antibody genes. In each of these mouse strains, the endogenous mouse kappa light chain gene has been homozygously disrupted as described in Chen et al. (1993, *EMBO J.* 12:811-820), and the endogenous mouse heavy chain gene has been homozygously disrupted as described in Example 1 of International Patent Application Publication No. WO 01/09187 (incorporated by reference). Each of these mouse strains carries a human kappa light chain transgene, KCo5, as described in Fishwild et al. (1996, *Nature Biotechnology* 14:845-851). The HCo7 strain carries the HCo7 human heavy chain transgene as described in U.S. Pat. Nos. 5,545,806; 5,625,825; and 5,545,807 (incorporated by reference). The HCo7 strain is referred to herein as HuMab mice.

HuMab Immunizations

To generate fully human monoclonal antibodies to IL-1R1, HuMab mice were immunized with purified recombinant IL-1R1 derived from insect or mammalian cells (for example, CHO cells) as antigen. General immunization schemes for HuMab mice are described in Lonberg et al. (1994, *Nature* 368:856-859; Fishwild et al., supra; and International Patent Application Publication No. WO 98/24884, the teachings of each of which are incorporated by reference). Mice were 6-16 weeks of age upon the first infusion of antigen. A purified recombinant preparation (25-50 μg) of IL-1R1 antigen (e.g., purified from transfected insect or mammalian cells expressing IL-1R1) was used to immunize the HuMab mice intraperitoneally (IP) or subcutaneously (Sc).

Immunizations of HuMab transgenic mice were achieved using antigen in complete Freund's adjuvant and two injections, followed by 2-4 weeks IP immunization (up to a total of 11 immunizations) with the antigen in incomplete Freund's adjuvant. Several dozen mice were immunized for each antigen. A total of 149 mice of the HCo7 strain were immunized with IL-1R1. The immune response was monitored by retro-orbital bleeds.

To select HuMab mice producing antibodies that bound IL-1R1, sera from immunized mice were tested by ELISA as described by Fishwild et al., supra. Briefly, microtiter plates were coated with purified recombinant IL-1R1 from insect or mammalian cells at 1-2 μg/mL in PBS and 50 μL/well incubated at 4° C. overnight, then blocked with 200 μL/well of 5% chicken serum in PBS/Tween (0.05%). Dilutions of plasma from IL-1R1-immunized mice were added to each well and incubated for 1-2 hours at ambient temperature. The plates were washed with PBS/Tween and then incubated with a goat-anti-human IgG Fc-specific polyclonal reagent conjugated to horseradish peroxidase (HRP) for 1 hour at room temperature. Plates were washed with PBS/Tween and incubated with a goat anti-human IgG Fc-specific polyclonal reagent conjugated to horseradish peroxidase (HRP) for 1 hour at room temperature. After washing, the plates were developed with ABTS substrate (Sigma Chemical Co., St. Louis, Mo., Catalog No. A-1888, 0.22 mg/mL) and analyzed spectrophotometrically at OD of 415-495. Mice with sufficient titers of anti-IL-1R1 human immunoglobulin were used to produce monoclonal antibodies as described below.

Generation of Hebridomas Producing Human Monoclonal Antibodies to IL-1R1

Mice were prepared for monoclonal antibody production by boosting with antigen intravenously 2 days before sacrifice, and spleens were removed thereafter. The mouse splenocytes were isolated from the HuMab mice and fused with PEG to a mouse myeloma cell line using standard protocols. Typically, 20-30 fusions for each antigen were performed.

Briefly, single cell suspensions of splenic lymphocytes from immunized mice were fused to one-fourth the number of P3×63-Ag8.653 nonsecreting mouse myeloma cells (A.T.C.C., Accession No. CRL 1580) or SP2/0 nonsecreting mouse myeloma cells (A.T.C.C., CRL 1581) with 50% PEG (Sigma). Cells were plated at approximately $1 \times 10^5$/well in flat bottom microtiter plates, followed by about a two week incubation in selective medium containing 10% fetal bovine serum, 10% P388D1-(A.T.C.C., Accession No. CRL TIB-63) conditioned medium, 3-5% origen (IGEN) in DMEM (Mediatech, Catalog No. CRL 10013, with high glucose, L-glutamine and sodium pyruvate) plus 5 mM HEPES, 0.055 mM 2-mercaptoethanol, 50 mg/mL gentamycin and 1×HAT (Sigma, Catalog No. CRL P-7185). After 1-2 weeks, cells were cultured in medium in which the HAT was replaced with HT.

The resulting hybridomas were screened for the production of antigen-specific antibodies. Individual wells were screened by ELISA (described above) for human anti-IL-1R1 monoclonal IgG antibodies. Once extensive hybridoma growth occurred, medium was monitored usually after 10-14 days. Antibody-secreting hybridomas were replated, screened again and, if still positive for human IgG, anti-IL-1R1 monoclonal antibodies were subcloned at least twice by limiting dilution. The stable subclones were then cultured in vitro to generate small amounts of antibody in tissue culture medium for characterization.

Selection of Human Monoclonal Antibodies Binding to IL-1R1

An ELISA assay as described above was used to screen for hybridomas that showed positive reactivity with IL-1R1 immunogen. Hybridomas secreting a monoclonal antibody that bound with high avidity to IL-1R1 were subcloned and further characterized. One clone from each hybridoma, which retained the reactivity of parent cells (as determined by ELISA), was chosen for making a 5-10 vial cell bank stored in liquid nitrogen.

An isotype-specific ELISA was performed to determine the isotype of the monoclonal antibodies produced as disclosed herein. In these experiments, microtiter plate wells were coated with 50 μL/well of a solution of 1 μg/mL of mouse anti-human kappa light chain in PBS and incubated at 4° C. overnight. After blocking with 5% chicken serum, the plates were reacted with supernatant from each tested monoclonal antibody and a purified isotype control. Plates were incubated at ambient temperature for 1-2 hours. The wells were then reacted with either human IgG1, IgG2 or IgG4-specific horseradish peroxidase-conjugated goat anti-human polyclonal antisera and plates were developed and analyzed as described below.

Monoclonal antibodies purified from hybridoma supernatants that showed significant binding to IL-1R1 as detected by ELISA were further tested for biological activity using in vitro binding assays and human chondrocyte and whole blood cell-based assays. The antibodies that displayed the best activity were designated 15C4, 26F5, 27F2, 24E12, and 10H7. The antibodies were subjected to a preliminary epitope sorting experiment. ELISA plates were coated with human sIL-1R1 (1+2+3 domain), truncated human sIL-1R1 (1+2 domain), rat sIL-1R1, human sIL-1R type II, and ovalbumin (negative control). Antibody binding was detected with a horseradish peroxidase-conjugated anti-Human Fc antibody (Pierce Chemical Co., Rockford, Ill.). The results are summarized in Table 2. A check mark (i) in Table 2 represents a positive result for binding; "X" represents a negative result. Antibodies 15C4, 26F5, 27F2 and 24E12 bind only the IL-1R1 protein that has all three extracellular domains, indicating that the epitopes for each fall within the third domain. Antibody 10H7 binds both the full-length extracellular domain IL-1R1 and also a truncated protein that has only domains 1 and 2, demonstrating that the epitope for this antibody lies within either domain 1 or 2. None of the antibodies tested has cross-reactivity with human type II receptor or rat IL-1R1.

TABLE 2

| Antibody | OA (Negative Control) | Hu sIL-1R1 (1 + 2 + 3 Domain) | Hu sIL-1R1 (1 + 2 Domain) | Hu sIL-1RII (1 + 2 + 3 Domain) | Rat sIL-1R1 (1 + 2 + 3 Domain) |
|---|---|---|---|---|---|
| 15C4 | X | √ | X | X | X |
| 26F5 | X | √ | X | X | X |
| 27F2 | X | √ | X | X | X |
| 24E12 | X | √ | X | X | X |
| 10H7 | X | √ | √ | X | X |

Example 2

In Vitro Inhibition of IL-1 Receptor Type I Complex Formation by Anti-IL-1R1

Antibodies

The ability of the antibodies to inhibit the extracellular binding events required for IL-1 signaling was assessed with recombinant proteins in vitro in an assay in which IL-1 binding to IL-1R results in formation of a high affinity binding site for IL-1 RAcP. The binding of IL-1RAcP to IL-1-bound IL-1R (referred to as "complex formation") is measured as follows. Recombinant proteins were incubated in binding assays in microtiter plates in the absence (control) or presence of antibodies. $IC_{50}$ values were derived from comparisons of control values to values obtained in the presence of antibody at concentrations between 10 fM and 1 μM. In brief, the assay was conducted as follows. Biotinylated IL-1R1 and streptavidin-coated beads (Dynal, Dynabeads M-28) were dispensed in microtiter plates. Antibody was then added to the appropriate wells in a serial dilution covering a broad range of concentrations. IL-1β or IL-1α was added at a concentration of 1 nM, and IL1RAcP labeled with ruthenium (prepared with NHS-Tag (IGEN) according to IGEN protocols) was added at a final concentration of 5 nM. After incubation for 1 hour at room temperature, the binding reaction was analyzed with either an ORIGEN™ 1.5 or M8 instrument (IGEN International Inc.). IL-1RAcP binding to IL-1 bound IL-1R1 was determined by detecting the electrochemiluninescence signal associated with the IL-1R1 bound beads. The reduction of signal resulting from antibody competition of either IL-1 or IL-1RAcP binding was calculated as percentage of ECL signal for maximum binding (no competition).

The inhibition response curve for each antibody in these binding assays was established and $IC_{50}$s were derived using PRISM™ software. The results for inhibition of IL-1β induced binding events are depicted by the graph in FIG. 12. The $IC_{50}$ values for inhibition of complex formation are shown in Table 3 below. Antibodies 15C4, 26F5, 27F2, and 24E12 strongly inhibit complex formation. These antibodies are all IL-1R1 third domain binders, as described above. Antibody 10H7 belongs to a class of antibodies that binds to a construct of the IL-1R lacking the third domain. 10H7 is a less potent inhibitor of IL-1 driven binding of IL-1RAcP than the third domain binders. Complex formation inhibition by the antibodies of the invention was compared with inhibition by IL-1ra. The third domain binders demonstrated similar or slightly greater ability to inhibit complex formation by comparison with IL-1ra.

Figure 13:
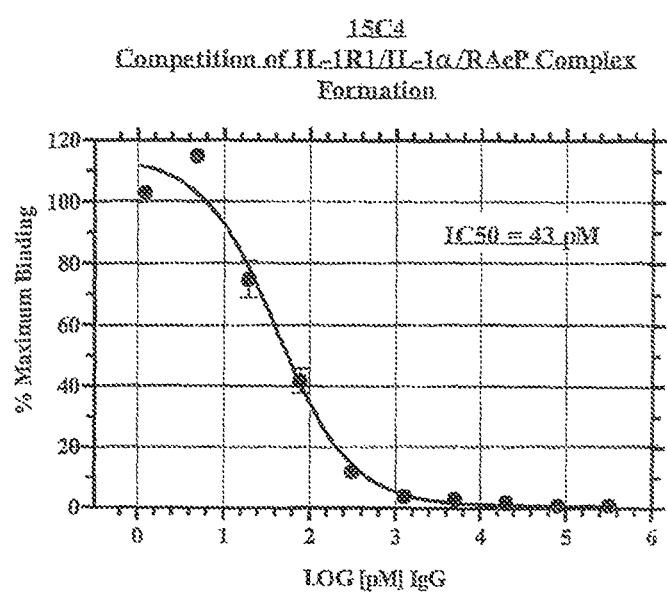
FIG. 13 is a graph showing the inhibitory effect of an anti-IL-1R1 monoclonal antibody as described herein and designated 15C4 on IL-1R/IL-1α/IL-1RacP complex formation.

FIG. 13 depicts the ability of antibody 15C4 to inhibit IL-1R1/IL-1α/RAcP complex formation. The $IC_{50}$ for IL-1R1/IL-1α/RAcP complex formation was 43 pM.

TABLE 3

| | Human anti-IL-1R1 | | | | | |
|---|---|---|---|---|---|---|
| | 15C4 | 26F5 | 27F2 | 24E12 | 10H17 | rII-1ra |
| IC50 | 96 pM | 160 pM | 333 pM | 348 pM | 5.3 nM | 555 pM |
| 95% Confidence Limits | 71 pM to 129 pM | 118 pM to 219 pM | 214 pM to 517 pM | 223 pM to 542 pM | 3.6 nM to 7.5 nM | 414 pM to 743 pM |

Example 3

Anti-IL-1R1 Antibodies Inhibit Binding of IL-1β and IL-1ra to Receptor

Figure 14:
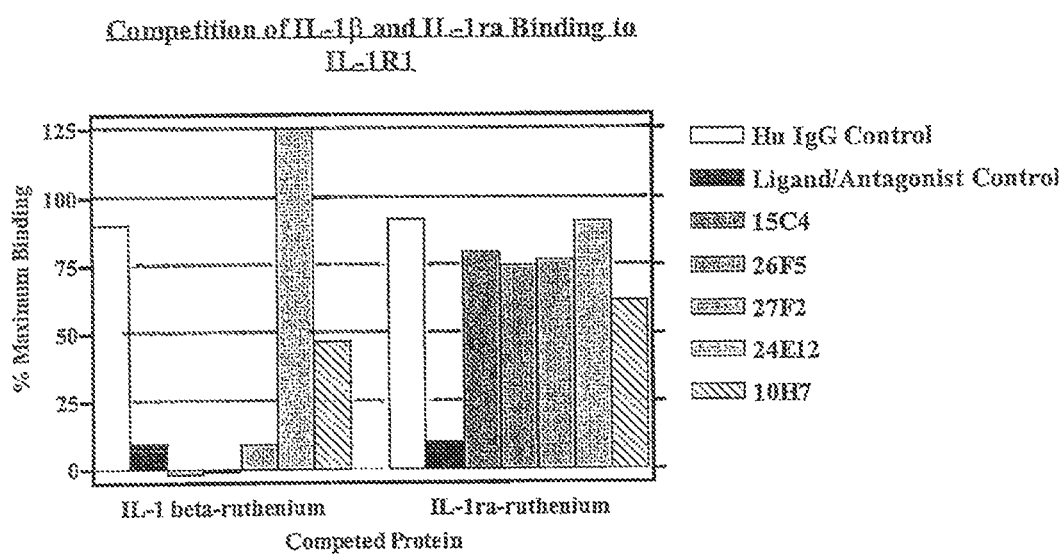
FIG. 14 is a graph representing the ability of anti-IL-1R1 antibodies to block IL-1β binding while not significantly interfering with binding of IL-1ra compared with IgG control.

The ability of anti-IL-1R1 antibodies to inhibit binding of either IL-1β or IL-1ra to IL-1R1 was assessed in an assay with recombinant proteins. The reaction mixture contained 0.1 mg/mL Dynabeads M-280 Streptavidin (Dynal) and 1 nM biotinylated IL-1R1. Antibodies were added at concentrations from 320 nM to 0.3 nM. Addition of ruthenium-tagged IL-1β (5 nM) or IL-1ra (1 nM) initiated binding that proceeded for 1 hour at room temperature. The reaction mixtures were measured as above using an ORIGEN™ 1.5 or M8 instrument (IGEN International Inc.). Competition was calculated as the percentage of ECL signal for maximum binding (no competition). Antibodies 15C4, 26F5, and 27F2, the most potent antibodies, block ligand (IL-1β) binding to receptor, but do not significantly interfere with the binding of IL-1ra compared with IgG control. In contrast, antibody 24E12 binds receptor but does not block IL-1β or IL-1ra binding to receptor. Thus, antibody 24E12 represents a unique class of third domain binders distinct from the class represented by 15C4, 26F5, and 27F2. Antibody 10H7 inhibits both IL-1β and IL-1ra from binding to the receptor. The results are summarized in FIG. 14.

Example 4

Chondrocyte and Human Whole Blood Assays

Figure 15A:
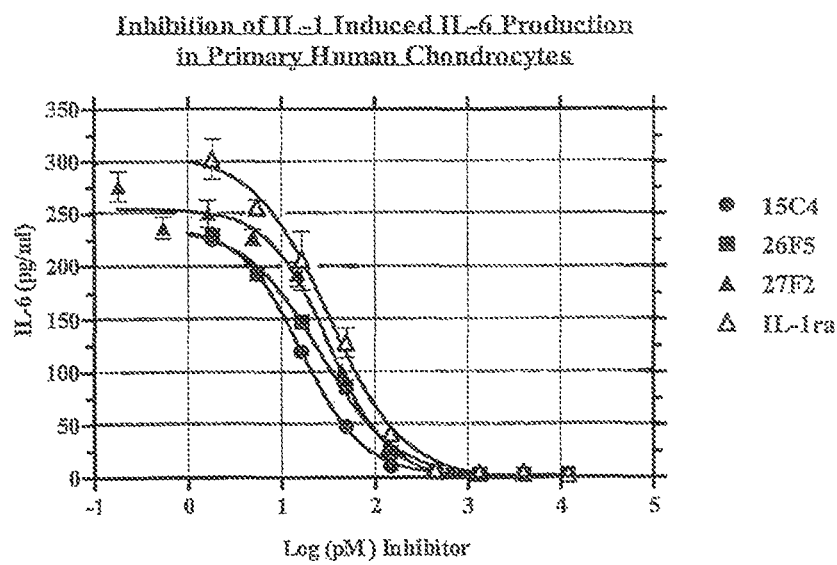
FIG. 15A is a graph showing inhibition of IL-6 production in primary human chondrocytes by anti-IL-1R1 antibodies identified herein and designated 15C4, 26F5, and 27F2 compared with IL-1ra.
Figure 15B:
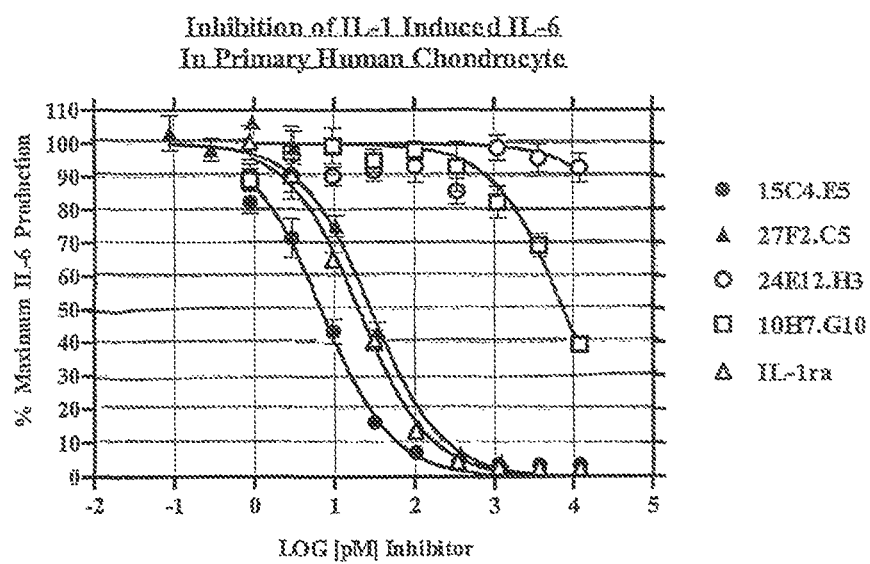
FIG. 15B is a graph showing inhibition of IL-6 production in primary human chondrocytes by IL-1ra and monoclonal antibodies 15C4 and 27F2 compared with the class of monoclonal antibodies represented by 10H7 and 24E12.

Primary human chondrocytes (Cell Applications Inc., San Diego, Calif.) were seeded into 96-well plates at a density of 10,000 cells/well in DMEM media containing 1% FBS and 1% Pen Strep (GIBCO). Cells were allowed to recover overnight before addition of anti-IL1-RI antibodies at concentrations ranging from 10 nM to 0.1 pM for 20 minutes. IL-1β was added to a concentration of 1 pM ($\sim EC_{50}$) and culture supernatants were harvested after 16 hours incubation at 37° C. IL-6 levels in the supernatant were measured using an ELISA (Pierce-Endogen, Rockford, Ill., Cat#EH2IL-65) according to the manufacturer's instructions. The inhibition response curve for each antibody of the invention in the cell-based assays was established and $IC_{50}$ values were derived using PRISM™ software. Antibodies 15C4, 26F5, and 27F2 are potent inhibitors of IL-1 signaling compared with IL-1ra (FIG. 15A). Antibodies 24E12 and 10H7 are markedly less potent than 15C4 and 27F2 (FIG. 15B). The $IC_{50}$ values for inhibition of IL-13 induced IL-6 production human chondrocytes are shown in Tables 4A and 4B (corresponding to FIGS. 15A and 15B respectively).

Figure 16:
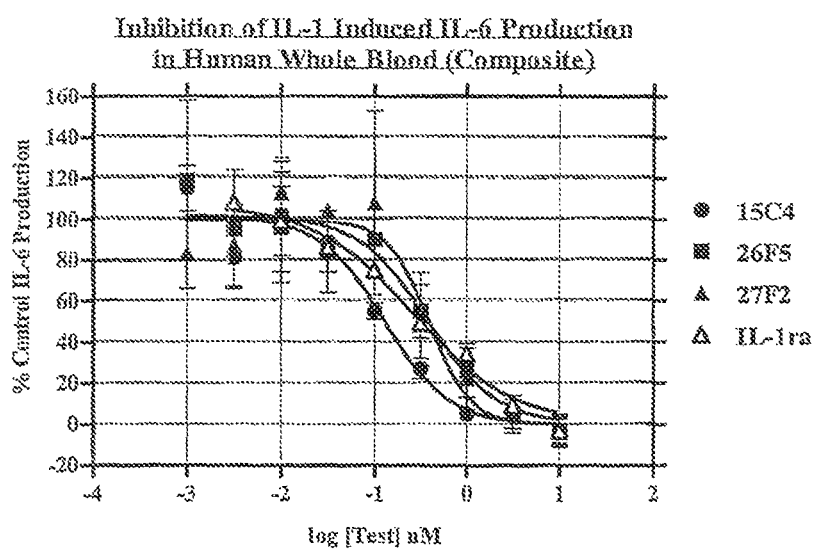
FIG. 16 is a graph showing inhibition of IL-6 production in human whole blood by anti-IL-1R1 monoclonal antibodies designated 15C4, 26F5, and 27F2 compared with IL-1ra.

Anti-IL-1R1 monoclonal antibodies 15C4, 26F5, and 27F2 were pre-incubated 40-60 minutes with human whole blood collected from normal volunteers in sodium heparin vacutainers. The assays were run as follows: 100 µL freshly isolated blood was aliquoted wells of a 96-well plate. 50 µL of antibody was added in RPMI medium containing 10% human AB serum. IL-1β was then added at a concentration of 30 pM ($EC_{50}$). Culture supernatants were harvested after 18 hours, and IL-6 levels in the supernatant were measured using an ELISA. As a control, IL-1ra was pre-incubated 40-60 minutes with whole blood and IL-6 production was measured as above. The three anti-IL-1R1 antibodies blocked IL-1 activity with potency comparable to that of IL-1ra (FIG. 16). The IC50 values for inhibition of IL-1-induced IL-6 production in human whole blood are shown in Table 5.

TABLE 4A

| | Human anti-IL-1R1 Antibodies | | | |
|---|---|---|---|---|
| | 15C4 | 27F2 | 26F5 | rIL-1ra |
| 1050 | 16 pM | 32 pM | 26 pM | 32 pM |
| 95% Confidence Limits | 15 pM to 18 pM | 21 pM to 49 pM | 9 pM to 36 pM | 22 pM to 46 pM |

TABLE 4B

| | Human anti-IL-1R1 Antibodies | | | | |
|---|---|---|---|---|---|
| | 15C4 | 27F2 | 10H7 | 24E12 | rIL-1ra |
| IC50 | 7 pM | 28 pM | 7.5 pM | NA | 20 pM |
| 95% Confidence Limits | 5.8 pM to 7.9 pM | 22 pM to 35 pM | 5.6 nM to 10 nM | NA | 17 pM to 23 pM |

TABLE 5

| Donor | Analysis Parameters | 15C4 | 26F5 | 27F2 | IL-1ra |
|---|---|---|---|---|---|
| 1047 | IC50 | 126 pM | 410 pM | 249 pM | 241 pM |
| | 95% Confidence Limits | 47 pM to 339 pM | 213 pM to 790 pM | 88 pM to 703 pM | 124 pM to 471 pM |
| 1319 | IC50 | 111 pM | 174 pM | 579 pM | 381 pM |
| | 95% Confidence Limits | 59 pM to 208 pM | 60 pM to 501 pM | 249 pM to 1.3 nM | 167 pM to 875 pM |
| Composite (Pooled Data) | IC50 | 126 pM | 372 pM | 387 pM | 264 pM |
| | 95% Confidence Limits | 62 pM to 255 pM | 187 pM to 739 pM | 202 pM to 748 pM | 134 pM to 517 pM |

Example 5

Mutagenesis and Epitope Mapping

Figure 18:
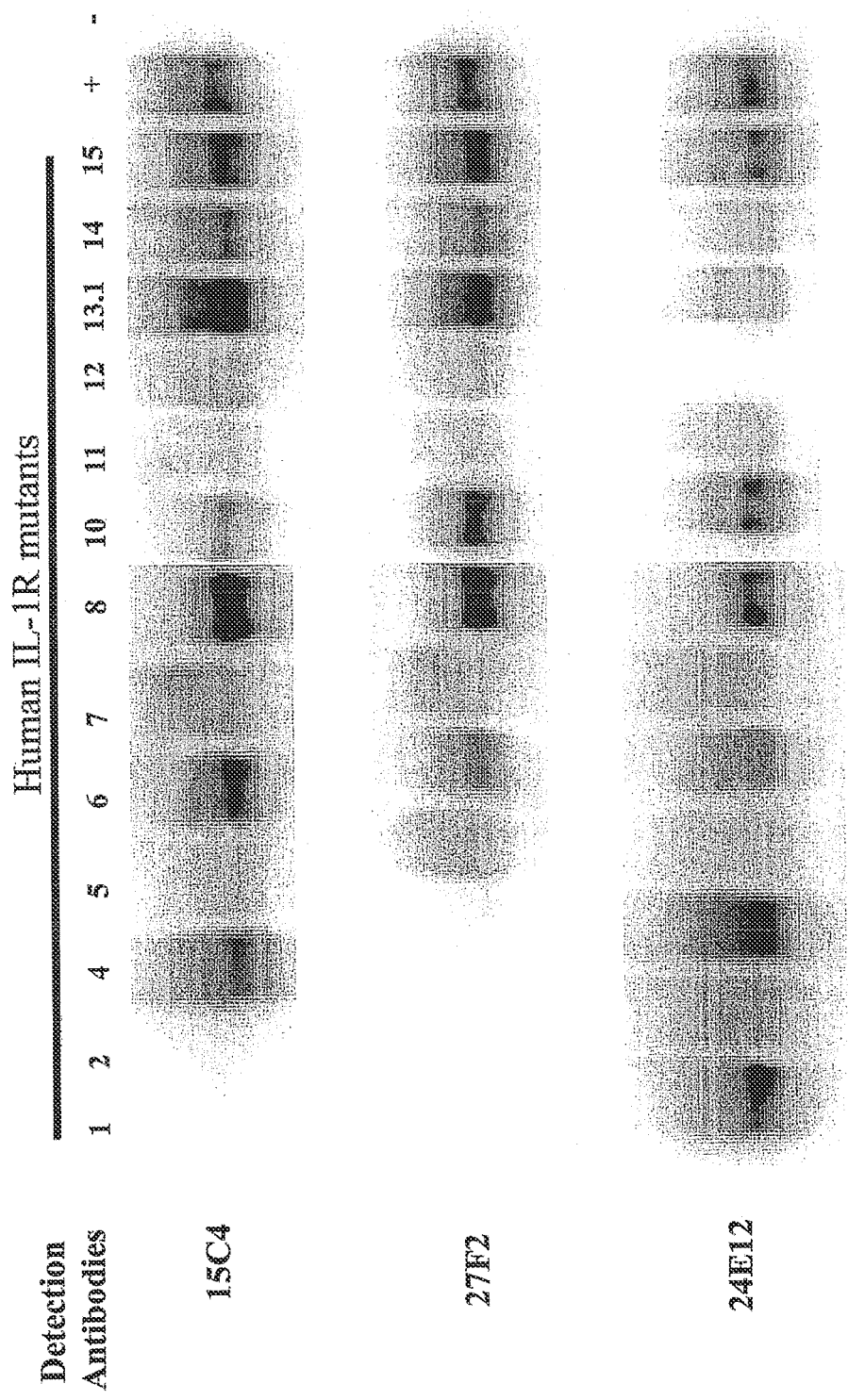
FIG. 18 shows Western blot analysis demonstrating anti-IL-1R1 monoclonal antibody recognition of IL-1R1 mutants.

Site directed mutagenesis (Altered Sites® In Vitro Mutagenesis System, Promega, Madison Wis.) of IL-1R1 was used to prepare a panel of mutant proteins ("muteins") in which rat amino acid residues were substituted for the corresponding human sequence. Fifteen different mutated plasmids were constructed (see numbered bars in FIG. 17). Plasmids encoding these substituted proteins and the parental IL-1R1 were transiently transfected in CHO cells. Mock transfectants were generated as negative controls. Conditioned medium (CM) from these cells was concentrated-20-fold using Centriprep 10 concentration columns (Amicon). Expression of the muteins was assessed by SDS-PAGE and Western blotting. Thirteen mutant proteins were expressed at levels that allowed evaluation of antibody binding. The proteins were loaded onto a gel, electrophoresed and transferred to membranes. The membranes were blocked in 1% milk in PBS, 0.1% Tween-20 and then incubated for 1 hour at room temperature with anti-IL-1R antibodies 15C4, 27F2, or 24E12 at 0.5 ug/mL in PBS, 0.1% Tween-20. After washing, membranes were incubated with goat anti-human IgG-Fc-HRP. Signal was detected using chemiluminescence (ECL) substrate (Pierce Chemical Co., Rockford, Ill.). Human specific sequences critical for antibody binding were identified as those that when substituted with rat sequences reduced or eliminated ECL signal. 15C4 recognition of mutants 1, 2, 4 and 10 was impaired when compared to 24E12 (FIG. 18, top panel). Similarly, 27F2 binding to mutants 1, 2 and 4 was impaired (FIG. 18, middle panel). 24E12 had no significant binding to mutants 12, 13, 14 and 15 (FIG. 18, bottom panel).

Figure 19:
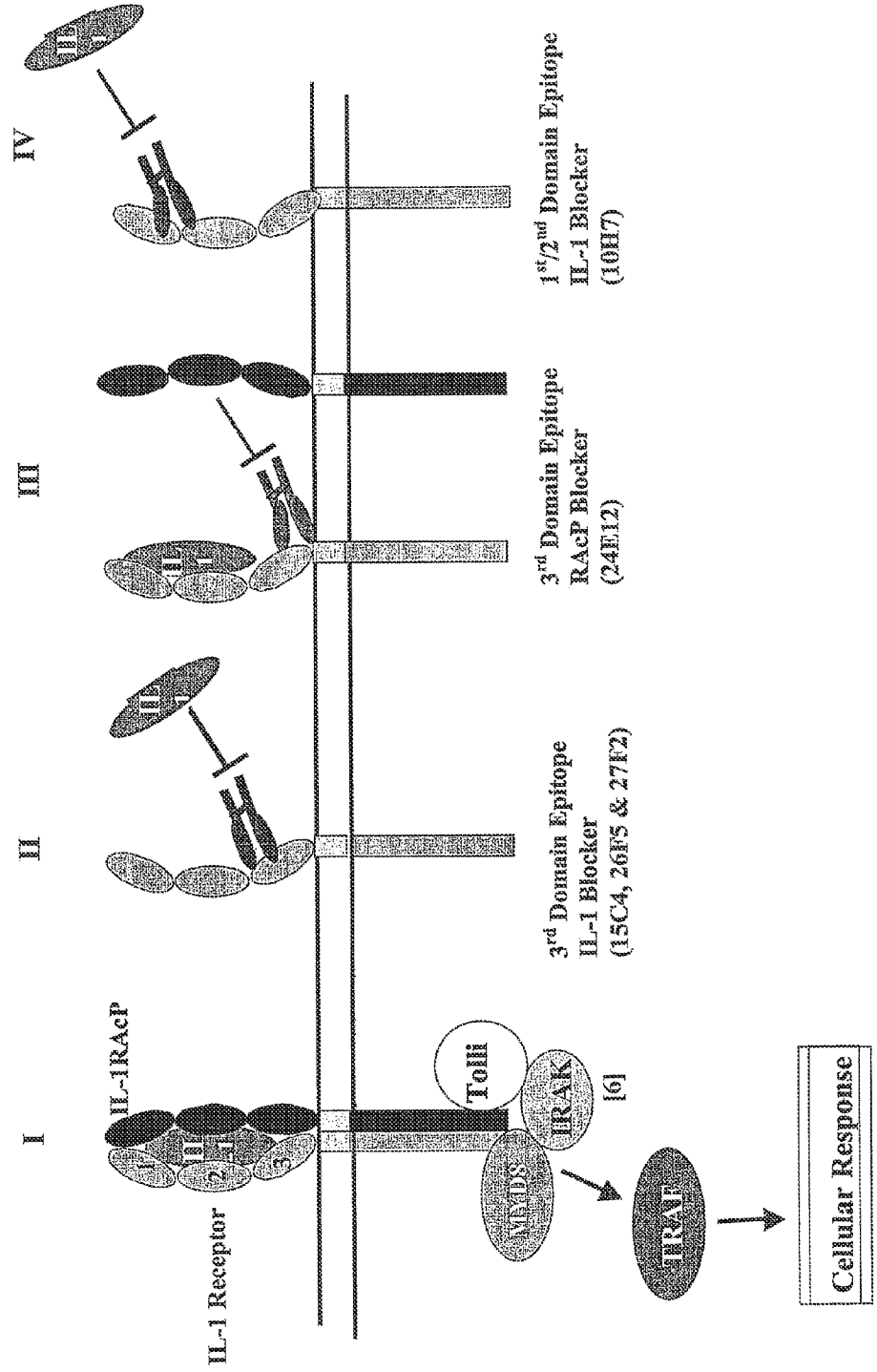
FIG. 19 is a drawing representing (I) activation of the IL-1 signaling pathway, which starts with binding of IL-1β to IL-1R1, and recruitment of IL-1RacP, and three classes of anti-IL-1R1 antibodies: (II) $3^{rd}$ domain epitope IL-1 blockers, (II) $3^{rd}$ domain epitope RAcP blockers, and (IV) $1^{st}/2^{nd}$ domain epitope IL-1 blockers.
Figure 20:
FIG. 20 depicts the crystal structure of 15C4 and 27F2 with mutation 10 as described herein. The gray residues indicate the 15C4 and 27F2 epitopes.
Figure 21:
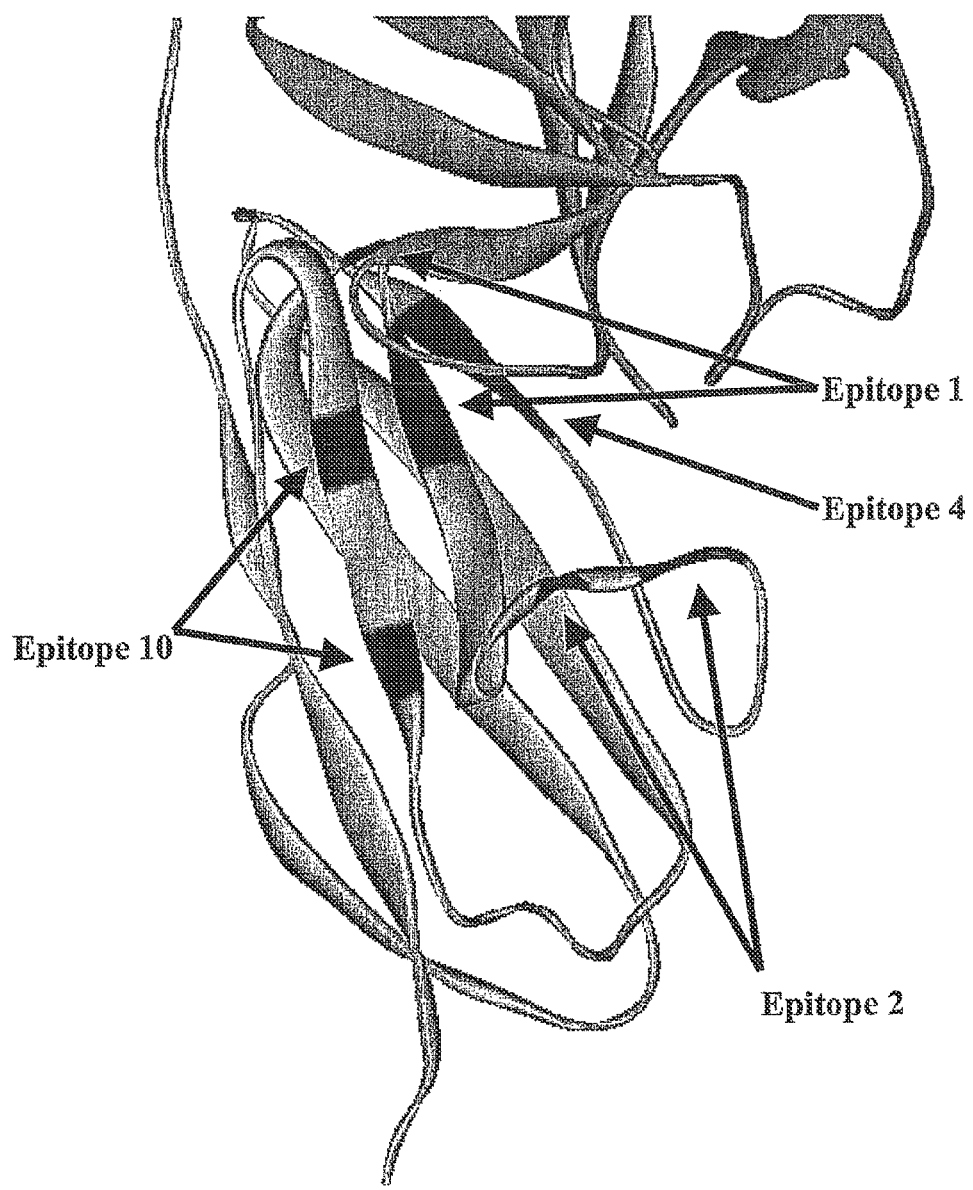
FIG. 21 depicts the 15C4 epitopes in the third domain of extracellular IL-1R1.

Isolation and characterization of human anti-IL-1R1 antibodies has identified three distinct classes of competitive antibodies (FIG. 19). The strongest inhibitors of IL-1 biological activity, as demonstrated by cell-based bioassays, are those antibodies that bind the third domain of IL-1R1 and prevent IL-1-β association. Epitope mapping experiments using a panel of third domain mutant proteins has demonstrated that this class of antibodies, which includes 15C4, 27F2 and 26F5, shares an overlapping but not identical, conformational epitope. FIGS. 20 and 21 illustrate the position of 15C4 epitopes on the third domain of the IL-1 receptor, in a ribbon diagram of IL-1ra bound IL-1 receptor (Schreuder et al., 1997, *Nature* 386:194-200). The IL-1 receptor residues that define binding of the most potent class of antibodies are illustrated in gray. These antibodies have demonstrated superior potency, and thus these epitopes define binding sites for antibodies of a superior class. The 15C4 and 27F2 binding sites are overlapping but not identical, as determined by the mutational analysis of the 15 different sites within IL-1R1 described above. The sites are depicted in FIG. 17 as numbered bars above the protein sequence. Critical sites of interaction appear to be within mutations at sites 1 (LSDIA; SEQ ID NO: 41), 2 (VIDE; SEQ ID NO: 42), 4 (YSV) and 10 (TCFA; SEQ ID NO: 43). 15C4 and 27F2 binding sites are comprised within sites 1 and 2, since substitution of the rat residues for the human residues in either site abolishes binding. 27F2 differs from 15C4 in that changes in site 4 completely abolish its binding, whereas 15C4 binding is reduced but not completely eliminated. Mutation 10 also reduces 15C4 binding, but 27F2 has no obvious interaction with this site. Examination of the crystal structure reveals that these residues define a face of the third domain that is oriented towards the space occupied by bound ligand (FIGS. 20 and 21) (Vigers et al., 1997, *Nature* 386:190-194).

The second class of antibodies identified, represented by 10H7, does not require the third domain for binding, and unlike the preferred class, inhibits IL-1ra binding. This class is active in bioassays, but is less potent than the preferred class.

Figure 22:
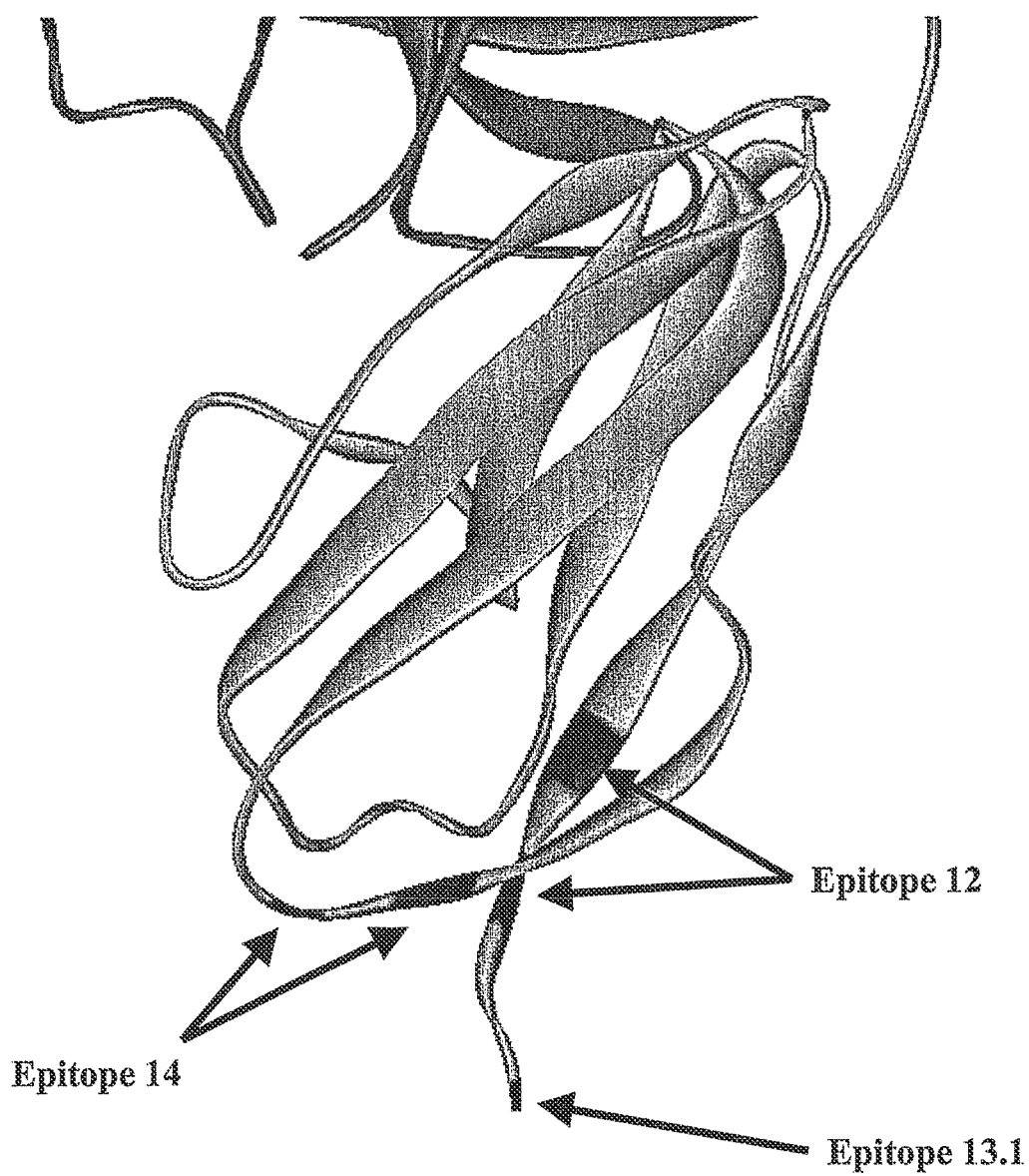
FIG. 22 depicts 24E12 epitopes in the third domain of extracellular IL-1R1.
Figure 26:
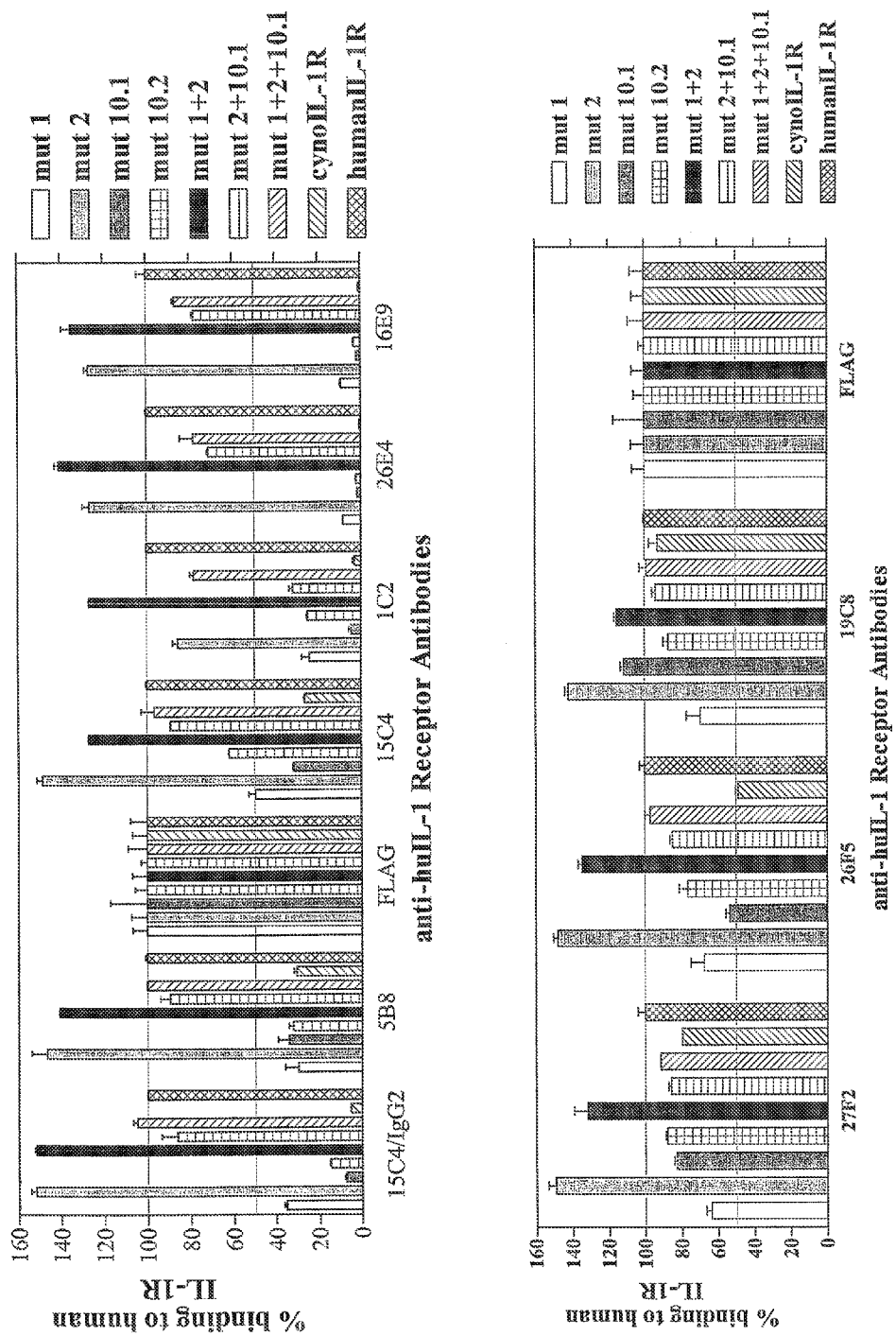
FIG. 26 shows graphs representing the binding of anti-huIL1R1 antibodies to avidin IL-1R1-FLAG proteins in a multiplexed bead-based binding assay.

In contrast to the strong inhibition of IL-1 bioassays with the preferred class of antibodies, 24E12 is an ineffective inhibitor in bioassays. Antibody 24E12 inhibits the binding of IL-1RAcP with IL-1-bound IL-1R. The epitope for this class of antibodies, defined by mutants 12, 13, 14 and 15, is proximal to the transmembrane domain of IL-1R1, and is in a region not directly involved in either IL-1 or IL-1ra binding (FIG. 22).

Example 6

Cloning the Anti-IL-1R1 Antibody Heavy and Light Chains

Cloning of the Anti-IL-1R115C4 MAb Light Chain

The light chains for three hybridomas expressing αIL-1R1 binding monoclonal antibodies, 15C4, 27F2, and 26F5 were cloned into the mammalian cell expression vector pDSRα19 (see International Application, Publication No. WO 90/14363, which is herein incorporated by reference for any purpose). The construction of the plasmid encoding the 15C4 kappa light chain is explicitly described herein; cloning of the other light chain species was performed using similar procedures. The αIL-1R1 kappa light chain variable region was obtained using polymerase chain reaction (PCR) amplification methods from first strand cDNA prepared from αIL-1R1 hybridoma 15C4 total RNA prepared using TRIzol® reagent (Invitrogen). First strand cDNA was synthesized using a random primer with an extension adapter (5'-GGC CGG ATA GGC CTC CAN NNN NNT-3'; SEQ ID NO: 44) and 5' RACE (rapid amplification of cDNA ends) was performed using the GeneRacer™ Kit (Invitrogen). For the complete light chain, the forward primer was the GeneRacer™ nested primer (5' GGA CAC TGA CAT GGA CTG AAG GAG TA-3'; SEQ ID NO: 45) and the reverse primer was 5'-GGG GTC AGG CTG GAA CTG AGG-3' (SEQ ID NO: 46). The RACE products were cloned into pCR4-TOPO (Invitrogen) and the DNA sequences were determined. The 15C4 kappa chain consensus DNA sequence was used to design primers for full-length antibody chain PCR amplification. The 5' kappa PCR primer encoded the amino terminus of the signal sequence, an XbaI restriction enzyme site, and an optimized Kozak sequence (5'-CAG CAG AAG CTT CTA GAC CAC CAT GTC GCC ATC ACA ACT CAT TGG G-3'; SEQ ID NO: 47). The 3' primer encoded the carboxyl terminus and termination codon, as well as a SalI restriction site (5'-CTT GTC GAC TCA ACA CTC TCC CCT GTT GAA GCT C-3'; SEQ ID NO: 48).

```
5' αIL-1R1 15C4 kappa primer:
5'-CAG CAG AAG CTT CTA GAC CAC CAT              (SEQ ID NO: 47)
             XbaI    Kozak  M                    (SEQ ID NO: 49)
   GTC GCC ATC ACA ACT CAT TGG G-3'
    S   P   S   Q   L   I   G 3' αIL-1R1 15C4 kappa primer:
5'-CTT GTC GAC TCA ACA CTC TCC CCT GTT GAA GCT C-3'  (SEQ ID NO: 48)
       SalI    *   C   E   G   R   N   F   S         (SEQ ID NO: 50)
```

The full-length αIL-1R115C4 kappa chain clone was obtained using a pCR4: 15C4 kappa clone by PCR amplification with the 5' and 3' αIL-1R115C4 kappa primers. The PCR reaction generated a 733 base pair product encoding the 233 amino acids residues (including the 19 amino acid kappa chain signal sequence) of the αIL-1R115C4 kappa chain. The PCR product was purified using a QIAquick PCR Purification kit (Qiagen Cat. No. 28104), cut with XbaI and SalI, gel isolated and purified using a QIAquick Gel Extraction kit (Qiagen Cat. No. 28704). This PCR fragment containing the complete αIL-1R115C4 kappa chain was then ligated into the mammalian expression vector pDSRα19. The 15C4 kappa chain expression clone was DNA sequenced to confirm that it encoded the same peptide that was identified in the 15C4 hybridoma. The final expression vector, pDSRα19:15C4 kappa is 5468 base pairs and contains the seven functional regions described in Table 6.

TABLE 6

Plasmid Base Pair Number:

| | |
|---|---|
| 2 to 881 | A transcription termination/polyadenylation signal from the α-subunit of the bovine pituitary glycoprotein hormone (α-FSH) (Goodwin et al., 1983, Nucleic Acids Res. 11:6873-82; Genbank Accession Number X00004) |
| 882 to 2027 | A mouse dihydrofolate reductase (DHFR) minigene containing the endogenous mouse DHFR promoter, the cDNA coding sequences, and the DEIFR transcription termination/polyadenylation signals (Gasser et al, 1982, Proc. Natl. Acad. Sci. U.S.A. 79:6522-6; Nunberg et al., 1980, Cell 19:355-64; Setzer et al., 1982, J. Biol. Chem, 257:5143-7; McGrogan et al., 1985, J Biol. (Chem. 260:2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, Mol. Cell Biol. 8:466-72, Genbank Accession Number J02400) |
| 4299 to 4565 | A translational enhancer element from the HTLV-1 LTR domain (Seiki et al., 1983, Proc. Natl, Acad. Sci. U.S.A. 80:3618-22, Genbank Accession Number J02029) |
| 4574 to 4730 | An intron from the SV40 16S, 19S splice donor/acceptor signals (Okayama and Berg, 1983, Mol. Cell Biol. 3:280-9, Genbank Accession Number J02400) |
| 4755 to 5468 | The 15C4 kappa light chain cDNA between the XbaI and SalI sites |

Construction of pDSR19:hIgG1$C_H$

A pDSRα19:rat variable region/human constant region IgG1 (rVh/hCh1) MAb expression plasmid was constructed as the result of a three-piece ligation of XbaI and BsrBI terminated rat antibody variable region PCR product, the human IgG1 constant region ($C_{H1}$, hinge, $C_{H2}$ and $C_{H3}$ domains) derived by SaiI cleavage and gel isolation of the BsmBI and SalI fragment from the linear plasmid pDSRα 19:hIgG1 $C_H$ (HindIII and BsmBI ends) and a linearized pDSRα19 with XbaI and SalI ends (see co-owned and co-pending U.S. Provisional Patent Application No. 60/370,407, filed Apr. 5, 2002, "Human Anti-OPGL Neutralizing Antibodies As Selective OPGL Pathway Inhibitors," incorporated by reference). The final expression vector, pDSRα19:rat variable region/human constant region IgG1 (rVh/hCh1), is 6158 base pairs and contains the 7 functional regions described in Table 7.

TABLE 7

| | |
|---|---|
| 2 to 881 | A transcription termination/polyadenylation signal from the α-subunit of the bovine pituitary glycoprotein hormone (α-FSH) (Goodwin et al., 1983, *Nucleic Acids Res.* 11:6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al., 1982, *Proc. Natl. Acad. Sci.* U.S.A. 79:6522-6; Nunberg et al., 1980, *Cell* 19:355-64; Setzer et al., 1982, *J. Biol. Chem.* 257:5143-7; McGrogan et al., 1985, *J. Biol. Chem.* 260:2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, *Mol. Cell Biol.* 8:466-72, Genbank Accession Number J02400) |
| 4299 to 4565 | A translational enhancer element from the HTLV-1 LTR domain (Seiki et al., 1983, *Proc. Natl. Acad. Sci.* U.S.A. 80:3618-22, Genbank Accession Number J02029) |

TABLE 7-continued

| | |
|---|---|
| 4574 to 4730 | An intron from the SV40 16S, 19S splice donor/acceptor signals (Okayama and Berg, 1983. *Mol. Cell Biol.* 3:280-9, Genbank Accession Number J02400) |
| 4755 to 6158 | The rVh/hCh1 heavy chain cDNA between the *Xba*I and *Sal*I sites. This heavy chain fragment sequence is shown below (SEQ ID NO: 51) with the sequences of the restriction sites underlined: |

```
XbaI
TCTAG ACCACCATGG ACATCAGGCT CAGCTTAGTT TTCCTTGTCC

TTTTCATAAA AGGTGTCCAG TGTGAGGTAG AACTGGTGGA

GTCTGGGGGC GGCTTAGTAC AACCTGGAAG GTCCATGACA

CTCTCCTGTG CAGCCTCGGG ATTCACTTTC AGAACCTATG GCATGGCCTG

GGTCCGCCAG GCCCCAACGA AGGGTCTGGA GTGGGTCTCA

TCAATTACTG CTAGTGGTGG TACCACCTAC TATCGAGACT CCGTGAAGGG

CCGCTTCACT ATTTTTAGGG ATAATGCAAA AAGTACCCTA TACCTGCAGA

TGGACAGTCC GAGGTCTGAG GACACGGCCA CTTATTTCTG TACATCAATT

BsmB1
TCGGAATACT GGGGCCACGG AGTCATGGTC ACCGTCTCTA

GTGCCTCCAC CAAGGGCCCA TCGGTCTTCC CCCTGGCACC CTCCTCCAAG

AGCACCTCTG GGGGCACAGC GGCCCTGGGC TGCCTGGTCA AGGACTACTT

CCCCGAACCG GTGACGGTGT CGTGGAACTC AGGCGCCCTG

ACCAGCGGCG TGCACACCTT CCCGGCTGTC CTACAGTCCT CAGGACTCTA

CTCCCTCAGC AGCGTGGTGA CCGTGCCCTC CAGCAGCTTG GGCACCCAGA

CCTACATCTG CAACGTGAAT CACAAGCCCA GCAACACCAA

GGTGGACAAG AAAGTTGAGC CCAAATCTTG TGACAAAACT

CACACATGCC CACCGTGCCC AGCACCTGAA CTCCTGGGGG

GACCGTCAGT CTTCCTCTTC CCCCCAAAAC CCAAGGACAC CCTCATGATC

TCCCGGACCC CTGAGGTCAC ATGCGTGGTG GTGGACGTGA

GCCACGAAGACCCTGAGGTC AAGTTCAACT GGTACGTGGA

CGGCGTGGAG GTGCATAATG CCAAGACAAA GCCGCGGGAG

GAGCAGTACA ACAGCACGTA CCGTGTGGTC AGCGTCCTCA

CCGTCCTGCA CCAGGACTGG CTGAATGGCA

AGGAGTACAAGTGCAAGGTC TCCAACAAAG CCCTCCCAGC

CCCCATCGAG AAAACCATCT CCAAAGCCAA AGGGCAGCCC

CGAGAACCAC AGGTGTACAC CCTGCCCCCA TCCCGGGATG

AGCTGACCAA GAACCAGGTC AGCCTGACCT GCCTGGTCAA

AGGCTTCTAT CCCAGCGACA TCGCCGTGGA GTGGGAGAGC

AATGGGCAGCCGGAGAACAA CTACAAGACC ACGCCTCCCG
```

TABLE 7-continued

```
TGCTGGACTC CGACGGCTCC TTCTTCCTCT ATAGCAAGCT CACCGTGGAC

AAGAGCAGGT GGCAGCAGGG GAACGTCTTC TCATGCTCCG

TGATGCATGA GGCTCTGCAC AACCACTACA CGCAGAAGAG

CCTCTCCCTG TCTCCGGGTA

SalI
AATGATAAGT CGAC
```

The linear plasmid pDSRα19:hIgG1C$_H$ was prepared by digesting the pDSR19:rat variable region/human constant region IgG1 plasmid with the restriction enzymes XbaI and BsmBI to remove the rat variable region and purified using a QIAquick Gel Extraction kit. The linear plasmid pDSRα19:hIgG1C$_H$ containing the 1 kbp human IgG constant region domain was used to accept hybridoma derived αIL-1R antibody variable regions.

Cloning of the Anti-IL1-RI 15C4 MAb Heavy Chain

The heavy chains for ten hybridomas expressing αIL1-RI binding monoclonal antibodies, 15C4, 27F2, and 26F5 were cloned into the mammalian cell expression vector pDSRα19. The construction of the plasmid encoding the 15C4 heavy chain is explicitly described; cloning of the other heavy chain species was performed using similar procedures. The αIL-1R115C4 heavy chain variable region was obtained using PCR amplification methods from first strand cDNA prepared from αIL1-RI hybridoma 15C4 total RNA prepared using TRIzol® reagent. First strand cDNA was synthesized using a random primer with an extension adapter (5'-GGC CGG ATA GGC CTC CAN NNN NNT-3'; SEQ ID NO: 44) and a 5' RACE (rapid amplification of cDNA ends) was performed using the GeneRacer™ Kit. For the partial length heavy chain, the forward primer was the GeneRacer™ nested primer (5' GGA CAC TGA CAT GGA CTG AAG AGT A-3'; SEQ ID NO: 45) and the reverse primer was 5'-TGA GGA CGC TGA CCA CAC G-3' (SEQ ID NO 52.). The RACE products were cloned into pCR4-TOPO and the DNA sequences were determined. The 15C4 heavy chain variable region consensus DNA sequence was used to design primers for the heavy chain variable region PCR amplification. The 5' heavy chain PCR primer encoded the amino terminus of the signal sequence, an XbaI restriction enzyme site, and an optimized Kozak sequence (5'-CAG CAG AAG (CTT CTA GAC CAC CAT GGG GTC AAC CGC CAT CCT CG-3'; SEQ ID NO: 53). The 3' primer encoded the carboxyl end of the variable region, including a naturally occurring sense strand BsmBI site (5'-GTG GAG GCA CTA GAG ACG GTG ACC AGG GTT CC-3'; SEQ ID NO: 54).

```
5'αIL-1R1 15C4 heavy chain primer:
5'-CAG CAG AAG CTT CTA GAC CAC C ATG            (SEQ ID NO: 53)
                  XbaI   Kozak  M               (SEQ ID NO: 55)
GGG TCA ACC GCC ATC CTCG-3'
 G   S   T   A   I   L 3'αIL-1R1 15C4 heavy chain primer:
5'-GTG GAG GCA CTA GAG ACG                      (SEQ ID NO: 54)
     T   S   A   S   S   V                      (SEQ ID NO: 56)
GTG ACC AGG GTT CC-3'
 T   V   L   T   G
           BsmBI
```

Construction of the Anti-IL1-RI IgG1 Heavy Chain Expression Clone

The full-length αIL-1R1 15C4 heavy chain clone was obtained from a pCR4:15C4 heavy chain clone by PCR amplification with the 5' and 3' αIL-1R1 15C4 heavy chain primers. The PCR reaction generated a 442 base pair product encoding the 137 amino acids residues (including the 19 amino acid heavy chain signal sequence) of the αIL-1R1 15C4 heavy chain variable region. The PCR product was purified using a QIAquick PCR Purification kit and then digested with XbaI and BsmBI, gel isolated and purified using a QIAquick Gel Extraction kit. This fragment containing the complete αIL-1R1 15C4 heavy chain variable region was then ligated into the mammalian expression vector pDSRα19:hIgG1C$_H$. The 15C4 heavy chain IgG1 expression clone was DNA sequenced to confirm that it encoded the same heavy chain variable region peptide that was identified in the 15C4 hybridoma. The final expression vector, pDSRα19:15C4 IgG1 heavy chain was 6173 base pairs and contains the seven functional regions described in Table 8.

TABLE 8

| Plasmid Base Pair Number: | |
|---|---|
| 2 to 881 | A transcription termination/polyadenylation signal from the α-subunit of the bovine pituitary glycoprotein hormone (α-FSH) (Goodwin et al., 1983, Nucleic Acids Res, 11:6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al., 1982, Proc. Natl. Acad. Sci. U.S.A. 79:6522-6; Nunberg et al., 1980, Cell 19:355-64; Setzer et al., 1982, J. Biol. Chem. 257:5143-7; McGrogan et al., 1985, J Biol. Chem. 260:2307-14) |
| 2031 to 3947 | pBR322 sequences containing the ampicillin resistance marker gene and the origin for replication of the plasmid in E. coli (Genbank Accession Number J01749) |
| 3949 to 4292 | An SV40 early promoter, enhancer and origin of replication (Takebe et al., 1988, Mol. Cell Biol. 8:466-72, Genbank Accession Number J02400) |
| 4299 to 4565 | A translational enhancer element from the HTLV-1 LTR domain (Seiki et al., 1983, Proc. Natl, Acad. Sci. U.S.A. 80:3618-22, Genbank Accession Number J02029) |
| 4574 to 4730 | An intron from the SV40 16S, 19S splice donor/acceptor signals (Okayama and Berg, 1983. Mol. Cell Biol. 3:280-9, Genbank Accession Number J02400) |
| 4755 to 6173 | The 15C4 heavy chain IgG1 cDNA between the XbaI and SalI sites |

Construction of pDSR19:hIgG2C$_H$

A pDSRα19:human variable region/human constant region IgG2 (hVh/hCh2) MAb expression plasmid was constructed as the result of a three-piece ligation of XbaI and BsmBI terminated human antibody variable region PCR product, a human IgG2 constant region (C$_{H1}$, hinge, C$_{H2}$ and C$_{H3}$ domains) PCR product with BsmBI and SalI ends and a linearized pDSRa19 with XbaI and SaiI ends. The final expression vector, pDSRα19:human variable region/human constant region IgG1 (hVh/hCh2) (see co-owned and co-pending U.S. Provisional Patent Application No. 60/370,407, filed Apr. 5, 2002, "Human Anti-OPGL Neutralizing Antibodies As Selective OPGL Pathway Inhibitors"), is 6164 base pairs and contains the 7 functional regions described in Table 9.

TABLE 9

```
Plasmid Base
Pair Number:

2 to  881 A transcription termination/polyadenylation signal
              from the α-subunit of the bovine pituitary
              glycoprotein hormone (α-FSH) (Goodwin et al., 1983,
              Nucleic Acids Res. 11:6873-82; Genbank Accession
              Number X00004)
  882 to 2027 A mouse dihydrofolate reductase (DHFR) minigene
              containing the endogenous mouse DHFR promoter, the
              cDNA coding sequences, and the DHFR transcription
              termination/polyadenylation signals (Gasser et al.,
              1982, Proc. Natl. Acad. Sci. U.S.A. 79:6522-6; Nunberg
              et al., 1980, Cell 19:355-64; Setzer et al., 1982, J.
              Biol. Chem. 257:5143-7; McGrogan et al., 1985, J.
              Biol. Chem. 260:2307-14)
 2031 to 3947 pBR322 sequences containing the ampicillin resistance
              marker gene and the origin for replication of the
              plasmid in E. coli (Genbank Accession Number J01749)
 3949 to 4292 An SV40 early promoter, enhancer and origin of
              replication (Takebe et al., 1988, Mol. Cell Biol.
              8:466-72, Genbank Accession Number J02400)
 4299 to 4565 A translational enhancer element from the HTLV-1 LTR
              domain (Seiki et al., 1983, Proc. Natl. Acad. Sci.
              U.S.A. 80:3618-22, Genbank Accession Number J02029)
 4574 to 4730 An intron from the SV40 16S, 19S splice donor/acceptor
              signals (Okayama and Berg, 1983. Mol. Cell Biol.
              3:280-9, Genbank Accession Number J02400)
 4755 to 6164 The hVh/hCh2 heavy chain cDNA between the XbaI and
              SalI sites. The sequence of this heavy chain fragment
              appears below (SEQ ID NO: 57) with the restriction
              sites underlined:
              XbaI
              TCTAGA CCACCATGGA CATGAGGGTC CCCGCTCAGC TCCTGGGGCT

CCTGCTATTG TGGTTGAGAG GTGCCAGATG TGAGGTCCAG

CTGGTGCAGTCTGGGGGAGG CTTGGTACAT CCTGGGGGGT CCCTGAGACT
```

TABLE 9-continued

Plasmid Base
Pair Number:

```
            CTCCTGTGCAGGCTCTGGAT TCACCTTCAG TGGCCATGCT TTGCACTGGG

TTCGCCAGGCTCCAGGAAAA GGTCTGGAGT GGGTATCAGG TATTGGTACT

CATGGTGGGACATACTATGC AGACTCCGTG AAGGGCCGAT TCACCATCTC

CAGAGACAATGCCAAGAACT CCTTGTTTCT TCAAATGAAC AGCCTGAGCG

CCGAGGACATGGCTGTGTAT TACTGTACAA GAAGAAACTG

BsmB1
            GGGACAATTT GACTACTGGGGCCAGGGAAC CCTGGTCACC GTCTCTAGTG

CCTCCACCAA GGGCCCATCGGTCTTCCCCC TGGCGCCCTG CTCCAGGAGC

ACCTCCGAGA GCACAGCGGCCCTGGGCTGC CTGGTCAAGG ACTACTTCCC

CGAACCGGTG ACGGTGTCGTGGAACTCAGG CGCTCTGACC

AGCGGCGTGC ACACCTTCCC AGCTGTCCTACAGTCCTCAG GACTCTACTC

CCTCAGCAGC GTGGTGACCG TGCCCTCCAGCAACTTCGGC ACCCAGACCT

ACACCTGCAA CGTAGATCAC AAGCCCAGCAACACCAAGGT

GGACAAGACA GTTGAGCGCA AATGTTGTGT

CGAGTGCCCACCGTGCCCAG CACCACCTGT GGCAGGACCG TCAGTCTTCC

TCTTCCCCCCAAAACCCAAG GACACCCTCA TGATCTCCCG GACCCCTGAG

GTCACGTGCGTGGTGGTGGA CGTGAGCCAC GAAGACCCCG

AGGTCCAGTT CAACTGGTACGTGGACGGCG TGGAGGTGCA

TAATGCCAAG ACAAAGCCAC GGGAGGAGCAGTTCAACAGC

ACGTTCCGTG TGGTCAGCGT CCTCACCGTT GTGCACCAGGACTGGCTGAA

CGGCAAGGAG TACAAGTGCA AGGTCTCCAA

CAAAGGCCTCCCAGCCCCCA TCGAGAAAAC CATCTCCAAA

ACCAAAGGGC AGCCCCGAGAACCACAGGTG TACACCCTGC

CCCCATCCCG GGAGGAGATG ACCAAGAACCAGGTCAGCCT

GACCTGCCTG GTCAAAGGCT TCTACCCCAG CGACATCGCCGTGGAGTGGG

AGAGCAATGG GCAGCCGGAG AACAACTACA

AGACCACACCTCCCATGCTG GACTCCGACG GCTCCTTCTT CCTCTACAGC

AAGCTCACCGTGGACAAGAG CAGGTGGCAG CAGGGGAACG

TCTTCTCATG CTCCGTGATGCATGAGGCTC TGCACAACCA CTACACGCAG

SalI
            AAGAGCCTCT CCCTGTCTCCGGGTAAATGA TAAGTCGAC
```

The linear plasmid pDSRα19:hIgG2C₁ was prepared by digesting the pDSR19:human variable region/human constant region IgG2 plasmid with the restriction enzymes XbaI and BsmBI to remove the human variable region and purified using a QIAquick Gel Extraction kit. The linear plasmid pDSRα19:hIgG2C$_H$ containing the 1 kbp human IgG2 constant region domain was used to accept hybridoma derived αIL-1R antibody variable regions.

Construction of the Anti-IL1-RI IgG2 Heavy Chain Expression Clone

The αIL-1R1 15C4 heavy chain variable region fragment, described above, was ligated into the mammalian expression vector pDSRα19:hIgG2C$_H$. The 15C4 heavy chain IgG2 expression clone was DNA sequenced to confirm that it encoded the same heavy chain variable region peptide that was identified in the 15C4 hybridoma. The final expression vector, pDSRα 19:15C4 IgG2 heavy chain was 6161 base pairs and contains the seven functional regions described in Table 10.

TABLE 10

| Plasmid Base Pair Number: | |
|---|---|
| 2 to 881 | A transcription termination/polyadenylation signal from the α-subunit of the bovine pituitary glycoprotein hormone (α-FSH) (Goodwin et al., 1983, Nucleic Acids Res. 11:6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al., 1982, Proc. Natl. Acad. Sci. U.S.A. 79:6522-6; Nunberg et al., 1980, Cell 19:355-64; Setzer et al., 1982, J. Biol. Chem. 257:5143-7; McGrogan et al., 1985, J. Biol. (Chem. 260:2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, Mol. Cell Biol. 8:466-72, Genbank Accession Number J02400) |
| 4299 to 4565 | A translational enhancer element from the HTLV-1 LTR domain (Seiki et al., 1983, Proc. Natl. Acad. Sci. U.S.A. 80:3618-22, Genbank Accession Number J02029) |
| 4574 to 4730 | An intron from the SV40 16S, 19S splice donor/acceptor signals (Okayama and Berg, 1983. Mol. Cell Biol. 3:280-9, Genbank Accession Number J02400) |
| 4755 to 6161 | The 15C4 heavy chain IgG2 cDNA between the XbaI and SalI sites |

Construction of pDSR19:hIgG4$C_H$

A pDSRα19:human variable region/human constant region IgG4 (hVh/hCh4) MAb expression plasmid was constructed as the result of a three-piece ligation of XbaI and BsmBI terminated human antibody variable region PCR product, a gel isolated BsmBI and SalI digested human IgG4 constant region ($C_{H1}$, hinge, $C_{H2}$ and $C_{H3}$ domains) fragment and a linearized pDSRa19 with XbaI and SalI ends. The final expression vector, pDSRα19:human variable region/human constant region IgG4 (hVh/hCh4) (see co-owned and co-pending U.S. Provisional Patent Application No. 60/370,407, filed Apr. 5, 2002, "Human Anti-OPGL Neutralizing Antibodies As Selective OPGL Pathway Inhibitors"), is 6167 base pairs and contains the 7 functional regions described in Table 11.

TABLE 11

| Plasmid Base Pair Number: | |
|---|---|
| 2 to 881 | A transcription termination/polyadenylation signal from the α-subunit of the bovine pituitary glycoprotein hormone (α-FSH) (Goodwin et al., 1983, *Nucleic Acids Res.* 11:6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al., 1982, *Proc. Natl, Acad, Sci.* U.S.A. 79:6522-6; Nunberg et al., 1980, *Cell* 19:355-64; Setzer et al., 1982, *J. Biol. Chem.* 257:5143-7; McGrogan et al., 1985, *J. Biol. Chem.* 260:2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, *Mol. Cell Biol.* 8:466-72, Genbank Accession Number J02400) |
| 4299 to 4565 | A translational enhancer element from the HTLV-1 LTR domain (Seiki et al., 1983, *Proc. Natl. Acad. Sci.* U.S.A. 80:3618-22, Genbank Accession Number J02029) |
| 4574 to 4730 | An intron from the SV40 16S, 19S splice donor/acceptor signals (Okayama and Berg, 1983. *Mol. Cell Biol.* 3:280-9, Genbank Accession Number J02400) |
| 4755 to 6167 | The hVh/hCh4 heavy chain cDNA between the XbaI and SalI sites. The sequence of this heavy chain fragment appears below (SEQ ID NO: 58) with the restriction sites underlined:<br>XbaI<br>TCT AGACCACCAT GGACATGAGG GTCCCCGCTC AGCTCCTGGG<br><br>GCTCCTGCTA TTGTGGTTGA GAGGTGCCAG ATGTGAGGTC<br><br>CAGCTGGTGCAGTCTGGGGG AGGCTTGGTA CATCCTGGGG |

TABLE 11-continued

```
Plasmid Base
Pair Number:
         GGTCCCTGAG ACTCTCCTGTGCAGGCTCTG GATTCACCTT CAGTGGCCAT

GCTTTGCACT GGGTTCGCCAGGCTCCAGGA AAAGGTCTGG AGTGGGTATC

AGGTATTGGT ACTCATGGTGGGACATACTA TGCAGACTCC GTGAAGGGCC

GATTCACCAT CTCCAGAGACAATGCCAAGA ACTCCTTGTT TCTTCAAATG

AACAGCCTGA GCGCCGAGGACATGGCTGTG TATTACTGTA

CAAGAAGAAA CTGGGGACAA TTTGACTACTGGGGCCAGGG

BsmB1
         AACCCTGGTC ACCGTCTCTA GTGCCAGCAC CAAGGGGCCATCCGTCTTCC

CCCTGGCGCC CTGCTCCAGG AGCACCTCCG

AGAGCACAGCCGCCCTGGGC TGCCTGGTCA AGGACTACTT

CCCCGAACCG GTGACGGTGTCGTGGAACTC AGGCGCCCTG

ACCAGCGGCG TGCACACCTT CCCGGCTGTCCTACAGTCCT CAGGACTCTA

CTCCCTCAGC AGCGTGGTGA CCGTGCCCTCCAGCAGCTTG GGCACGAAGA

CCTACACCTG CAACGTAGAT CACAAGCCCAGCAACACCAA

GGTGGACAAG AGAGTTGAGT CCAAATATGG TCCCCCATGCCCATCATGCC

CAGCACCTGA GTTCCTGGGG GGACCATCAG TCTTCCTGTTCCCCCCAAAA

CCCAAGGACA CTCTCATGAT CTCCCGGACC CCTGAGGTCACGTGCGTGGT

GGTGGACGTG AGCCAGGAAG ACCCCGAGGT

CCAGTTCAACTGGTACGTGG ATGGCGTGGA GGTGCATAAT

GCCAAGACAA AGCCGCGGGAGGAGCAGTTC AACAGCACGT

ACCGTGTGGT CAGCGTCCTC ACCGTCCTGCACCAGGACTG GCTGAACGGC

AAGGAGTACA AGTGCAAGGT CTCCAACAAAGGCCTCCCGT

CCTCCATCGA GAAAACCATC TCCAAAGCCA

AAGGGCAGCCCCGAGAGCCA CAGGTGTACA CCCTGCCCCC

ATCCCAGGAG GAGATGACCAAGAACCAGGT CAGCCTGACC

TGCCTGGTCA AAGGCTTCTA CCCCAGCGACATCGCCGTGG

AGTGGGAGAG CAATGGGCAG CCGGAGAACA

ACTACAAGACCACGCCTCCC GTGCTGGACT CCGACGGCTC CTTCTTCCTC

TACAGCAGGCTAACCGTGGA CAAGAGCAGG TGGCAGGAGG

GGAATGTCTT CTCATGCTCCGTGATGCATG AGGCTCTGCA CAACCACTAC

SalI
         ACACAGAAGA GCCTCTCCCTGTCTCTGGGT AAATGATAAG TCGAC
```

The linear plasmid pDSRα19:hIgG4C$_H$ was prepared by digesting the pDSR19:human variable region/human constant region IgG4 plasmid with the restriction enzymes XbaI and BsmBI to remove the human variable region and purified using a QIAquick Gel Extraction kit. The linear plasmid pDSRα19:hIgG4C$_H$ containing the I kbp human IgG4 constant region domain was used to accept hybridoma derived αIL-1R antibody variable regions.

Construction of the Anti-IL1-RI IgG4Heavy Chain Expression Clone

The αIL-1R115C4 heavy chain variable region fragment, described above, was ligated into the mammalian expression vector pDSRα19:hIgG4C$_H$. The 15C4 heavy chain IgG4 expression clone was DNA sequenced to confirm that it encoded the same heavy chain variable region peptide that was identified in the 15C4 hybridoma. The final expression vector, pDSRα19:15C4 IgG4 heavy chain was 6164 base pairs and contains the seven functional regions described in Table 12.

TABLE 12

| Plasmid Base Pair Number: | |
|---|---|
| 2 to 881 | A transcription termination/polyadenylation signal from the α-subunit of the bovine pituitary glycoprotein hormone (α-FSH) (Goodwin et al., 1983, Nucleic Acids Res. 11:6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al., 1982, Proc. Natl. Acad. Sci. U.S.A. 79:6522-6; Nunberg et al., 1980, Cell 19:355-64; Setzer et al., 1982, J. Biol. Chem. 257:5143-7; McGrogan et al., 1985,.J. Biol. (Chem. 260:2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, Mol. Cell Biol. 8:466-72, Genbank Accession Number J02400) |
| 4299 to 4565 | A translational enhancer element from the HTLV-1 LTR domain (Seiki et al., 1983, Proc. Natl. Acad. Sci. U.S.A. 80:3618-22, Genbank Accession Number J02029) |
| 4574 to 4730 | An intron from the SV40 16S, 19S splice donor/acceptor signals (Okayama and Berg, 1983. Mol. Cell Biol. 3:280-9, Genbank Accession Number J02400) |
| 4755 to 6164 | The 15C4 heavy chain IgG4 cDNA between the XbaI and SalI sites |

Example 7

Expression of Anti-IL-1R1 Antibodies in Chinese Hamster Ovary (CHO) Cells

Recombinant anti-IL-1R1 antibodies are generated in Chinese hamster ovary cells, specifically CHO AM-1/D, as disclosed in U.S. Pat. No. 6,210,924 (incorporated by reference). Briefly, the DNA sequences encoding the complete heavy or light chains of each anti-IL-1R1 antibody of the invention are cloned into expression vectors. CHO AM-1/D cells are co-transfected with an expression vector capable of expressing a complete heavy chain and an expression vector expressing the complete light chain of the appropriate anti-IL-1R1 antibody. For example, to generate the 26F5 antibody, cells are co-transfected with a vector capable of expressing a complete light chain comprising the amino acid sequence as set forth in SEQ ID NO:38 and a vector capable of expressing a complete heavy chain comprising the amino acid sequence set forth in SEQ ID NO: 20, SEQ ID NO: 22, or SEQ ID NO: 24. To generate the 27F2 antibody, cells are co-transfected with a vector capable of expressing a complete light chain comprising the amino acid sequence as set forth in SEQ ID NO: 38 and a vector capable of expressing a complete heavy chain comprising the amino acid sequence set forth in SEQ ID NO: 26, SEQ ID NO: 28, or SEQ ID NO: 30. To generate the 15C4 antibody, cells are co-transfected with a vector capable of expressing a complete light chain comprising the amino acid sequence as set forth in SEQ ID NO: 40 and a vector capable of expressing a complete heavy chain comprising the amino acid sequence set forth in SEQ ID NO: 32, SEQ ID NO: 34, or SEQ ID NO: 36. Table 13 summarizes the complete heavy and complete light chains for the various IL-1R1 antibodies. The designation " . . . /IgG_" describes the sequence of the constant region for the particular antibody.

TABLE 13

| Antibody | Heavy Chain Variable Region + Heavy Chain Constant Region | Complete Heavy Chain |
|---|---|---|
| 26F5/IgG1 (nucleotide) | SEQ ID NO: 9 + SEQ ID NO: 1 | SEQ ID NO: 19 |
| 26F5/IgG1 (amino acid) | SEQ ID NO: 10 + SEQ ID NO: 2 | SEQ ID NO: 20 |
| 26F5/IgG2 (nucleotide) | SEQ ID NO: 9 + SEQ ID NO: 5 | SEQ ID NO: 21 |
| 26F5/IgG2 (amino acid) | SEQ ID NO: 10 + SEQ ID NO: 6 | SEQ ID NO: 22 |
| 26F5/IG4 (nucleotide) | SEQ ID NO: 9 + SEQ ID NO: 7 | SEQ ID NO: 23 |
| 26F5/IgG4 (amino acid) | SEQ ID NO: 10 + SEQ ID NO: 8 | SEQ ID NO: 24 |
| 27F2/IgG1 (nucleotide) | SEQ ID NO: 13 + SEQ ID NO: 1 | SEQ ID NO: 25 |
| 27172/IgG1 (amino acid) | SEQ ID NO: 14 + SEQ ID NO: 2 | SEQ ID NO: 26 |
| 27F2/IgG2 (nucleotide) | SEQ ID NO: 13 + SEQ ID NO: 5 | SEQ ID NO: 27 |
| 27F2/IgG2 (amino acid) | SEQ ID NO: 14 + SEQ ID NO: 6 | SEQ ID NO: 28 |
| 27F2/IgG4 (nucleotide) | SEQ ID NO: 13 + SEQ ID NO: 7 | SEQ ID NO: 29 |
| 27F2/IgG4 (amino acid) | SEQ ID NO: 14 + SEQ ID NO: 8 | SEQ ID NO: 30 |
| 15C4/IgG1 (nucleotide) | SEQ ID NO: 15 + SEQ ID NO: 1 | SEQ ID NO: 31 |
| 15C4/IgG1 (amino acid) | SEQ ID NO: 16 + SEQ ID NO: 2 | SEQ ID NO: 32 |
| 15C4/IgG2 (nucleotide) | SEQ ID NO: 15 + SEQ ID NO: 5 | SEQ ID NO: 33 |
| 15C4/IgG2 (amino acid) | SEQ ID NO: 16 + SEQ ID NO: 6 | SEQ ID NO: 34 |
| 15C4/IgG4 (nucleotide) | SEQ ID NO: 15 + SEQ ID NO: 7 | SEQ ID NO: 35 |
| 15C4/IgG1 (amino acid) | SEQ ID NO: 16 + SEQ ID NO: 8 | SEQ ID NO: 36 |
| Antibody | Light Chain Variable Region + Light Chain Constant Region | Complete Light Chain |
| 26F5/27F2 (nucleotide) | SEQ ID NO: 11 + SEQ ID NO: 3 | SEQ ID NO: 37 |
| 261F5/27F2 (amino acid) | SEQ ID NO: 12 + SEQ ID NO: 4 | SEQ ID NO: 38 |
| I5C4 (nucleotide) | SEQ ID NO: 17 + SEQ ID NO: 3 | SEQ ID NO: 39 |
| I5C4 (amino acid) | SEQ ID NO: 18 + SEQ ID NO: 4 | SEQ ID NO: 40 |

Stable expression of anti-IL-1R1 antibodies is achieved by co-transfecting dihydrofolate reductase deficient (DHFR) CHO AM-1/D cells with the expression vectors. Transfections are carried out using standard techniques (calcium phosphate co-precipitation) and DHFR selection. Transfected colonies are isolated and grown to confluence in 24-well plates. Antibodies produced by transfected cells are examined for appropriate folding and neutralizing activity. Clones overproducing appropriately folded anti-IL-1R1 antibodies of the IgG1, IgG2, and IgG4 isotypes are selected and antibodies are purified as described below.

Example 8

Production of anti-IL-1R1 Antibody

Anti-IL-1R1 antibodies are produced by expression in a clonal line of CHO cells. For each production run, cells from a single vial are thawed into serum-free cell culture media. The cells are grown initially in a T-flask and are serially expanded through a series of spinner flasks until sufficient inoculum has been generated to seed a 20 L bioreactor. Following growth for 5-10 days, the culture is then used to inoculate a 300 L bioreactor. Following growth for an additional 5-10 days, the culture is used to inoculate a 2000 L bioreactor. Production is carried out in a 2000 L bioreactor using a fed batch culture, in which a nutrient feed containing concentrated media components is added to maintain cell growth and culture viability. Production lasts for approximately two weeks during which time anti-IL1-R1 antibody is constitutively produced by the cells and secreted into the cell culture medium.

The production reactor is controlled at set pH, temperature, and dissolved oxygen level: pH is controlled by carbon dioxide gas and sodium carbonate addition; dissolved oxygen is controlled by air, nitrogen, and oxygen gas flows.

At the end of production, the cell broth is fed into a disk stack centrifuge and the culture supernatant is separated from the cells. The concentrate is further clarified through a depth filter followed by a 0.2 μm filter. The clarified conditioned media is then concentrated by tangential flow ultrafiltration. The conditioned media is concentrated 15- to 30-fold. The resulting concentrated conditioned medium is then either processed through purification or frozen for purification at a later date.

Example 9

Epitope Mapping Using Avidin-Fusion Proteins

To generate avidin-fusion proteins, cDNA encoding chicken avidin (with endogenous signal sequence) was joined with the 5' end of cDNAs encoding the mature extracellular domains of human- or cynomolgus IL-1R1 fused to a FLAG-tag sequence at the 3' end. The FLAG-tagged fusion genes were assembled in a pALTERMAX vector using conventional molecular techniques. The amino acid sequence of the avidin-human IL-1R1 fusion protein is shown in FIG. 23 (SEQ ID NO: 59). The amino acid sequence of the avidin-cynomolgus IL-1R1 fusion protein is shown in FIG. 24 (SEQ ID NO: 60). A panel of mutant avidin-cynoIL-1R1-FLAG proteins in which human amino acids were substituted for the corresponding cynomolgus residues was generated using the Altered Sites II Mammalian In Vitro Mutagenesis System (Promega Corp.). The mutations are illustrated in FIG. 24.

Plasmids encoding the avidin-cynoIL-1R mutant and wild-type proteins as well as the avidin-huIL-1R1-FLAG protein were transiently transfected into 293T cells using Cytofectine transfection reagent (Bio-Rad Laboratories, Inc.). Mock transfectants were used as negative controls. Anti-huIL-1R1 monoclonal antibody (MAb) binding to these proteins was evaluated by Western blot and bead-based binding assays using conditioned medium (CM) harvested from the transfected cells.

For Western blot analysis, CM was diluted 1:3 in non-reducing SDS sample buffer, boiled for 5-10 minutes and loaded onto 10% Tris-glycine gels. Following SDS-PAGE and Western transfer, the membranes were blocked with 3% BSA/1% ovalbumin in PBS/0.1% Tween-20 (PBST) and stained with anti-huIL-1R1 MAbs. A goat anti-human IgG-Fc-HRP antibody (Pierce Chemical Co.) diluted 1: 15,000 in PBST was used for secondary detection. Anti-FLAG detection was used to normalize for protein loading. Image capture and densitometry were performed using a Fluor Chem 8000 digital imaging system (Alpha Innotech Corp.). The signal intensities for the anti-huIL-1R1 MAbs were normalized against the values for the anti-FLAG antibody to account for variation in protein loading. Antibody binding was expressed as a percentage of binding to the avidin-human IL-1R1-FLAG.

The results of the Western blot are shown in FIG. 25A. FIG. 25B shows the densitometric analysis of a duplicate set of Western blot experiments. Human residues critical for antibody binding are those that restore signal when substituted into cynoIL-1RI. In general, mutations 1 and 2 (illustrated in FIG. 24), alone or in combination, restored binding to many of the antibodies (15C4/IgG2, 5B8, 1C2, 24H2, 16E9, 26E4 and 20G1) while mutations 10.1 and 10.2 did not. None of these antibodies bound to wild-type cynoIL-1R1. Two antibodies (27F2 and 19C8) bound consistently to all the mutant proteins as well as to wild-type cynoIL-1R1. This suggested that epitope 4 (residues Y279-V281 of cynoIL-1R1), identified in the rat/human paralog proteins and unchanged in cynomolgus IL-1R1, was the dominant epitope for these antibodies. Epitope 4 is bold, italicized, and underlined in the amino acid sequence shown in FIG. 24.

In the multiplexed bead-based binding assays, avidin fusion proteins were captured by incubation of the CM with biotin-coated fluorescent beads, one bead set per fusion protein (Beadlyte Multi-Biotin 10plex Bead Kit; Upstate Biotechnologies). The beads were washed and pooled in PBST and aliquoted to the wells of a 96-well filter bottom plate (Millipore Corp.). Antibodies (anti-huIL-1R1 MAbs or anti-FLAG MAb) were added at 25 μg/ml and incubated for 1 hour. The beads were again washed and a mixture of Phycoerythrin-conjugated anti-mouse IgG antibody and anti-human IgG $(Fab')_2$ was used to detect antibody binding. After a 1 hour incubation, the beads were washed and resuspended in PBST. Mean fluorescence intensities (MFI) were measured using a Luminex 100 (Luminex Corp). The data were normalized using the MFI values for anti-FLAG MAb binding to account for variation in protein loading. Antibody binding was expressed as a percentage of binding to the avidin-huIL-1R1-FLAG (FIG. 26). The binding pattern of the anti-IL-1R1 antibodies to the avidin-cynoIL1R1-FLAG proteins mutated with human residues as well as to wild-type cynomolgus and human IL-1R1 proteins was consistent with the immunoblot analysis shown in FIG. 25.

It should be understood that the foregoing disclosure emphasizes certain specific embodiments of the invention and that all modifications or alternatives equivalent thereto are within the spirit and scope of the invention as set forth in the appended claims.

We claim:

1. An isolated nucleic acid molecule comprising:
   (a) nucleotide sequences encoding human heavy chain framework regions, a nucleotide sequence encoding a human heavy chain CDR1 region comprising SEQ ID NO: 61, a nucleotide sequence encoding a human heavy chain CDR2 region comprising SEQ ID NO: 64, and a nucleotide sequence encoding a human heavy chain CDR3 region comprising SEQ ID NO: 67; and nucleotide sequences encoding human light chain framework regions, a nucleotide sequence encoding a human light chain CDR1 region comprising SEQ ID NO: 70, a nucleotide sequence encoding a human light chain CDR2 region comprising SEQ ID NO: 72, and a nucleotide sequence encoding a human light chain CDR3 region comprising SEQ ID NO: 74; or
   (b) nucleotide sequences encoding human heavy chain framework regions, a nucleotide sequence encoding a human heavy chain CDR1 region comprising SEQ ID NO: 62, a nucleotide sequence encoding a human heavy chain CDR2 region comprising SEQ ID NO: 65, and a nucleotide sequence encoding a human heavy chain CDR3 region comprising SEQ ID NO: 68; and nucleotide sequences encoding human light chain framework regions, a nucleotide sequence encoding a human light chain CDR1 region comprising SEQ ID NO: 70, a nucleotide sequence encoding a human light chain CDR2 region comprising SEQ ID NO: 72, and a nucleotide sequence encoding a human light chain CDR3 region comprising SEQ ID NO: 74.

2. The isolated nucleic acid molecule of claim 1, wherein the isolated nucleic acid molecule comprises a combination of nucleic acid sequences that encode a heavy chain variable region and a light chain variable region of an antibody that specifically binds IL-1R1, wherein the combination comprises:
   (a) SEQ ID NO: 89 and SEQ ID NO: 88; or
   (b) SEQ ID NO: 87 and SEQ ID NO: 88.

3. An isolated nucleic acid molecule comprising a nucleotide sequence that encodes a human antibody that specifically binds IL-1R1, wherein the antibody comprises:
   (a) a heavy chain having a heavy chain variable region, or an antigen-binding fragment thereof, wherein the heavy chain variable region comprises the amino acid sequence encoded by SEQ ID NO: 89, and wherein the antigen-binding fragment comprises an N-terminal or C-terminal deletion of the amino acid sequence encoded by SEQ ID NO: 89, wherein the N-terminal or C-terminal deletion comprises SEQ ID NO: 61, SEQ ID NO: 64, and SEQ ID NO: 67; or (b) a heavy chain having a heavy chain variable region, or an antigen-binding fragment thereof, wherein the heavy chain variable region comprises the amino acid sequence encoded by SEQ ID NO: 87, and wherein the antigen-binding fragment comprises an N-terminal or C-terminal deletion of the amino acid sequence encoded by SEQ ID NO: 87, wherein the N-terminal or C-terminal deletion comprises SEQ ID NO: 62, SEQ ID NO: 65, and SEQ ID NO: 68.

4. An isolated nucleic acid molecule comprising a nucleotide sequence that encodes a human antibody that specifically binds IL-1R1, wherein the antibody comprises:

(a) a heavy chain having a heavy chain variable region, or an antigen-binding fragment thereof, wherein the heavy chain variable region comprises the amino acid sequence encoded by SEQ ID NO: 89, and wherein the antigen-binding fragment comprises SEQ ID NO: 61, SEQ ID NO: 64, and SEQ ID NO: 67, and wherein the antibody comprises a light chain having a light chain variable region, or an antigen-binding fragment thereof, wherein the light chain variable region comprises the amino acid sequence encoded by SEQ ID NO: 88, and wherein the antigen-binding fragment comprises SEQ ID NO: 70, SEQ ID NO: 72, and SEQ ID NO: 74; or (b) a heavy chain having a heavy chain variable region, or an antigen-binding fragment thereof, wherein the heavy chain variable region comprises the amino acid sequence encoded by SEQ ID NO: 87, and wherein the antigen-binding fragment comprises SEQ ID NO: 62, SEQ ID NO: 65, and SEQ ID NO: 68, and wherein the antibody comprises a light chain having a light chain variable region, or an antigen-binding fragment thereof, wherein the light chain variable region comprises the amino acid sequence encoded by SEQ ID NO: 88, and wherein the antigen-binding fragment comprises SEQ ID NO: 70, SEQ ID NO: 72, and SEQ ID NO: 74.

5. The isolated nucleic acid molecule of claim 1 or 4 wherein the nucleic acid molecule encodes an antibody that is an IgG2 antibody.

6. The isolated nucleic acid molecule of claim 1 or 4, wherein the nucleic acid molecule encodes an antibody that is a fully human antibody.

7. A vector comprising the nucleic acid molecule of any of claim 1 or 4.

8. A vector comprising the nucleic acid molecule of claim 5.

9. A vector comprising the nucleic acid molecule of claim 6.

10. An expression vector comprising the nucleic acid molecule of any of claim 1 or 4.

11. An expression vector comprising the nucleic acid molecule of claim 5.

12. An expression vector comprising the nucleic acid molecule of claim 6.

13. An isolated host cell comprising the vector of claim 7.

14. An isolated host cell comprising the expression vector of claim 10.

15. The host cell of claim 13 that is a eukaryotic cell.

16. The host cell of claim 14 that is a eukaryotic cell.

17. A set of nucleic acid molecules comprising:

(a) a first nucleic acid molecule encoding human heavy chain framework regions, a nucleotide sequence encoding a human heavy chain CDR1 region comprising SEQ ID NO: 61, a nucleotide sequence encoding a human heavy chain CDR2 region comprising SEQ ID NO: 64, and a nucleotide sequence encoding a human heavy chain CDR3 region comprising SEQ ID NO: 67; and a second nucleic acid molecule encoding human light chain framework regions, a nucleotide sequence encoding a human light chain CDR1 region comprising SEQ ID NO: 70, a nucleotide sequence encoding a human light chain CDR2 region comprising SEQ ID NO: 72, and a nucleotide sequence encoding a human light chain CDR3 region comprising SEQ ID NO: 74; or (b) a first nucleic acid molecule encoding human heavy chain framework regions, a nucleotide sequence encoding a human heavy chain CDR1 region comprising SEQ ID NO: 62, a nucleotide sequence encoding a human heavy chain CDR2 region comprising SEQ ID NO: 65, and a nucleotide sequence encoding a human heavy chain CDR3 region comprising SEQ ID NO: 68; and a second nucleic acid molecule encoding human light chain framework regions, a nucleotide sequence encoding a human light chain CDR1 region comprising SEQ ID NO: 70, a nucleotide sequence encoding a human light chain CDR2 region comprising SEQ ID NO: 72, and a nucleotide sequence encoding a human light chain CDR3 region comprising SEQ ID NO: 74.

18. The set of nucleic acid molecules of claim 17, wherein:

(a) the first nucleic acid molecule comprises SEQ ID NO: 89 and the second nucleic acid molecule comprises SEQ ID NO: 88; or (b) the first nucleic acid molecule comprises SEQ ID NO: 87 and the second nucleic acid molecule comprises SEQ ID NO: 88.

19. A set of nucleic acid molecules comprising nucleotide sequences that encode a human antibody that specifically binds IL-1R1, comprising:

(a) a first nucleic acid molecule encoding a human antibody heavy chain having a heavy chain variable region, or an antigen-binding fragment thereof, wherein the heavy chain variable region comprises the amino acid sequence encoded by SEQ ID NO: 9, and wherein the antigen-binding fragment comprises an N-terminal or C-terminal deletion of the amino acid sequence encoded by SEQ ID NO: 9, wherein the N-terminal or C-terminal deletion comprises SEQ ID NO: 61, SEQ ID NO: 64, and SEQ ID NO: 67; and a second nucleic acid molecule encoding a human antibody light chain; or (b) a first nucleic acid molecule encoding a human antibody heavy chain having a heavy chain variable region, or an antigen-binding fragment thereof, wherein the heavy chain variable region comprises the amino acid sequence encoded by SEQ ID NO: 13, and wherein the antigen-binding fragment comprises an N-terminal or C-terminal deletion of the amino acid sequence encoded by SEQ ID NO: 13, wherein the N-terminal or C-terminal deletion comprises SEQ ID NO: 62, SEQ ID NO: 65, and SEQ ID NO: 68; and a second nucleic acid molecule encoding a human antibody light chain.

20. A set of nucleic acid molecules comprising:

(a) a first nucleic acid molecule encoding a human antibody heavy chain having a heavy chain variable region, or an antigen-binding fragment thereof, wherein the heavy chain variable region comprises the amino acid sequence encoded by SEQ ID NO: 89, and wherein the antigen-binding fragment comprises SEQ ID NO: 61, SEQ ID NO: 64, and SEQ ID NO: 67; and a second nucleic acid molecule encoding a human antibody light chain having a light chain variable region, or an antigen-binding fragment thereof, wherein the light chain variable region comprises the amino acid sequence encoded by SEQ ID NO: 88, and wherein the antigen-binding fragment comprises SEQ ID NO: 70, SEQ ID NO: 72, and SEQ ID NO: 74; or (b) a first nucleic acid molecule encoding a human antibody heavy chain having a heavy chain variable region, or an antigen-binding fragment thereof, wherein the heavy chain variable region comprises the amino acid sequence encoded by SEQ ID NO: 87, and wherein the antigen-binding fragment comprises SEQ ID NO: 62, SEQ ID NO: 65, and SEQ ID NO: 68; and a second nucleic acid molecule encoding a human antibody light chain having a light chain variable region, or an antigen-binding fragment thereof, wherein the light chain variable region comprises the amino acid sequence encoded by SEQ ID NO: 88, and wherein the antigen-binding fragment comprises SEQ ID NO: 70, SEQ ID NO: 72, and SEQ ID NO: 74.

21. A set of nucleic acid molecules comprising:
(a) a first nucleic acid molecule comprising SEQ ID NO: 89; and a second nucleic acid molecule comprising SEQ ID NO: 88; or
(b) a first nucleic acid molecule comprising SEQ ID NO: 87; and a second nucleic acid molecule comprising SEQ ID NO: 88.

22. A set of vectors comprising the nucleic acid molecules of any of claim 17, 19, 20, or 21, wherein one vector comprises the first nucleic acid molecule and the other vector comprises the second nucleic acid molecule.

23. An isolated host cell comprising the set of vectors of claim 22.

24. The host cell of claim 23 that is a eukaryotic cell.

* * * * *